US011786255B2

(12) United States Patent
Hebert et al.

(10) Patent No.: US 11,786,255 B2
(45) Date of Patent: Oct. 17, 2023

(54) PACKAGING FOR SURGICAL IMPLANT

(71) Applicant: Neurogami Medical, Inc., Mountain View, CA (US)

(72) Inventors: Stephen J. Hebert, San Francisco, CA (US); Bartosz Bojanowski, San Francisco, CA (US)

(73) Assignee: NEUROGAMI MEDICAL, INC, Mountain View, CA (US)

( * ) Notice: Subject to any disclaimer, the term of this patent is extended or adjusted under 35 U.S.C. 154(b) by 282 days.

(21) Appl. No.: 17/175,037

(22) Filed: Feb. 12, 2021

(65) Prior Publication Data

US 2021/0219984 A1     Jul. 22, 2021

Related U.S. Application Data

(60) Division of application No. 15/953,261, filed on Apr. 13, 2018, now Pat. No. 10,925,611, which is a
(Continued)

(51) Int. Cl.
*A61B 17/12*     (2006.01)
*A61F 2/00*     (2006.01)
(Continued)

(52) U.S. Cl.
CPC .... *A61B 17/12118* (2013.01); *A61B 17/1215* (2013.01); *A61B 17/12031* (2013.01);
(Continued)

(58) Field of Classification Search
CPC .......... A61B 17/1214; A61B 17/12147; A61B 17/12172; A61B 2017/0053; A61B 50/30;
(Continued)

(56) References Cited

U.S. PATENT DOCUMENTS 4,994,069 A    2/1991   Ritchart et al.
5,122,136 A    6/1992   Guglielmi et al.
(Continued)

FOREIGN PATENT DOCUMENTS

CN           1671330        9/2005
CN     203885554 U     10/2014
(Continued)

OTHER PUBLICATIONS

European Search Report and Written Opinion EP 20741592 dated Jan. 26, 2022.
(Continued)

*Primary Examiner* — Martin T Ton
(74) *Attorney, Agent, or Firm* — Neil D. Gershon

(57) ABSTRACT

A packaging for an implant to hold the implant in a first condition. The packaging including a first packaging tube and a container, wherein the implant is movable from the container into the first tube and maintained within the first tube in a second condition, the implant having a first transverse dimension in the first condition and a second transverse dimension in the second condition, the second transverse dimension being less than the first transverse dimension.

20 Claims, 37 Drawing Sheets

Related U.S. Application Data continuation-in-part of application No. 14/997,094, filed on Jan. 15, 2016, now Pat. No. 9,962,146.

(60) Provisional application No. 62/622,869, filed on Jan. 27, 2018, provisional application No. 62/502,663, filed on May 6, 2017, provisional application No. 62/105,648, filed on Jan. 20, 2015.

(51) Int. Cl.

| | |
|---|---|
| A61B 17/00 | (2006.01) |
| A61F 2/82 | (2013.01) |
| A61F 2/90 | (2013.01) |
| A61F 2/07 | (2013.01) |
| A61F 2/06 | (2013.01) |

(52) U.S. Cl.
CPC ...... *A61B 17/12172* (2013.01); *A61F 2/0095* (2013.01); *A61B 17/0057* (2013.01); *A61B 17/12145* (2013.01); *A61B 17/12163* (2013.01); *A61B 17/12177* (2013.01); *A61B 2017/0053* (2013.01); *A61B 2017/00526* (2013.01); *A61B 2017/00893* (2013.01); *A61B 2017/00898* (2013.01); *A61B 2017/00942* (2013.01); *A61B 2017/12054* (2013.01); *A61F 2/06* (2013.01); *A61F 2/07* (2013.01); *A61F 2/90* (2013.01); *A61F 2002/823* (2013.01); *A61F 2210/0076* (2013.01); *A61F 2230/0067* (2013.01); *A61F 2230/0091* (2013.01)

(58) Field of Classification Search
CPC .... A61B 2050/3008; A61B 2050/3009; A61B 2050/3013; A61F 2230/0091; A61F 2/9522; A61L 2430/36; A61M 25/002
See application file for complete search history.

(56) References Cited

U.S. PATENT DOCUMENTS

| | | |
|---|---|---|
| 5,226,911 A | 7/1993 | Chee et al. |
| 5,234,437 A | 8/1993 | Sepetka |
| 5,250,071 A | 10/1993 | Palermo |
| 5,261,916 A | 11/1993 | Engelson |
| 5,304,195 A | 4/1994 | Twyford, Jr. |
| 5,350,397 A | 9/1994 | Palermo |
| 5,354,295 A | 10/1994 | Guglielmi et al. |
| 5,382,259 A | 1/1995 | Phelps et al. |
| 5,423,849 A | 6/1995 | Engelson et al. |
| 5,485,667 A | 1/1996 | Kleshinski |
| 5,522,836 A | 6/1996 | Palermo |
| 5,645,558 A | 7/1997 | Horton |
| 5,690,666 A | 11/1997 | Berenstein et al. |
| 5,743,905 A | 4/1998 | Eder et al. |
| 5,800,455 A | 9/1998 | Palermo |
| 5,826,587 A | 10/1998 | Berenstein et al. |
| 5,895,391 A | 4/1999 | Farnholtz |
| 5,911,731 A | 6/1999 | Pham et al. |
| 5,935,145 A | 8/1999 | Villar et al. |
| 5,935,148 A | 8/1999 | Villar et al. |
| 5,944,733 A | 8/1999 | Engelson |
| 5,964,797 A | 10/1999 | Ho |
| 5,984,929 A | 11/1999 | Bashiri et al. |
| 6,059,779 A | 5/2000 | Mills |
| 6,063,070 A | 5/2000 | Eder |
| 6,096,034 A | 8/2000 | Kupiecki et al. |
| 6,136,015 A | 10/2000 | Kurz et al. |
| 6,156,061 A | 12/2000 | Wallace et al. |
| 6,159,165 A | 12/2000 | Ferrera et al. |
| 6,165,178 A | 12/2000 | Bashiri et al. |
| 6,168,615 B1 | 1/2001 | Ken et al. |
| 6,171,326 B1 | 1/2001 | Ferrera et al. |
| 6,193,708 B1 | 2/2001 | Ken et al. |
| 6,231,586 B1 | 5/2001 | Mariant |
| 6,238,415 B1 | 5/2001 | Sepetka et al. |
| 6,254,592 B1 | 7/2001 | Samson et al. |
| 6,280,457 B1 | 8/2001 | Wallace et al. |
| 6,287,318 B1 | 9/2001 | Villar et al. |
| 6,296,622 B1 | 10/2001 | Kurz et al. |
| 6,299,627 B1 | 10/2001 | Eder et al. |
| 6,306,153 B1 | 10/2001 | Kurz et al. |
| 6,309,367 B1 | 10/2001 | Boock |
| 6,312,421 B1 | 11/2001 | Boock |
| 6,371,972 B1 | 4/2002 | Wallace et al. |
| 6,375,668 B1 | 4/2002 | Gifford |
| 6,375,669 B1 | 4/2002 | Rosenbluth et al. |
| 6,383,204 B1 | 5/2002 | Ferrera et al. |
| 6,409,721 B1 | 6/2002 | Wheelock et al. |
| 6,425,914 B1 | 7/2002 | Wallace et al. |
| 6,454,780 B1 | 9/2002 | Wallace |
| 6,458,119 B1 | 10/2002 | Berenstein et al. |
| 6,475,169 B2 | 11/2002 | Ferrera |
| 6,544,275 B1 | 4/2003 | Teoh |
| 6,551,305 B2 | 4/2003 | Ferrera et al. |
| 6,585,754 B2 | 7/2003 | Wallace et al. |
| 6,589,230 B2 | 7/2003 | Gia et al. |
| 6,605,101 B1 | 8/2003 | Schaefer et al. |
| 6,623,493 B2 | 9/2003 | Wallace et al. |
| 6,626,928 B1 | 9/2003 | Raymond et al. |
| 6,660,020 B2 | 12/2003 | Wallace |
| 6,679,903 B2 | 1/2004 | Kurz |
| 6,716,223 B2 | 4/2004 | Leopold et al. |
| 6,746,475 B1 | 6/2004 | Rivelli, Jr. |
| 6,786,876 B2 | 9/2004 | Cox |
| 6,802,851 B2 | 10/2004 | Jones et al. |
| 6,872,218 B2 | 3/2005 | Ferrera |
| 6,913,618 B2 | 7/2005 | Denardo et al. |
| 6,929,654 B2 | 8/2005 | Teoh et al. |
| 7,070,608 B2 | 7/2006 | Kurz et al. |
| 7,083,632 B2 | 8/2006 | Avellanet et al. |
| 7,201,768 B2 | 4/2007 | Diaz et al. |
| 7,232,461 B2 | 6/2007 | Ramer |
| 7,241,301 B2 | 7/2007 | Thramann et al. |
| 7,316,701 B2 | 1/2008 | Ferrera et al. |
| 7,326,225 B2 | 2/2008 | Ferrera et al. |
| 7,410,482 B2 | 8/2008 | Murphy et al. |
| 7,442,382 B2 | 10/2008 | Henson et al. |
| 7,488,332 B2 | 2/2009 | Teoh et al. |
| 7,494,687 B2 | 2/2009 | Cox |
| 7,569,626 B2 | 8/2009 | Truckai |
| 7,572,288 B2 | 8/2009 | Cox |
| 7,599,933 B2 | 10/2009 | Domany et al. |
| 7,608,088 B2 | 10/2009 | Jones et al. |
| 7,678,135 B2 | 3/2010 | Maahs et al. |
| 7,695,484 B2 | 4/2010 | Wallace et al. |
| 7,695,488 B2 | 4/2010 | Berenstein et al. |
| 7,708,754 B2 | 5/2010 | Balgobin et al. |
| 7,708,755 B2 | 5/2010 | David |
| 7,740,637 B2 | 6/2010 | Gandhi et al. |
| 7,780,680 B2 | 8/2010 | Gandhi et al. |
| 7,842,054 B2 | 11/2010 | Greene, Jr. et al. |
| 7,842,068 B2 | 11/2010 | Ginn |
| 8,002,789 B2 | 8/2011 | Ramzipoor et al. |
| 8,016,852 B2 | 9/2011 | Ho et al. |
| 8,034,075 B2 | 10/2011 | Dehnad |
| 8,142,456 B2 | 3/2012 | Rosqueta et al. |
| 8,172,862 B2 | 5/2012 | Wallace et al. |
| 8,182,506 B2 | 5/2012 | Fitz et al. |
| 8,221,483 B2 | 7/2012 | Ford et al. |
| 8,257,394 B2 | 9/2012 | Saadat et al. |
| 8,267,923 B2 | 9/2012 | Murphy et al. |
| 8,267,955 B2 | 9/2012 | Patterson et al. |
| 8,273,100 B2 | 9/2012 | Martinez |
| 8,292,914 B2 | 10/2012 | Morsi |
| 8,298,256 B2 | 10/2012 | Gandhi et al. |
| 8,333,796 B2 | 12/2012 | Tompkins et al. |
| 8,361,104 B2 | 1/2013 | Jones et al. |
| 8,361,138 B2 | 1/2013 | Adams |
| 8,376,996 B2 | 2/2013 | Wilson et al. |
| 8,398,701 B2 | 3/2013 | Berez et al. |
| 8,425,548 B2 | 4/2013 | Connor |
| 8,439,871 B2 | 5/2013 | Wilson et al. |
| 8,444,668 B2 | 5/2013 | Jones et al. |

(56) References Cited

U.S. PATENT DOCUMENTS

| | | |
|---|---|---|
| 8,470,013 B2 | 6/2013 | Duggal et al. |
| 8,486,101 B2 | 7/2013 | Tran et al. |
| 8,535,345 B2 | 9/2013 | Desai et al. |
| 8,540,671 B2 | 9/2013 | Wilson et al. |
| 8,545,530 B2 | 10/2013 | Eskridge et al. |
| 8,597,320 B2 | 12/2013 | Sepetka et al. |
| 8,608,772 B2 | 12/2013 | Wilson et al. |
| 8,657,816 B2 | 2/2014 | Truckai |
| 8,663,320 B2 | 3/2014 | Chambers et al. |
| 8,690,907 B1 | 4/2014 | Janardhan |
| 8,715,312 B2 | 5/2014 | Burke et al. |
| 8,715,316 B1 | 5/2014 | Janardhan et al. |
| 8,715,317 B1 | 5/2014 | Janardhan |
| 8,764,788 B2 | 7/2014 | Martinez |
| 8,771,265 B2 | 7/2014 | Truckai |
| 8,771,294 B2 | 7/2014 | Sepetka et al. |
| 8,777,979 B2 | 7/2014 | Shrivastava et al. |
| 8,795,316 B2 | 8/2014 | Balgobin |
| 8,801,747 B2 | 8/2014 | Stauss et al. |
| 8,833,224 B2 | 9/2014 | Thompson et al. |
| 8,876,855 B2 | 11/2014 | Plaza et al. |
| 8,888,806 B2 | 11/2014 | Desai et al. |
| 8,926,650 B2 | 1/2015 | Que |
| 8,932,317 B2 | 1/2015 | Marks et al. |
| 8,992,717 B2 | 3/2015 | Zeroni |
| 8,998,947 B2 | 4/2015 | Aboytes et al. |
| 9,011,480 B2 | 4/2015 | Divino et al. |
| 9,011,482 B2 | 4/2015 | Wallace et al. |
| 9,060,777 B1 | 6/2015 | Wallace et al. |
| 9,186,151 B2 | 11/2015 | Tompkins et al. |
| 9,192,389 B2 | 11/2015 | Tekulve |
| 9,295,473 B2 | 3/2016 | Hewitt et al. |
| 9,301,764 B2 | 4/2016 | White, Jr. et al. |
| 9,314,326 B2 | 4/2016 | Wallace et al. |
| 9,451,963 B2 | 9/2016 | Cruise et al. |
| 9,561,121 B2 | 2/2017 | Sudin et al. |
| 9,572,694 B2 | 2/2017 | Caro et al. |
| 9,579,104 B2 | 2/2017 | Beckham et al. |
| 9,592,068 B2 | 3/2017 | Janardhan et al. |
| 9,615,832 B2 | 4/2017 | Bose et al. |
| 9,687,245 B2 | 6/2017 | Molaei et al. |
| 9,763,667 B2 | 9/2017 | Fercik Grant et al. |
| 9,775,494 B2 | 10/2017 | Takasugi |
| 9,775,590 B2 | 10/2017 | Ryan et al. |
| 9,855,052 B2 | 1/2018 | Aboytes et al. |
| 9,867,622 B2 | 1/2018 | Bowman |
| 9,907,556 B2 | 3/2018 | Truckai |
| 9,907,557 B2 | 3/2018 | Wallace et al. |
| 9,962,146 B2 | 5/2018 | Hebert |
| 9,968,360 B2 | 5/2018 | Stoppenhagen |
| 9,974,544 B2 | 5/2018 | Tekulve |
| 9,999,413 B2 | 6/2018 | Hebert |
| 10,064,627 B2 | 9/2018 | Aboytes et al. |
| 10,159,490 B2 | 12/2018 | Wallace et al. |
| 10,182,822 B2 | 1/2019 | Freudenthal |
| 10,231,722 B2 | 3/2019 | Hebert |
| 10,285,678 B2 | 5/2019 | Hebert |
| 10,285,679 B2 | 5/2019 | Hebert |
| 10,299,799 B1 | 5/2019 | DeMeritt |
| 10,335,154 B2 | 7/2019 | Johnson et al. |
| 10,736,730 B2 | 8/2020 | Hebert |
| 2002/0002382 A1 | 1/2002 | Wallace et al. |
| 2002/0120276 A1 | 8/2002 | Greene |
| 2002/0128671 A1 | 9/2002 | Wallace et al. |
| 2003/0004533 A1 | 1/2003 | Dieck et al. |
| 2003/0004568 A1 | 1/2003 | Ken et al. |
| 2003/0093111 A1 | 5/2003 | Ken et al. |
| 2003/0204246 A1 | 10/2003 | Chu |
| 2004/0059407 A1 | 3/2004 | Escamilla |
| 2004/0098028 A1 | 5/2004 | Martinez |
| 2005/0149109 A1 | 7/2005 | Wallace |
| 2005/0171572 A1 | 8/2005 | Martinez |
| 2005/0192621 A1 | 9/2005 | Wallace et al. |
| 2005/0251160 A1 | 11/2005 | Saadat |
| 2005/0277978 A1 | 12/2005 | Greenhalgh |
| 2005/0283182 A1 | 12/2005 | Pierce |
| 2006/0106421 A1 | 5/2006 | Teoh |
| 2006/0116713 A1 | 6/2006 | Sepetka et al. |
| 2006/0135986 A1 | 6/2006 | Wallace et al. |
| 2006/0155324 A1 | 7/2006 | Porter et al. |
| 2006/0200234 A1 | 9/2006 | Hines |
| 2006/0276823 A1 | 12/2006 | Mitelberg |
| 2006/0276824 A1 | 12/2006 | Mitelberg |
| 2006/0276828 A1 | 12/2006 | Balgobin |
| 2006/0276829 A1 | 12/2006 | Balgobin |
| 2006/0276830 A1 | 12/2006 | Balgobin |
| 2006/0276831 A1 | 12/2006 | Porter et al. |
| 2006/0276832 A1 | 12/2006 | Balgobin |
| 2006/0276833 A1 | 12/2006 | Balgobin |
| 2006/0276834 A1 | 12/2006 | Balgobin |
| 2007/0010849 A1 | 1/2007 | Balgobin |
| 2007/0010850 A1 | 1/2007 | Balgobin |
| 2007/0016233 A1 | 1/2007 | Ferrera et al. |
| 2007/0078479 A1 | 4/2007 | Belenkaya |
| 2007/0118172 A1 | 5/2007 | Balgobin |
| 2007/0186933 A1 | 8/2007 | Domingo |
| 2007/0225634 A1 | 9/2007 | Ferren |
| 2007/0293932 A1 | 12/2007 | Zilla |
| 2008/0045997 A1 | 2/2008 | Balgobin et al. |
| 2008/0082176 A1 | 4/2008 | Slazas |
| 2008/0097508 A1 | 4/2008 | Jones |
| 2008/0109057 A1 | 5/2008 | Calabria |
| 2008/0119887 A1 | 5/2008 | Que |
| 2008/0140177 A1 | 6/2008 | Hines |
| 2008/0221703 A1 | 9/2008 | Que et al. |
| 2008/0269675 A1 | 10/2008 | Balgobin |
| 2008/0290554 A1 | 11/2008 | Wu et al. |
| 2008/0293932 A1 | 11/2008 | Wu et al. |
| 2008/0294237 A1 | 11/2008 | Chu |
| 2008/0300616 A1 | 12/2008 | Que et al. |
| 2009/0054988 A1 | 2/2009 | Hess |
| 2009/0112251 A1 | 4/2009 | Qian |
| 2009/0227976 A1 | 9/2009 | Calabria |
| 2009/0297582 A1 | 12/2009 | Meyer et al. |
| 2009/0318941 A1 | 12/2009 | Sepetka et al. |
| 2009/0318948 A1 | 12/2009 | Linder |
| 2010/0160946 A1* | 6/2010 | Mirizzi ............ A61B 17/12181 |
| | | 606/191 |
| 2010/0160953 A1 | 6/2010 | Ngo et al. |
| 2010/0268204 A1 | 10/2010 | Tieu |
| 2011/0125185 A1 | 5/2011 | Stopel |
| 2011/0295303 A1 | 12/2011 | Freudenthal |
| 2011/0313506 A1* | 12/2011 | Ray .................. A61B 17/12022 |
| | | 606/1 |
| 2012/0016376 A1 | 1/2012 | Adams et al. |
| 2012/0041472 A1 | 2/2012 | Tan |
| 2012/0158034 A1 | 6/2012 | Wilson |
| 2012/0283768 A1 | 11/2012 | Cox et al. |
| 2013/0072959 A1 | 3/2013 | Wu et al. |
| 2013/0116771 A1 | 5/2013 | Robinson |
| 2013/0123757 A1* | 5/2013 | Crisostomo ....... A61M 25/0074 |
| | | 606/1 |
| 2013/0138136 A1 | 5/2013 | Beckham |
| 2013/0197618 A1* | 8/2013 | Cage .................... A61B 50/30 |
| | | 53/436 |
| 2013/0245667 A1 | 9/2013 | Marchand et al. |
| 2013/0253572 A1 | 9/2013 | Molaei et al. |
| 2013/0261657 A1 | 10/2013 | Lorenzo |
| 2013/0296917 A1 | 11/2013 | Rees et al. |
| 2014/0052233 A1 | 2/2014 | Cox et al. |
| 2014/0058434 A1 | 2/2014 | Jones |
| 2014/0058436 A1 | 2/2014 | Rosenbluth et al. |
| 2014/0257363 A1 | 9/2014 | Lippert |
| 2014/0277099 A1 | 9/2014 | Wallace |
| 2014/0288588 A1 | 9/2014 | Lam |
| 2014/0330299 A1 | 11/2014 | Rosenbluth et al. |
| 2015/0057700 A1 | 2/2015 | Chen |
| 2015/0196304 A1 | 7/2015 | Rabkin et al. |
| 2015/0209050 A1 | 7/2015 | Aboytes et al. |
| 2015/0272589 A1 | 10/2015 | Lorenzo |
| 2015/0272590 A1 | 10/2015 | Aboytes et al. |
| 2015/0305867 A1* | 10/2015 | Liu ...................... A61F 2/2433 |
| | | 623/2.11 |
| 2015/0313605 A1 | 11/2015 | Griffin |

(56) References Cited

U.S. PATENT DOCUMENTS

| | | |
|---|---|---|
| 2015/0327976 A1 | 11/2015 | Divino et al. |
| 2015/0342613 A1 | 12/2015 | Aboytes et al. |
| 2016/0022445 A1 | 1/2016 | Ruvalcaba et al. |
| 2016/0206323 A1 | 7/2016 | Hebert et al. |
| 2016/0228123 A1 | 8/2016 | Anderson |
| 2016/0324528 A1 | 11/2016 | Hebert et al. |
| 2016/0324668 A1 | 11/2016 | Wallace et al. |
| 2017/0035430 A1 | 2/2017 | Sarge et al. |
| 2017/0035437 A1 | 2/2017 | Sarge et al. |
| 2017/0164951 A1 | 6/2017 | Divino et al. |
| 2017/0231789 A1 | 8/2017 | Cam et al. |
| 2018/0125501 A1 | 5/2018 | Aboytes et al. |
| 2018/0132859 A1 | 5/2018 | Aboytes et al. |
| 2018/0214159 A1 | 8/2018 | Zhang et al. |
| 2018/0221030 A1 | 8/2018 | Nita et al. |
| 2018/0289375 A1 | 10/2018 | Hebert et al. |
| 2018/0317933 A1 | 11/2018 | Nita et al. |
| 2019/0015227 A1 | 1/2019 | Wallace |
| 2019/0046211 A1 | 2/2019 | Bronikowski et al. |
| 2019/0201000 A1 | 7/2019 | Wallace et al. |
| 2019/0231362 A1 | 8/2019 | Maitland et al. |
| 2019/0314033 A1 | 10/2019 | Mirigian et al. |
| 2019/0374227 A1 | 12/2019 | Johnson et al. |
| 2019/0374228 A1 | 12/2019 | Wallace et al. |
| 2019/0374232 A1 | 12/2019 | Lorenzo |
| 2020/0000477 A1 | 1/2020 | Nita et al. |
| 2020/0038031 A1 | 2/2020 | Gorochow |

FOREIGN PATENT DOCUMENTS

| | | |
|---|---|---|
| EP | 2520251 | 5/2011 |
| EP | 3 247 285 | 11/2017 |
| JP | 2016-508850 | 3/2016 |
| WO | WO 94/09705 | 5/1994 |
| WO | WO 03/037191 | 5/2003 |
| WO | WO 2004/004580 | 1/2004 |
| WO | WO 2004/010878 | 2/2004 |
| WO | WO 2004/069059 | 8/2004 |
| WO | WO 2006/034149 | 3/2006 |
| WO | WO 2006/088531 | 8/2006 |
| WO | WO 2007/033093 | 3/2007 |
| WO | WO 2010/000079 | 1/2010 |
| WO | WO 2012/135859 | 10/2012 |
| WO | WO 2013/119332 | 8/2013 |
| WO | WO 2014/138580 | 9/2014 |
| WO | WO 2016/034149 | 3/2016 |
| WO | WO 2016/044188 | 3/2016 |
| WO | WO 2017/041554 | 3/2017 |
| WO | WO 2017/044982 | 3/2017 |
| WO | WO 2017/096188 | 6/2017 |
| WO | WO 2017/106265 | 6/2017 |
| WO | WO 2018/022954 | 2/2018 |
| WO | WO 2018/051187 | 3/2018 |
| WO | WO 2018/053314 | 3/2018 |
| WO | WO 2018/156833 | 8/2018 |
| WO | WO 2019/033978 | 2/2019 |

OTHER PUBLICATIONS

Examination Report for European Application No. 18728769.3 dated Mar. 1, 2022.
International Search Report and Written Opinion dated May 3, 2016 for International Application No. PCT/US2016/013638.
International Search Report and Written Opinion dated May 22, 2020 for International Application No. PCT/US2020/012361.
Aug. 13, 2018 Communication Relating to the Results of the Partial International Search from PCT/US2018/030033.

\* cited by examiner

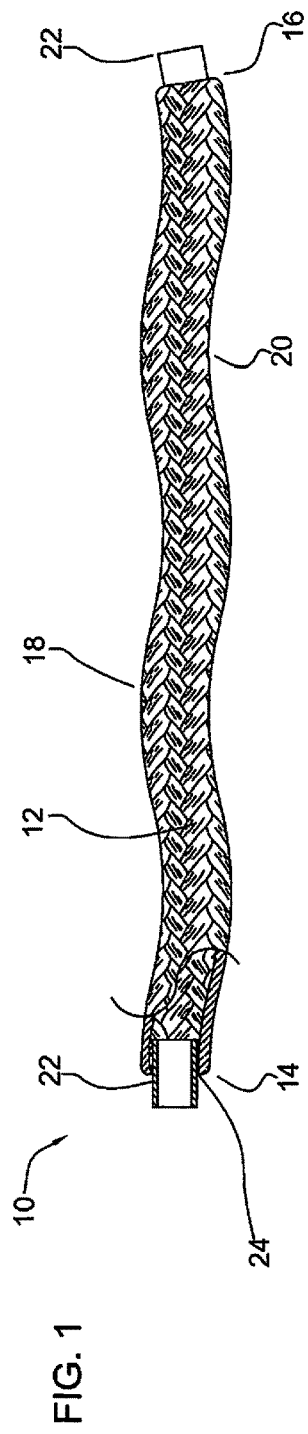
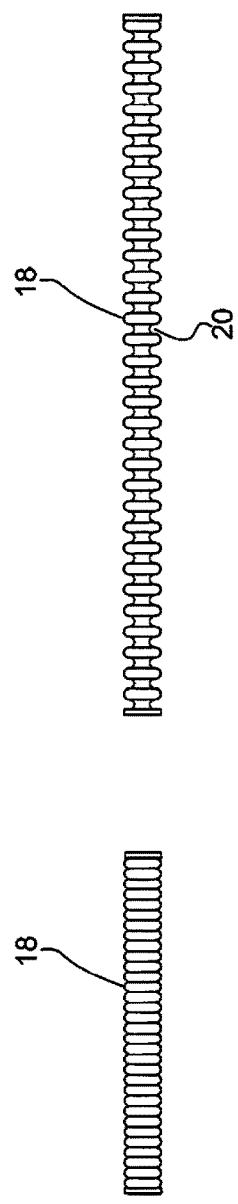
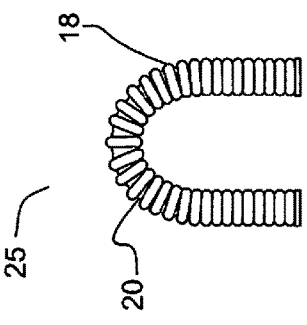
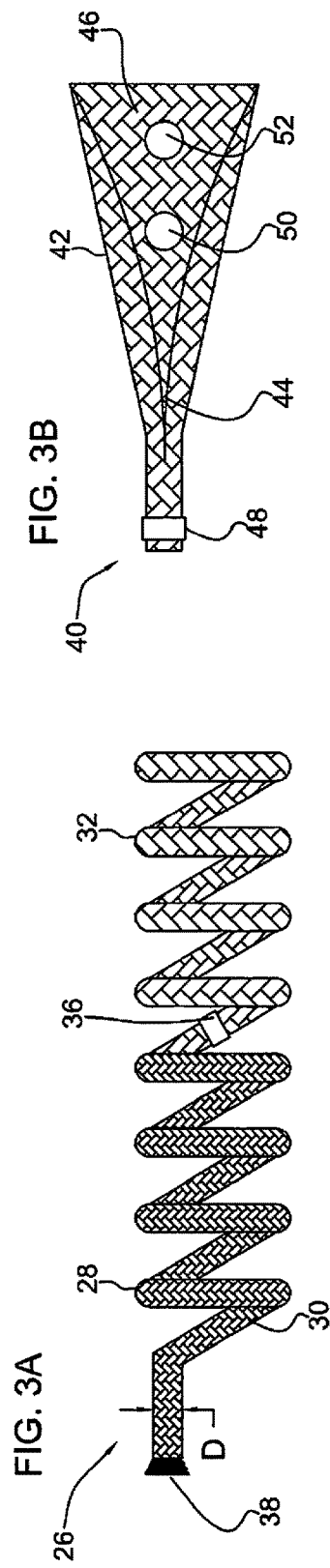
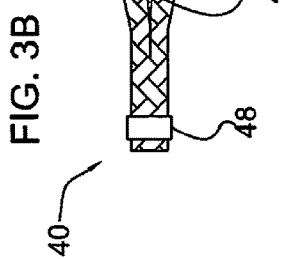

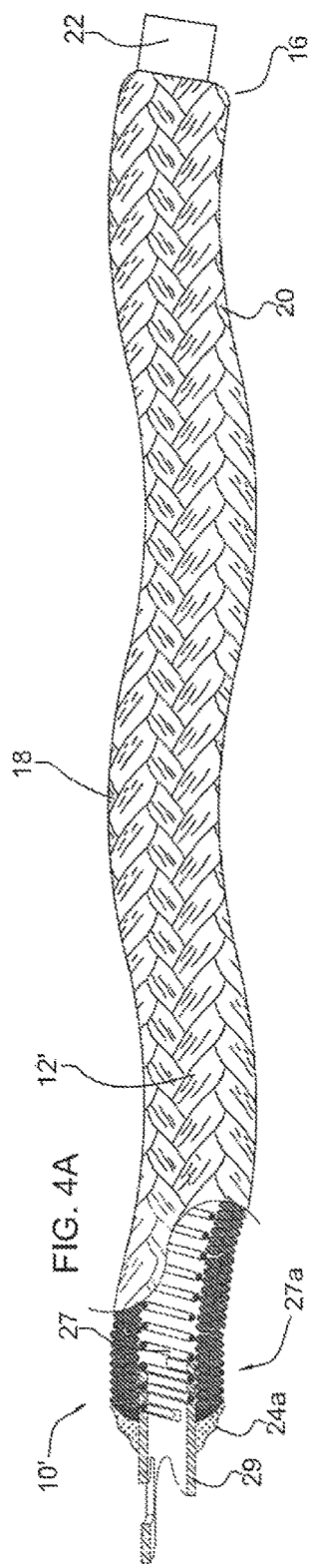
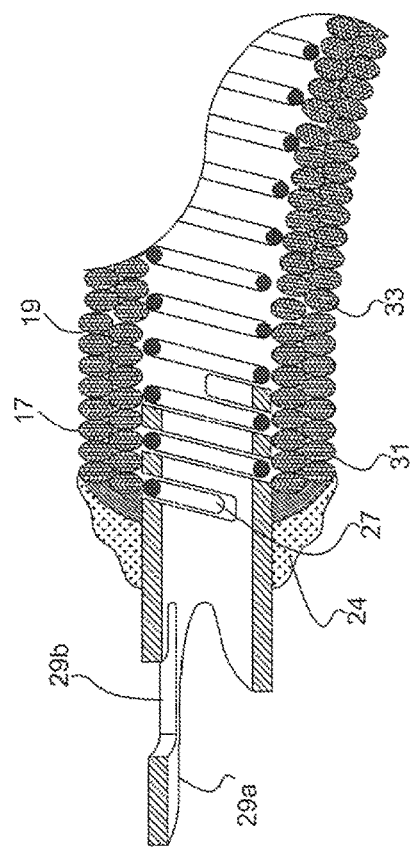
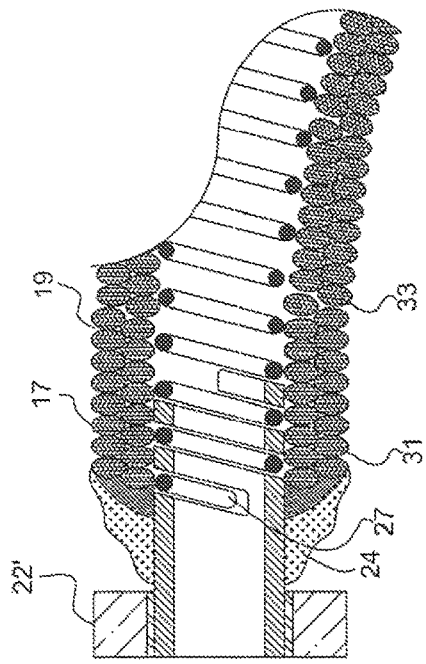
FIG. 4A
FIG. 4B
FIG. 4C

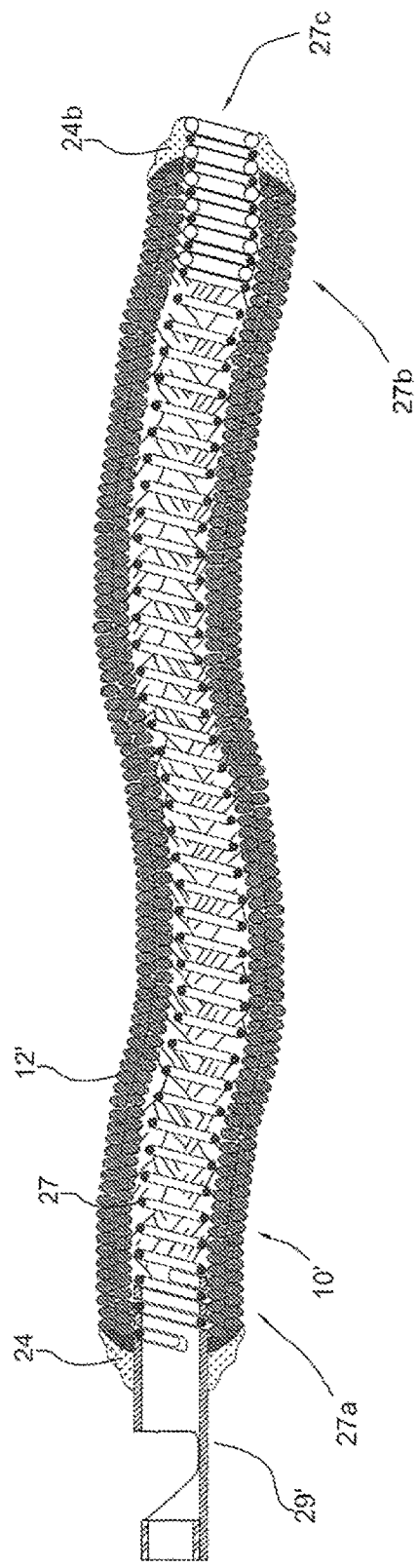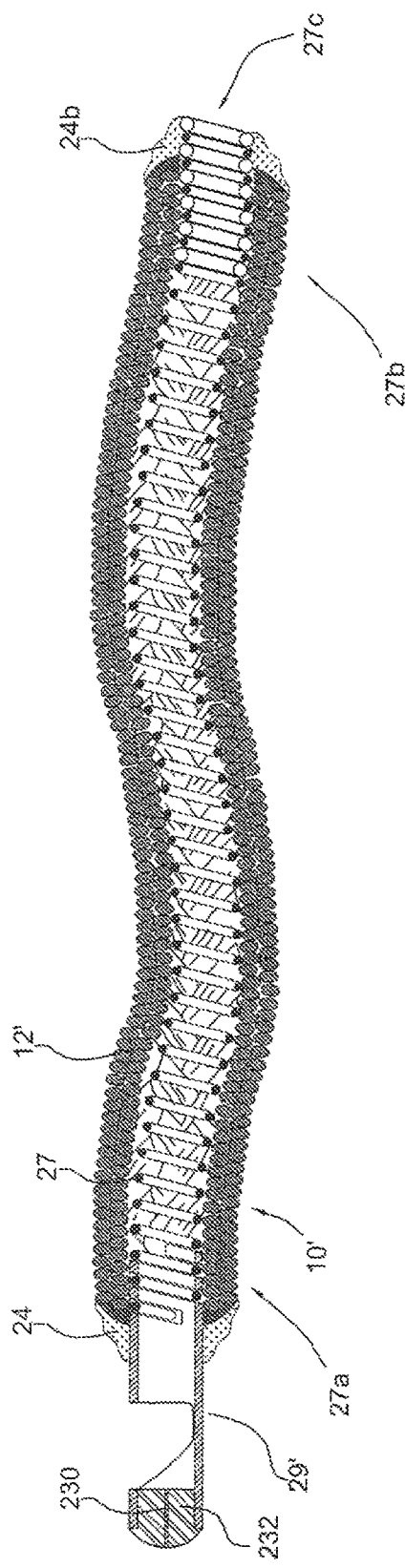

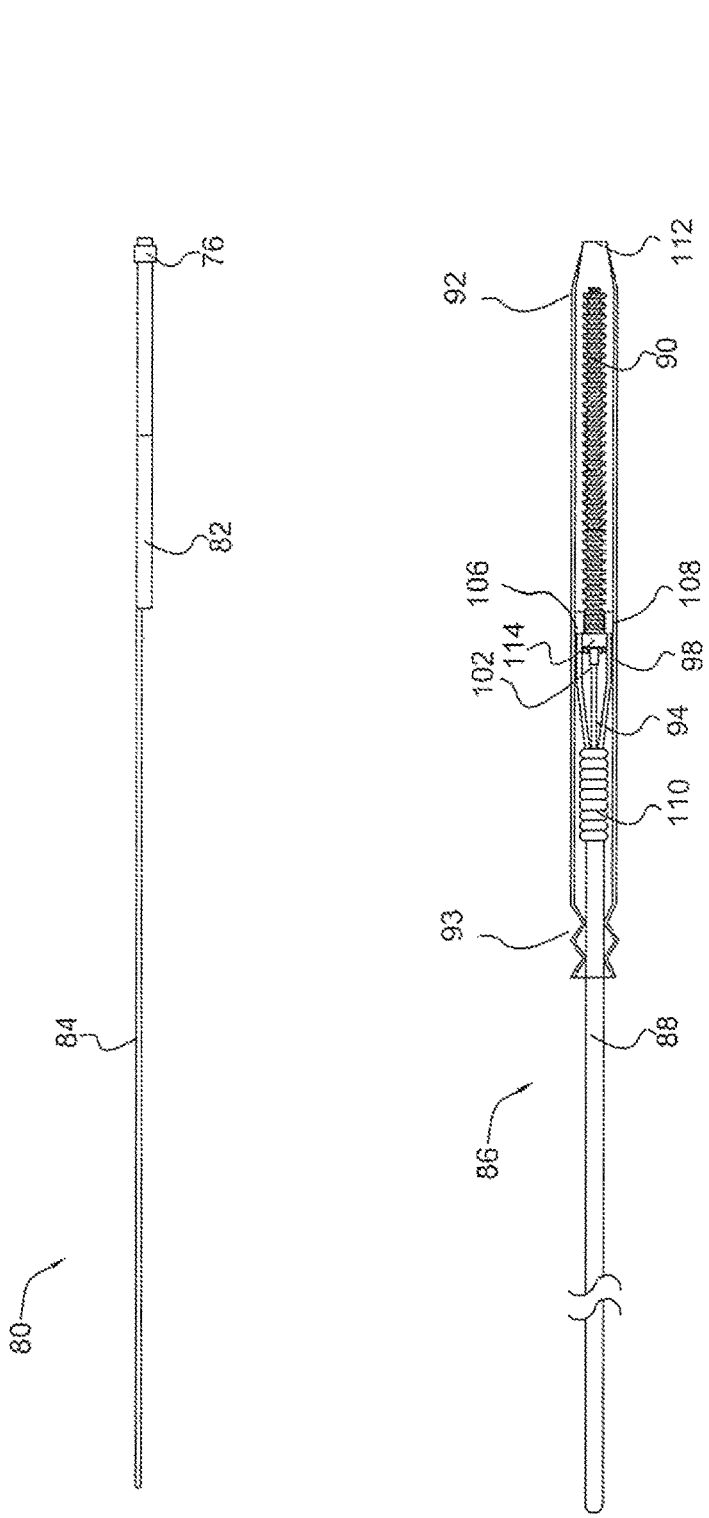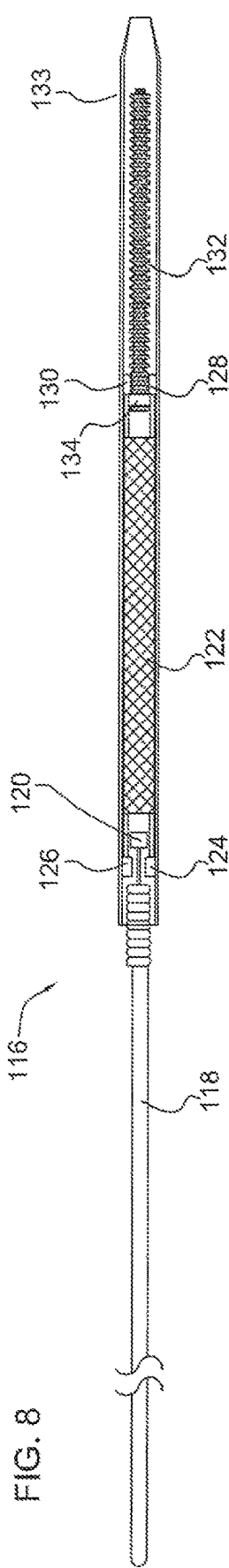
FIG. 6
FIG. 7
FIG. 8

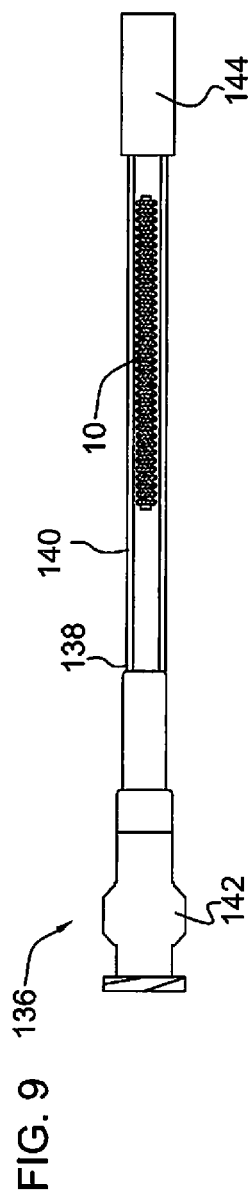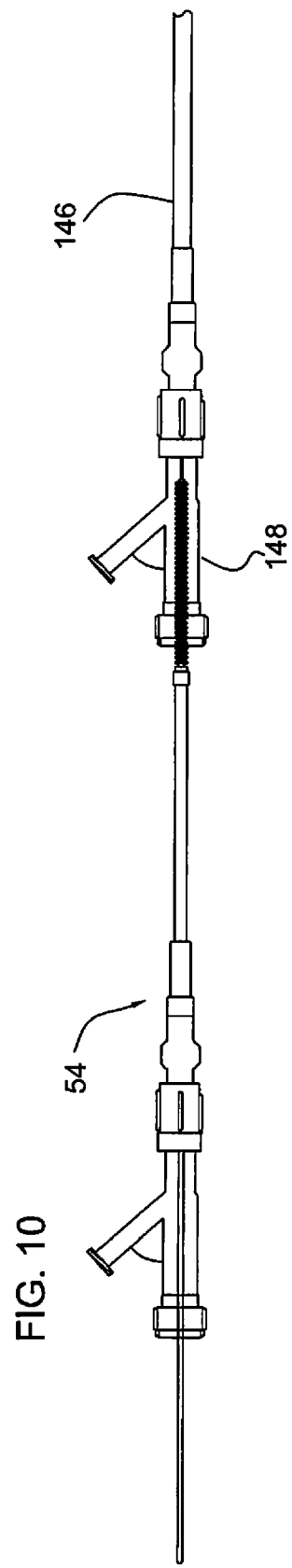

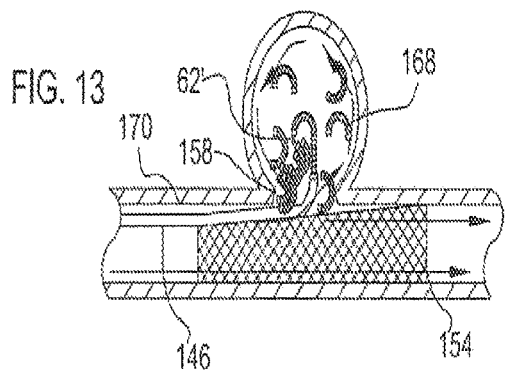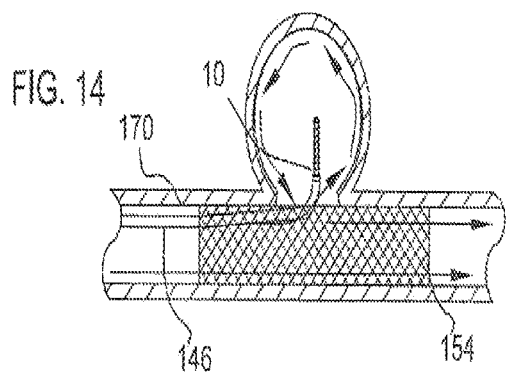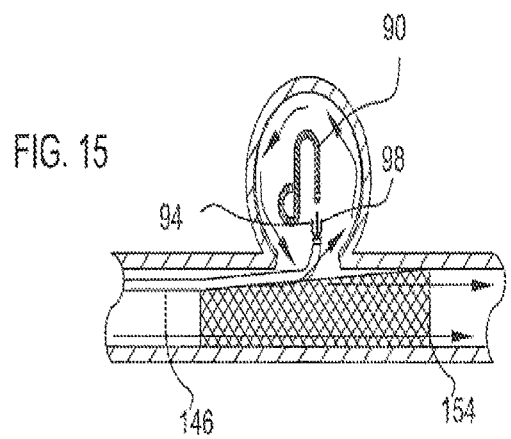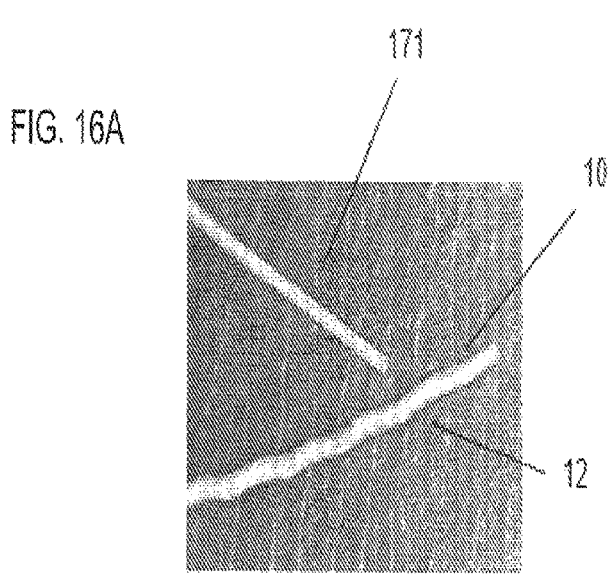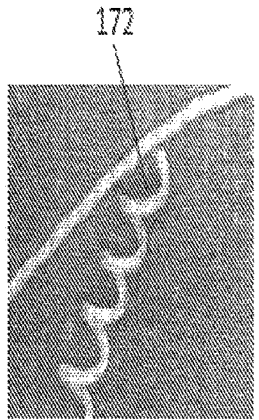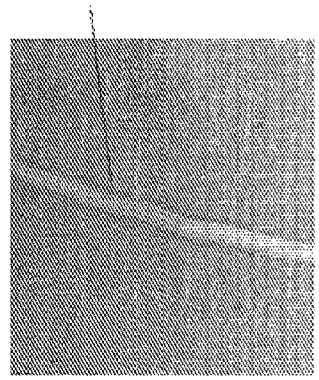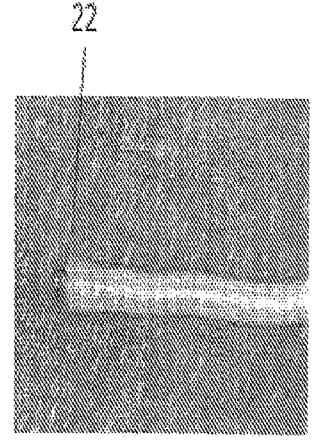

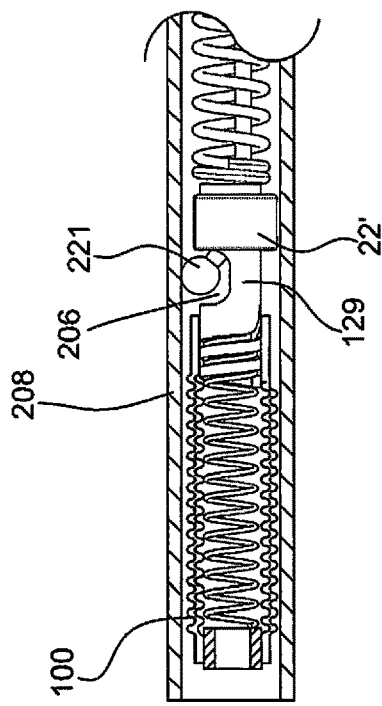
FIG. 23B
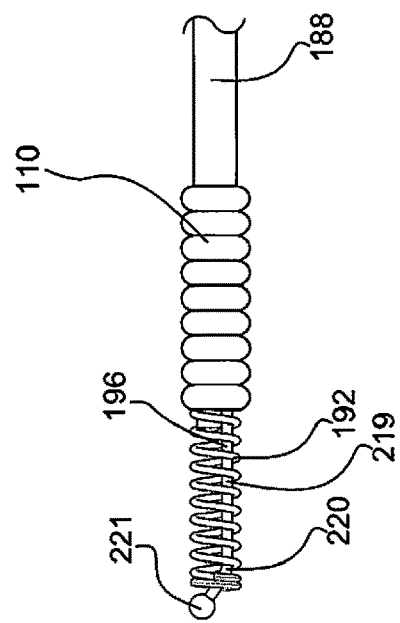
FIG. 23A
FIG. 24
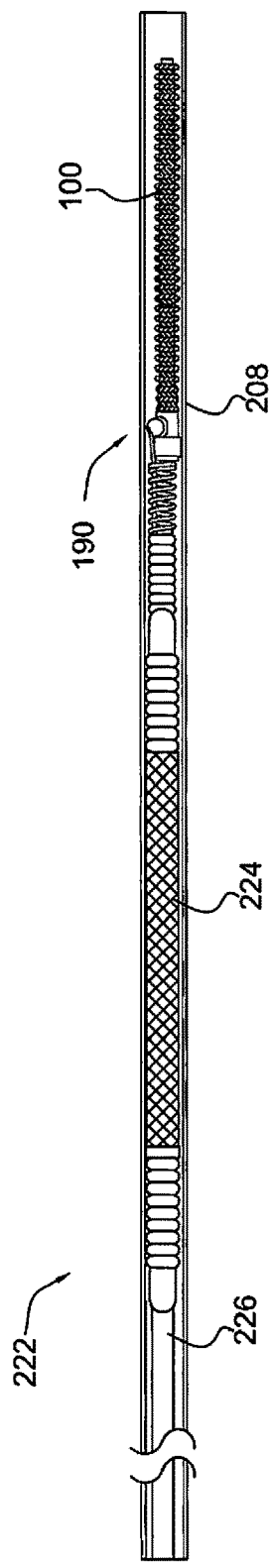

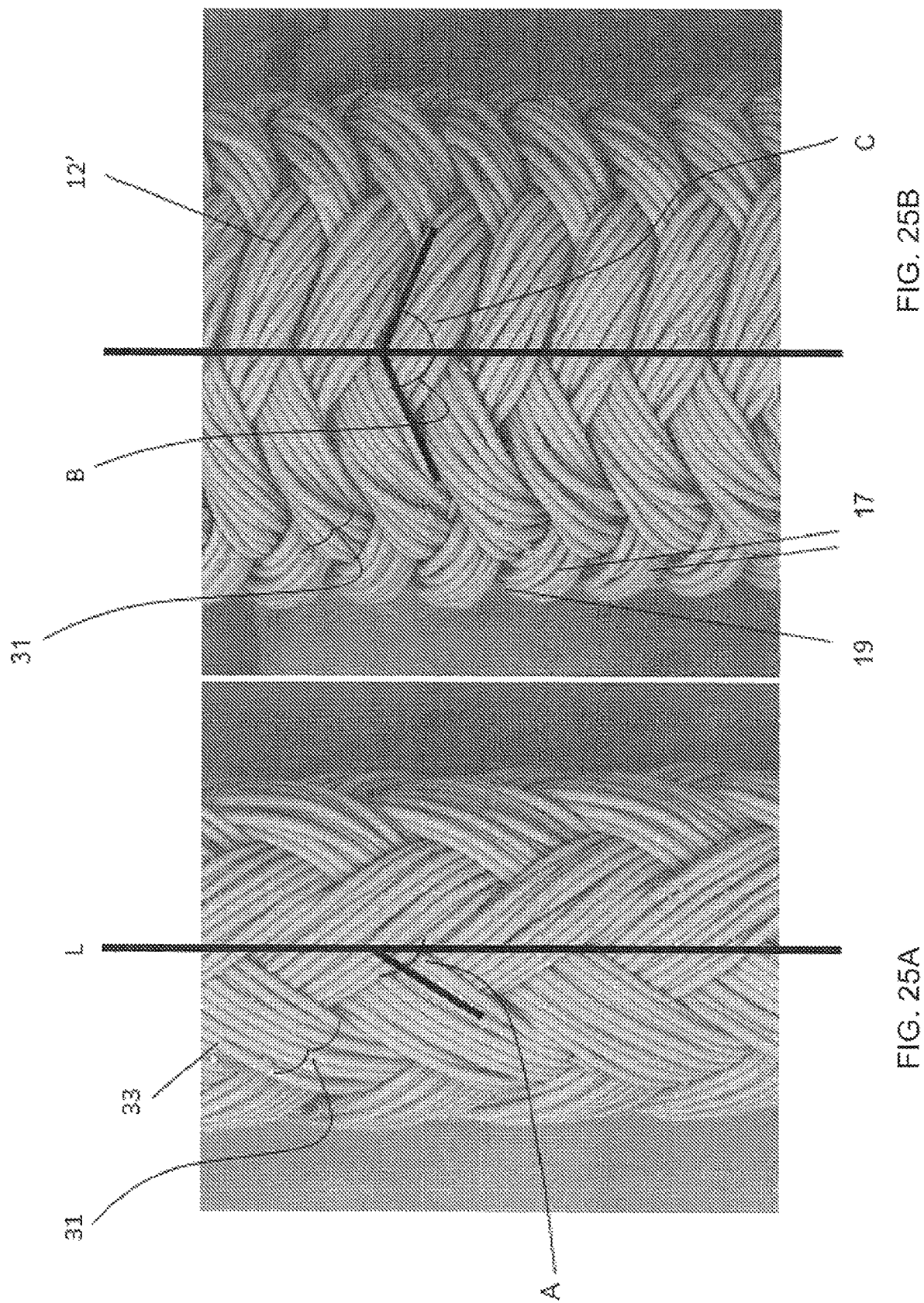

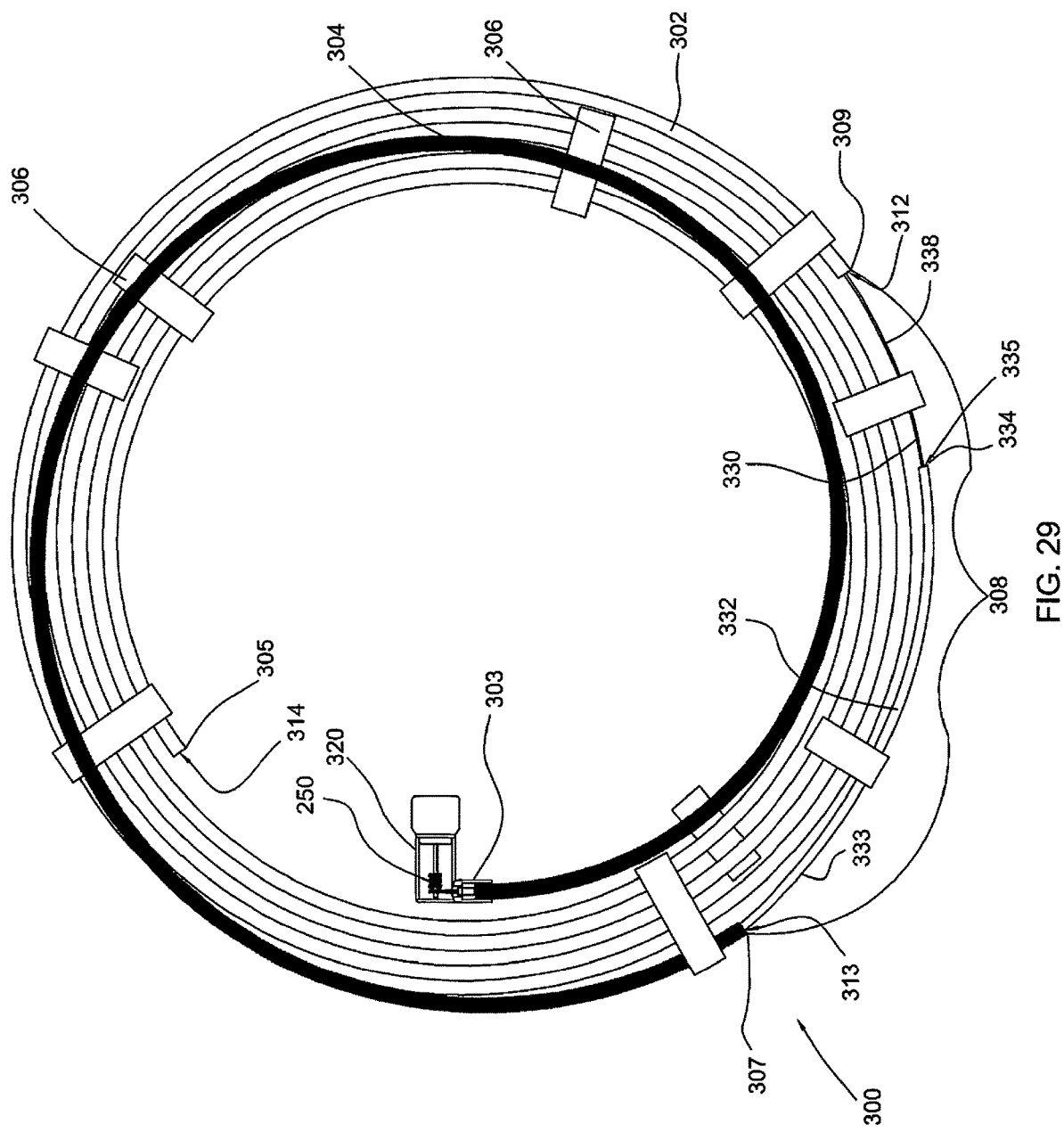

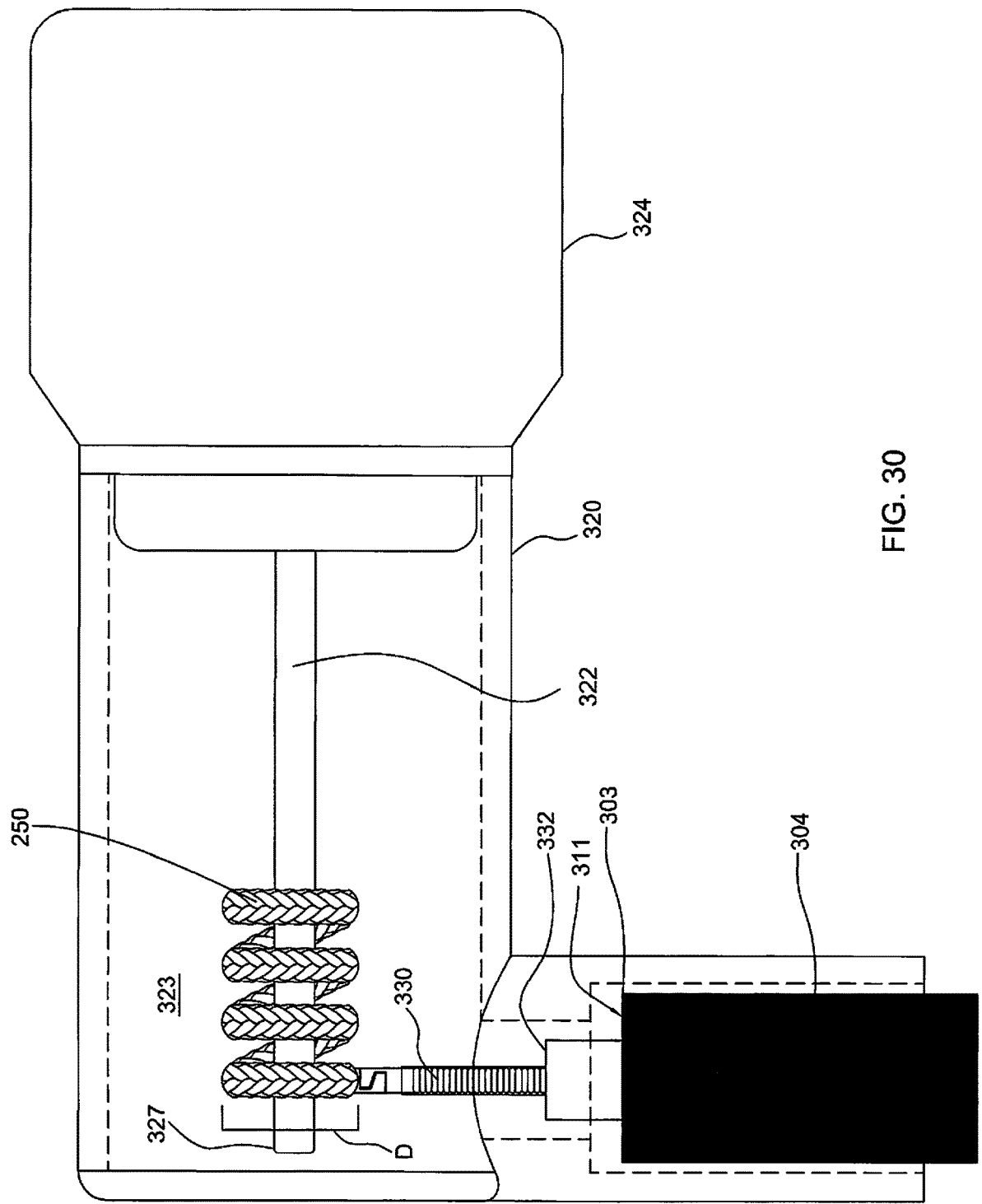

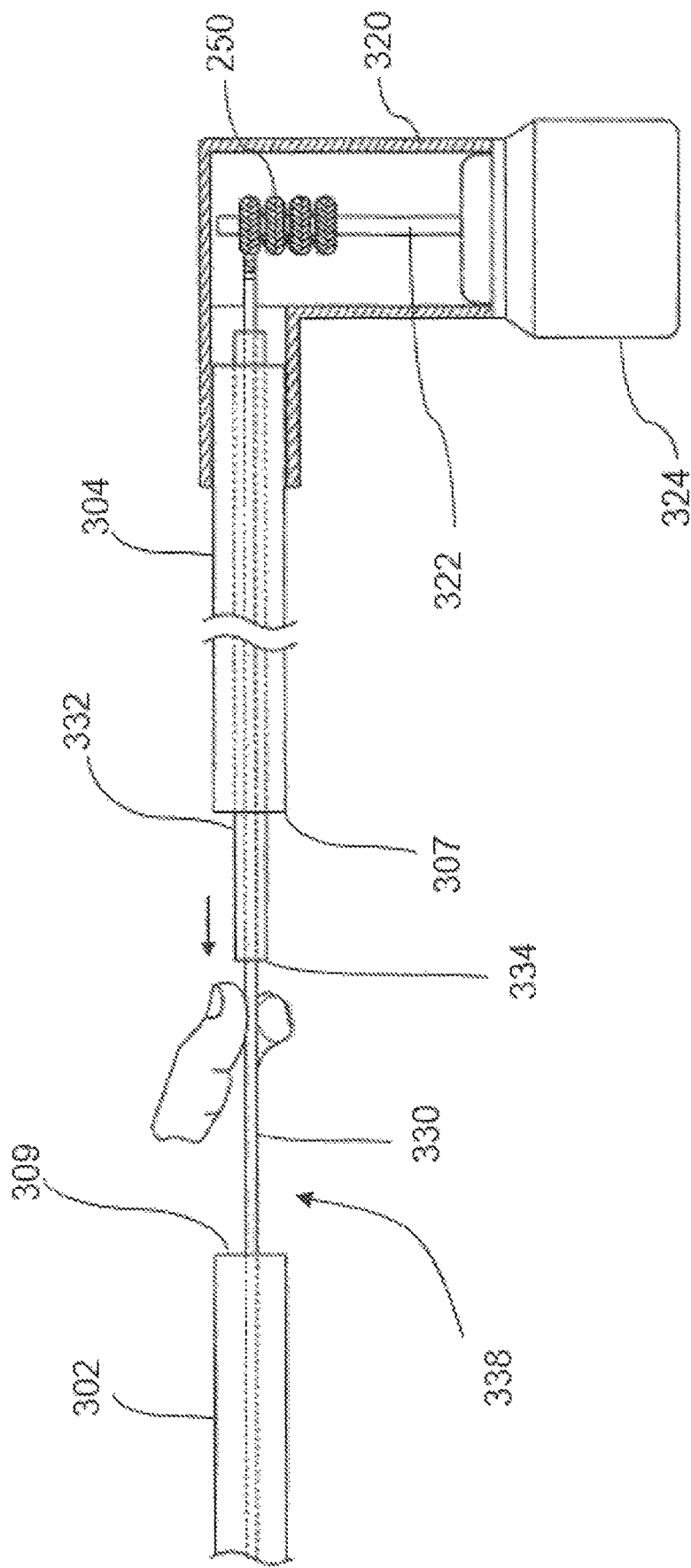

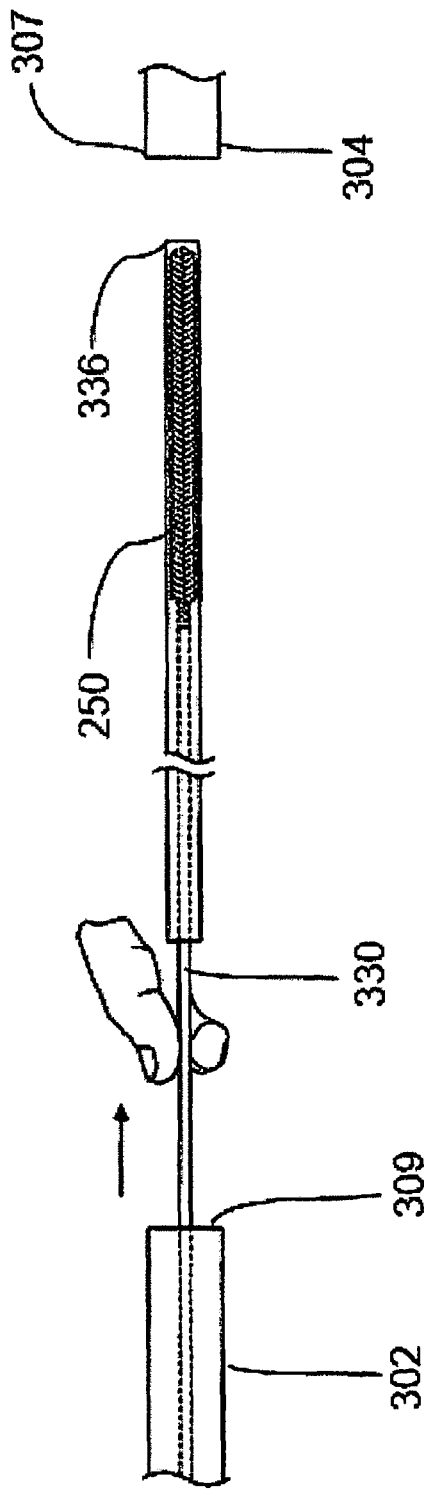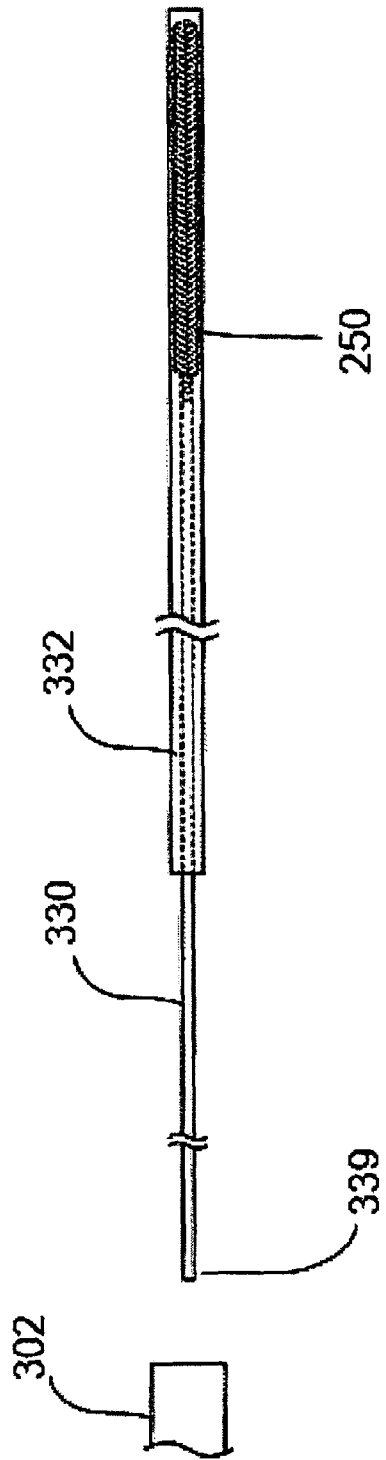
FIG. 35
FIG. 36

PACKAGING FOR SURGICAL IMPLANT

This application is a divisional of application Ser. No. 15/953,261, filed Apr. 13. 2018, which is a continuation in part of application Ser. No. 14/997,094, filed Jan. 15, 2016, now U.S. Pat. No. 9,962,146 which claims priority from provisional application Ser. No. 62/105,648, filed Jan. 20, 2015, and claims priority from provisional application Ser. No. 62/502,663, filed May 6, 2017 and from from provisional application Ser. No. 62/622,869, filed Jan. 27, 2018. The entire contents of each of these applications are incorporated herein by reference.

BACKGROUND

Technical Field

This application relates to packaging for surgical implants. This application also relates to delivery systems for surgical implants.

Background of Related Art

An aneurysm is a localized, blood filled balloon-like bulge that can occur in the wall of any blood vessel, as well as within the heart. There are various treatments for aneurysms. One endovascular treatment option for aneurysms is complete reconstruction of the damaged vessel using a vascular prosthesis or stent-graft. A stent-graft is an implantable tubular structure composed of two parts, a stent and a graft. The stent is a mesh-like structure made of metal or alloy which functions as a scaffold to support the graft. The graft is typically a synthetic fabric that is impervious to blood flow and lines the stent. Stent-grafts are not a treatment option for intracranial aneurysms due to the risk of cutting off blood flow to feeder vessels that may be vital for brain function. Stent-grafts can also be stiff, hard to deliver/retract, and can be highly thrombogenic within the parent vessel, all of which are undesirable features for intracranial aneurysm treatment. As a result, endovascular treatment of intracranial aneurysms has centered on packing or filling an aneurysm with material or devices in order to achieve a high packing density to eliminate circulation of blood, which leads to thrombus formation and aneurysm closure over time.

There have been a variety of materials and devices described for filling the sac of an intracranial aneurysm such as injectable fluids, microfibrillar collagen, polymeric foams and beads. Polymeric resins such as cyanoacrylate have also been used. Both are typically mixed with a radiopaque resin to aid in visualization. These materials pose a significant risk due to the difficulty of controlling dispersion and in retrieving them, if improperly or excessively delivered.

Mechanical vaso-occlusive devices are another option for filling an aneurysm. One type of mechanical vaso-occlusive device for the placement in the sac of the aneurysm is a balloon. Balloons are carried to the vessel site at the end of a catheter and inflated with a suitable fluid, such as a polymerizable resin, and released from the catheter. The main advantage of the balloon is its ability to effectively fill the aneurysm sac. However, a balloon is difficult to retrieve, cannot be visualized unless filled with contrast, has the possibility of rupture, and does not conform to varying aneurysm shapes.

Other types of mechanical vaso-occlusive devices are composed of metals or alloys, and biocompatible fibers, for example. Generally, the materials are formed into tubular structures such as helical coils. One of the earliest fibered coils was the Gianturco coil (Cook Medical). This coil was formed from a 5 cm length of 0.036" guidewire (inner core removed) and featured four 2 inch strands of wool attached to one tip of the coil to promote thrombosis. This device was difficult to introduce into tortuous vessel sites less than 3 mm in diameter. This is generally because the coil was stiff or bulky and had a high coefficient of friction.

Chee et al. (U.S. Pat. No. 5,226,911) introduced a more deliverable fibered coil with fibers that were directly attached to the length of the coil body. This coil was designed for more tortuous anatomy by decreasing the amount of thrombogenic material being delivered with the coil. Other examples of coils are U.S. Pat. No. 4,994,069 to Ritchart et al.; U.S. Pat. No. 5,354,295 and its parent, U.S. Pat. No. 5,122,136, both to Guglielmi et al.

Materials can also be formed into tubes/strings/braided sutures (see, e.g., U.S. Pat. No. 6,312,421 to Boock; U.S. patent application Ser. No. 11/229,044 to Sepetka et al.; U.S. patent application Ser. No. 13/887,777 to Rees; U.S. patent application Ser. Nos. 13/552,616 and 10/593,023 both to Wu et al.), cables (see, e.g., U.S. Pat. No. 6,306,153 to Kurz et al.), or braids. Metal coils can also be covered by winding on thrombogenic fiber as described in U.S. patent application Ser. No. 12/673,770 to Freudenthal and U.S. Pat. No. 6,280,457 to Wallace et al.

Unlike other tubular structures, braided or polymer coils can be further divided into non-expandable and self-expandable devices. These devices can be made from materials such as textiles, polymers, metal or composites using known weaving, knitting, and braiding techniques and equipment. Included in the weave or the finished braid can be optional mono or multifilament fiber manufactured to impart additional features or effects (e.g., radiopacity and thrombogenicity).

Non-expandable braids (see, e.g. U.S. Pat. No. 5,690,666 to Berenstein et al.; U.S. Pat. No. 5,423,849 to Engelson et al.; and U.S. Pat. No. 5,964,797 to Ho) can act as the implant and be mainly metallic, polymer, or a combination of metal and polymer. In such designs, braids have some minimal space between the filaments (braid strands) resulting in open cell designs. In addition, tight, mostly metal braids employing such designs result in stiff structures which are difficult to track via catheter or risk injury to the vasculature. Also, metal braided structures may be rough to the touch if not covered or further processed.

These braids can be formed into secondary shapes, such as coils that have little or no inherent secondary shape, they can be dimensioned to engage the walls of the aneurysm, or they can have other shapes (e.g. random, "flower", or three dimensional). These structures can also have a fiber bundle (s) in, or protruding from, the interior core made of natural fibers or thermoplastics infused with drugs to help with clotting (see, e.g., U.S. Pat. No. 5,423,849 to Engelson et al.; and U.S. Pat. No. 5,645,558 to Horton). Coiled braids can also be supplied with bio-active or other surface coatings (see, e.g., U.S. Pat. No. 6,299,627 to Eder et al.).

Non-expandable braids can also cover core or primary structures, such as coils or other braids (see, e.g., U.S. Pat. No. 5,382,259 to Phelps et al.; U.S. Pat. No. 5,690,666 to Berenstein et al.; U.S. Pat. No. 5,935,145 to Villar et al.; and U.S. Pat. No. 8,002,789 to Ramzipoor et al.). Much like the above braid structures, these covers have open cell designs (e.g., inner coil structure is visible through the braid).

Regardless of configuration, it is difficult to achieve high packing densities and rapid flow stagnation with these devices as they have open cell construction which allows at least some blood flow through the wall, may not compress adequately, and/or may have limited bend radii. If an aneurysm sac is not sufficiently packed to stop or slow blood flow, any flow through the neck of the aneurysm may prevent stasis or cause coil compaction, leading to recanalization of the aneurysm. Conversely, tight packing of metal coils in large or giant aneurysms may cause increased mass effect (compression of nearby tissue and stretching of aneurysm sac) on adjacent brain parenchyma and cranial nerves. Coil prolapse or migration into parent vessels is another possible issue with non-expanding devices, especially in wide neck aneurysms.

Braids may also be self-expanding and can be shaped into various forms such as a ball, a coil(s), and a combination braid-stent. Examples of self-expanding devices are disclosed in the following: U.S. Pat. No. 8,142,456 to Rosqueta et al.; U.S. Pat. No. 8,361,138 to Adams; U.S. patent application Ser. No. 13/727,029 to Aboytes et al.; U.S. patent application Ser. No. 14/289,567 to Wallace et al.; U.S. patent application Ser. No. 13/771,632 to Marchand et al.; and U.S. patent application Ser. No. 11/148,601 to Greenhalgh.

Self-expanding braids are expected to occupy all or substantially all of the volume of an aneurysm to obstruct flow and/or promote endothelization at the neck. A major problem for these designs is sizing. The implant has to be accurately sized so that upon expansion it occupies enough volume to fill the entire aneurysm, dome to neck. Undersized devices lead to insufficient packing as described above, whereas oversizing risks rupturing the aneurysm or blockage of parent vessel.

Neck bridges are yet another approach to treating intracranial aneurysms. They can be broken down into two categories: those that act as support to keep the coil mass from migrating into a parent vessel (coil retainer) and those that span the neck to obstruct flow into the aneurysm. Neck bridges that support the coil mass tend to be petal/flower shaped and span the neck of the aneurysm or placed between the parent vessel and aneurysm sac. Examples of neck bridges for supporting the coil mass are disclosed in the following: U.S. Pat. No. 6,193,708 to Ken et al.; U.S. Pat. No. 5,935,148 to Villar et al.; U.S. Pat. No. 7,410,482 to Murphy et al.; U.S. Pat. No. 6,063,070 to Eder; U.S. patent application Ser. No. 10/990,163 to Teoh; and U.S. Pat. No. 6,802,851 to Jones et al.

Neck bridges that obstruct flow through the aneurysm neck can be deployed either internal or external to the aneurysm and may not require deployment of embolization coils. Examples of intra-aneurysmal neck bridges with deployment at the base of the aneurysm sac with components extending into the neck are disclosed in U.S. Pat. No. 6,454,780 to Wallace; U.S. Pat. No. 7,083,632 to Avellanet et al.; U.S. Pat. No. 8,292,914 to Morsi; and U.S. Pat. No. 8,545,530 to Eskridge et al. Examples of neck bridges deployed external to the aneurysm (in the parent vessel) are disclosed in U.S. Pat. No. 6,309,367 to Boock; U.S. Pat. No. 7,241,301 to Thramann et al.; and U.S. Pat. No. 7,232,461 to Ramer; U.S. Pat. No. 7,572,288 to Cox; U.S. patent application Ser. No. 11/366,082 to Hines; U.S. patent application Ser. No. 14/044,349 to Cox et al.; U.S. Pat. No. 8,715,312 to Burke; U.S. Pat. No. 8,425,548 to Connor; and U.S. Pat. No. 8,470,013 to Duggal et al. Neck bridges can also have surface treatment to encourage neointima formation as disclosed in U.S. Pat. No. 6,626,928 to Raymond et al. Regardless of design, neck bridges pose several problems when treating intracranial aneurysms. The first major challenge is deployment of these devices, which requires the bridge to be maneuvered and often re-positioned over the aneurysm neck to assure complete coverage. Secondly, if recanalization occurs, any subsequent retreatment of the aneurysm will be hampered due to access being restricted by the neck bridge or one of its components.

Stents and flow diverters are similar to neck bridges in function, but are intended for parent vessel reconstruction and therefore run distal to proximal of the aneurysm, covering the neck. Such devices are deployed in the parent vessel and are intended to act as a physical blood flow barrier to induce sac embolization, stabilize embolic coils, and prevent coil protrusion and/or migration. Flow diverters, due to their relative low porosity (high coverage), can be used with or without coils and have been found to promote thrombus formation by restricting blood flow into the aneurysm sac. However, complications such as recanalization, delayed stent thrombosis, delayed aneurysm rupture, and stent migration have also been observed. An example of a stent is disclosed in U.S. Pat. No. 6,746,475 to Rivelli and a flow diverter is disclosed in U.S. Pat. No. 8,398,701 to Berez et al.

While the above methods attempt to treat intracranial aneurysms with minimally invasive techniques, there remains a need for a highly compliant and thrombogenic filler that blocks blood flow within the sac of the aneurysm without the drawbacks of current devices. For example, it would be advantageous to provide a device that achieves sufficient flexibility to enable advancement through the tortuous vasculature into the cerebral vasculature and achieves high packing densities while maintaining a high concentration of thrombogenic material. It would also be advantageous to provide a device that causes rapid clotting of the blood. It would also be advantageous to provide a device that promotes tissue ingrowth within a relatively short period of time. Further, it would be advantageous to provide a device that is soft, compressible and absorbent to retain blood. Achieving all these objectives without favoring/emphasizing one at the expense of another presents a difficult challenge. This is compounded by the desire to provide such device which is simple in structure and simple to manufacture without sacrificing efficacy. Further compounding the challenge is the fact that since the device is designed for minimally invasive insertion, it needs to be easy to deliver and deploy at the intracranial site as well as manufacturable in a small enough size for use in cerebral vasculature. That is, all of the above needs to be achieved with a construction that effectively packs the aneurysm without damaging the sac or other tissue while promoting rapid clotting and healing of an intracranial aneurysm with reduction in mass effect. To date, no device effectively achieves all these objectives, with current devices at best achieving one objective at the expense of the others.

In addition, it would be advantageous to provide a delivery system for such device that is sufficiently low profile and flexible to atraumatically advance through the vasculature and designed to securely retain the device during advancement through the vasculature. Such delivery systems would need to account for the preset non-linear form of the implant. It would be also be advantageous to provide such delivery system which enables retrieval of the device after partial delivery to the target site to enable repositioning or withdrawal of the device. That is, it is desirable to maintain a secure lock of the device during delivery as well as be able to retrieve the device after partial delivery, i.e., before it is fully deployed. Such delivery devices have uses in a variety of clinical applications.

SUMMARY OF INVENTION

The present invention overcomes the problems and deficiencies of the prior art. In accordance with one aspect of the present invention, a packaging for a vascular implant is provided comprising a first packaging tube and a container. The implant is positioned within the container in a first condition, wherein the implant is movable from the container into the first packaging tube and maintained within the first packaging tube in a second condition. The implant has a first transverse dimension in the first condition and a second transverse dimension in the second condition, the second transverse dimension being less than the first transverse dimension.

In some embodiments, the packaging further includes a delivery sheath having a lumen and a delivery member positioned within the lumen, the delivery sheath positioned within the first packaging tube, and the implant is pulled into the delivery sheath by the delivery member to be maintained in the second condition within the delivery sheath within the first packaging tube. In some embodiments, the first transverse dimension of the implant is greater than a transverse dimension of the lumen of the delivery sheath.

In some embodiments, a second packaging tube is provided having a first end and a second opposite end, and the first packaging tube has a first end adjacent the container and a second opposite end, wherein the first end of the second packaging tube is spaced from the second end of the first packaging tube to form a gap between the first and second packaging tubes. In some embodiments, the second packaging tube has a length greater than a length of the first packaging tube.

In some embodiments, a support member is provided within the container, wherein the support member comprises an elongated member over which the implant is positioned in a non-linear configuration.

In accordance with another aspect, the present invention provides the combination of a packaging and a vascular implant delivery system comprising a container having a receiving space, a first packaging tube having an opening in communication with the receiving space, a first end adjacent the receiving space, a second opposite end and a lumen. A delivery sheath is positioned within the lumen of the first packaging tube. An elongated delivery member is positioned within a lumen of the delivery sheath for moving the vascular implant within the lumen of the delivery sheath and a vascular implant is supported within the container. The delivery member extends through the first packaging tube and extends outside the second end of the first packaging tube to provide an exposed portion of the delivery member for grasping by a clinician.

In some embodiments, the delivery sheath has a portion extending outside the second end of the first packaging tube to provide an exposed portion of the delivery sheath for grasping by a clinician. In some embodiments, the exposed portion of the delivery member extends outside the exposed portion of the delivery sheath.

In some embodiments, the system further includes a second packaging tube, a first end of the second packaging tube is spaced from the second end of the first packaging tube to create a gap between the first and second packaging tubes, wherein the exposed portion of the delivery member and the exposed portion of the delivery sheath are exposed within the gap between the first and second packaging tubes. In some embodiments, the delivery member extends into the second packaging tube and a proximal end of the delivery sheath terminates in the gap between the first and second packaging tubes.

In some embodiments, application of a pulling force to the delivery member relative to the delivery sheath pulls the vascular implant from the container where it is held in an unconstrained condition into the delivery sheath so the vascular implant has a reduced transverse dimension. In some embodiments, the vascular implant is initially in a position substantially transverse to an opening in a first end of the delivery sheath.

In accordance with another aspect of the present invention, a method for removing a vascular implant from a packaging is provided, the packaging having a container to receive the implant and a first packaging tube, the method comprising the steps of:

a) pulling an elongated delivery member in a first direction to pull the vascular implant into a delivery sheath positioned within the first packaging tube;

b) subsequently pulling the delivery sheath in the first direction until a first end of the delivery sheath is free of the first packaging tube; and c) subsequently pulling the delivery member in a second direction opposite the first direction until a second end of the delivery member is free of a second packaging tube.

In some embodiments, the step of pulling the delivery member to pull the implant into the delivery sheath moves the implant to a more constrained condition having a smaller transverse dimension and prior to pulling the implant into the delivery sheath the implant has a transverse dimension larger than a transverse dimension of the delivery sheath. In some embodiments, the step of pulling the delivery sheath in the first direction includes also pulling the delivery member in the first direction.

In some embodiments one or both of the first and second packaging tubes are contained in a coiled configuration during shipping.

In some embodiments, a portion of the delivery member and delivery sheath are exposed in a gap between the first and second packaging tubes.

The present invention also provides delivery systems for vascular implants, e.g., an intra-aneurysmal micrograft, that overcomes the above discussed limitations and deficiencies in treating aneurysms, especially intracranial aneurysms.

In accordance with one aspect of the present invention, a system for delivering a vascular implant into a body lumen of a patient is provided comprising a vascular implant having a first engagement portion at a proximal portion, an elongated delivery member having a second engagement portion at a distal portion and releasably engageable with the first engagement portion of the implant, and an elongated member extending through the delivery member. The elongated member has an extended position and a retracted position, wherein in the extended position the elongated member extends into at least a portion of the implant to prevent release of the implant from the delivery member and in the retracted position the elongated member enables release of the implant from the delivery member.

In some embodiments, the implant includes a tube at a proximal end, and the tube includes the first engagement portion.

In some embodiments, the delivery member and the tube each have an eyelet through which the elongated member passes to maintain coupling of the delivery member and implant. A first radiopaque marker band can be positioned in the tube and a second radiopaque marker band can be positioned in the delivery member, the elongated member extending through the first and second marker bands in the extended position. In some embodiments, the marker bands form the eyelets; in alternate emboidments the tube does not have a marker band but is formed with a continuous circular circumferences to form the eyelet.

In some embodiments, one or both of the first and second engagement portions has a cam surface. In some embodiments, the second engagement portion of the delivery member includes a cradle and a cutout and the first engagement portion of includes a cradle and a cutout, the cradle of the delivery member nesting within the cutout of the implant.

In accordance with another aspect of the present invention, a system for delivering a vascular implant into a body lumen of a patient is provided comprising an elongated delivery member engageable with a vascular implant, a textile structure positioned over a portion of the elongated delivery member and an elongated member extending through the delivery member. The elongated member has an extended position and a retracted position, wherein in the extended position the elongated member extends into at least a portion of the implant to prevent release of the implant from the delivery member and in the retracted position the elongated member is withdrawn from the implant to enable release of the implant from the delivery member.

In some embodiments, the delivery member includes a coil and the textile structure positioned over the coil. The textile structure can in some embodiments be in the form of a braid.

The elongated member can include a coil positioned thereover to limit distal movement of the elongated member. In some embodiments, the elongated member has a buckling portion within the delivery member proximal of the textile structure to provide extra length to prevent premature retraction or foreshortening of the elongated member and uncoupling of the implant during tracking of the delivery member through vasculature.

The system can include a release mechanism connected to the delivery member including a cut forming a break away joint for the elongated member and delivery member.

In accordance with another aspect of the present invention, a method for delivering a vascular implant into an aneurysm of a patient is provided comprising:

providing an elongated delivery member having an engagement portion at a distal portion releasably engageable with a vascular implant and an elongated member extending through the delivery member;

inserting the elongated delivery member through the vasculature to the aneurysm with the elongated member maintained in an extended position wherein it is positioned in at least a portion of the vascular implant extending into a radiopaque portion of the implant; and retracting the elongated member to decouple the vascular implant from the delivery member to deliver the vascular implant to the aneurysm.

In some embodiments, the step of retracting the elongated member causes camming surfaces of the vascular implant and delivery member to move the vascular implant and delivery member radially away from each other.

In some embodiments, the elongated member moves within a braid of the delivery member, the braid of the delivery member providing a more flexible region of the elongated member. In some embodiments, the elongated member includes a stop to limit distal movement of the delivery member and a radially extending structure to provide resistance to movement of the elongated member.

In accordance with another aspect of the present invention, a system for occluding a vasculature of a patient is provided comprising a vascular micrograft having an absorbent polymeric structure, a lumen for passage of blood therein, an outer wall, and a retaining structure attached to the vascular micrograft. A delivery element has an engagement structure cooperating with the retaining structure to retain the vascular micrograft during insertion by the delivery element through the vasculature.

In some embodiments, the vascular micrograft is an occluding device which is a polymer structure formed as a non-expanding braid composed of multiple multi-filament yarns of polymeric material. In some embodiments, the polymer structure is absorbent and wicks blood via a capillary action in a distal to proximal direction.

In some embodiments, the implant is shape set to a non-linear configuration and advanceable from a substantially linear configuration coaxially positioned on the delivery member to the same or different non-linear configuration placed within the aneurysm.

The intra-aneurysmal micrograft disclosed herein can have a tubular body that has a textile construction with a through lumen that has a series of peaks and valleys, or a wavy profile (dependent on wall thickness), running longitudinally across its length. At either end of the tubular body, bands can be provided which may optionally be radiopaque and/or used for mating to a delivery system. In another form of the construction, one or both ends of the graft can be shape set with a "J" or curl or other shape that help with delivery. In yet another form of the construction, agents can be added to the inner or outer diameter of the tubular body to aid in delivery (visualization), cancer treatment and/or endothelial cell growth.

These and other features of the invention will become more fully apparent when the following detailed description is read in conjunction with the accompanying drawings.

BRIEF DESCRIPTION OF THE DRAWINGS

FIG. 1 is a side view partial cut away of an intra-aneurysmal micrograft in accordance with one embodiment of the present invention;

FIG. 2A is a view of another embodiment of the intra-aneurysmal micrograft of the present invention having a larger diameter and thinner wall;

FIG. 2B is a side view similar to FIG. 2A except showing the micrograft stretched to highlight the peaks and valleys;

FIG. 2C is a side view of the micrograft of FIG. 2A in a bent placement position;

FIG. 3A is a side view of another embodiment of the intra-aneurysmal micrograft formed into a helical shape;

FIG. 3B is a side view of another embodiment of the intra-aneurysmal micrograft having a flared end to be directed by blood flow;

FIG. 4A is a side view partial cut away of an intra-aneurysmal micrograft in accordance with another embodiment of the present invention;

FIG. 4B is an enlarged view of a proximal end of the micrograft of FIG. 4A;

FIG. 4C is side view of a proximal end of an alternate embodiment of the micrograft of the present invention;

FIG. 4F is a cross-sectional view of the micrograft of FIG. 4A showing the entire micrograft;

FIG. 4G is a cross-sectional view similar to FIG. 4F showing an alternate embodiment of the micrograft;

FIG. 6 is a side view of a rapid exchange pusher catheter for micrograft delivery in accordance with another embodiment of the present invention;

FIG. 7 is a side view of another embodiment of the intra-aneurysmal micrograft delivery system of the present invention having a pusher wire with locking arms;

FIG. 8 is a side view of another embodiment of the intra-aneurysmal micrograft delivery system of the present invention using a stent or flow diverter to push the micrograft;

FIG. 9 is a side view of an intra-aneurysmal micrograft introducer system in accordance with another embodiment of the present invention;

FIG. 10 is a side view illustrating the loading of an intra-aneurysmal micrograft delivery system of FIG. 5A into a microcatheter;

FIGS. 11A-11F illustrate delivery of an intra-aneurysmal micrograft into an intracranial aneurysm in accordance with an embodiment of the present invention wherein:

FIG. 11A shows the delivery wire inserted into the aneurysm sac;

FIG. 11B shows initial advancement of the micrograft into the intracranial aneurysm after removal of the wire;

FIG. 11C is an enlarged cross-sectional view of the micrograft exiting from the catheter corresponding to the position of FIG. 11B;

FIG. 11D shows the micrograft fully deployed from the catheter and positioned in the intracranial aneurysm;

FIG. 11E is an enlarged cross-sectional view of the deployed blood-filled micrograft corresponding to the position of FIG. 11D;

FIG. 11F shows multiple micrografts of FIG. 11E positioned in the intracranial aneurysm sac;

FIG. 13 illustrates delivery of smaller length flow directed intra-aneurysmal micrografts into an intracranial aneurysm in accordance with another embodiment of the present invention;

FIG. 14 illustrates delivery of the delivery wire carrying the intra-aneurysmal micrograft through cells of a stent or flow diverter into an aneurysm in accordance with another delivery method of the present invention;

FIG. 15 illustrates delivery of an intra-aneurysmal micrograft into an aneurysm using a delivery wire with the arms of FIG. 7;

FIG. 16A is a photograph of an uncrimped tubular PET braid alongside a crimped braid of the present invention to show a wave-like profile as in FIG. 1A;

FIG. 16B is a photograph of a crimped micrograft braid alongside a crimped micrograft braid that has been heat set into a coiled shape in accordance with an embodiment of the present invention;

FIG. 16C illustrates a micrograft tubular body of the present invention partially filled with a fluid to illustrate the capillary effect.

FIG. 17 is a photograph of one end portion of the micrograft of FIG. 1A;

FIG. 23A is a side view of another alternate embodiment of the delivery system of the present invention;

FIG. 23B is a side view of the delivery system of FIG. 23A interlocking with a micrograft of the present invention;

FIG. 24 is a side view of another embodiment of the delivery system of the present invention delivering a micrograft and a flow diverter;

FIGS. 25A, 25B, 26A, 26B, 27A, 27B, 28A and 28B show a comparison of the braid before and after crimping (the inner coil removed for clarity) wherein FIGS. 25A and 26A are close up views of the braid prior to crimping and FIGS. 25B and 26B are close up views of the braid after crimping, FIG. 27A is a transverse cross-sectional view of the braid prior to crimping and FIG. 27B is a transverse cross-sectional view of the braid after crimping, and FIG. 28A is a perspective view of the braid before crimping and FIG. 28B is a perspective view of the braid after crimping;

FIG. 29 is a top view of packaging for the vascular implant in accordance with one embodiment of the present invention;

FIG. 30 is an enlarged top view of the container portion of the packaging of FIG. 29; and FIGS. 31-36 illustrate the steps of removing the vascular implant from the packaging of FIG. 29 wherein FIG. 31 illustrates grasping of the delivery wire for proximal movement, FIG. 32 illustrates the delivery wire being pulled proximally relative to the delivery sheath to pull the implant into the sheath; FIG. 33 illustrates grasping of the sheath and delivery wire for proximal movement; FIG. 34 illustrates the sheath and wire being pulled in tandem proximally to pull the sheath and delivery wire (delivery system) out of the packaging hoop, FIG. 35 illustrates grasping of the delivery wire for distal movement, and FIG. 36 illustrates the delivery wire pulled distally out of the packaging hoop.

FIGS. 37A, 37B, 38, 39, 40 and 41 are perspective views of an alternate embodiment of the delivery member wherein:

FIG. 37A shows the implant tube and delivery member uncoupled, with portions shown transparent to illustrate internal components;

FIG. 37B is a perspective view of the implant and delivery member of FIG. 37A shown uncoupled;

FIG. 38 shows the implant tube and delivery member coupled, with portions transparent to show internal components, and the inner wire shown in the extended position;

FIG. 39 is a view similar to FIG. 38 showing the implant tube and delivery member coupled;

FIG. 40 is a view similar to FIG. 38 showing the wire in the retracted position to decouple the implant and delivery member;

FIG. 41 is a side view of an alternate embodiment of the delivery system of the present invention;

DETAILED DESCRIPTION

Figure 4D:
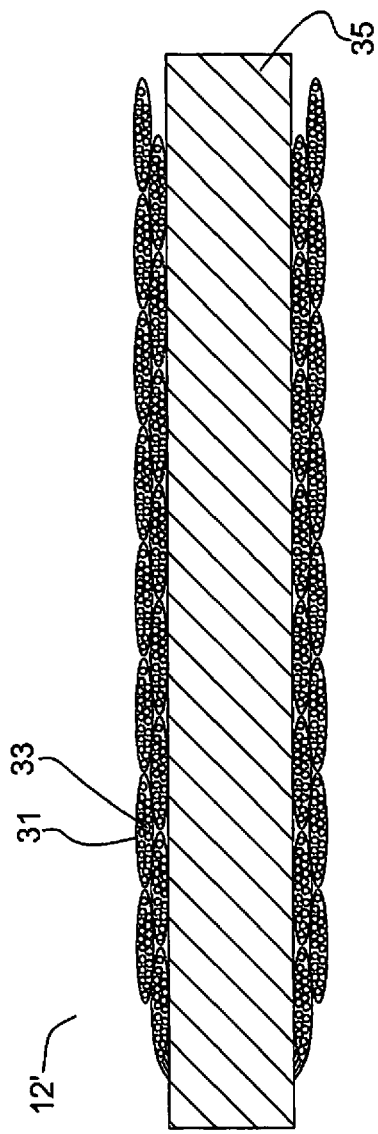
FIG. 4D is a cross-sectional side view of the micrograft of FIG. 4A placed over a mandrel before crimping.

The following embodiments are described in sufficient detail to enable those skilled in the art to practice the invention, and it is understood that structural changes may be made without departing from the scope of the present invention. Therefore, the following detailed description is not to be taken in a limiting sense. Where possible, the same reference numbers are used throughout the drawings to refer to the same or like components or features.

FIG. 1 illustrates a partial cut away side view of an intra-aneurysmal micrograft for insertion into an intracranial aneurysm in accordance with one embodiment of the present invention. The micrograft of this embodiment, designated generally by reference number 10, includes a biocompatible non-self-expandable absorbent braided polymeric textile tubular body 12 that has been crimped to reduce stiffness and increase wall thickness and fabric density. The micrograft 10 has sufficient stiffness as well as sufficient flexibility to provide the advantages described below. It further is structured to enable a triple capillary action to promote blood clotting as also discussed in detail below. The micrograft further preferably has a high surface area for increased blood absorption, is radially deformable, has a low friction surface for ease of delivery and can be shape set to enhance packing of the aneurysm. These features and their advantages are described in more detail below. Note the micrografts of the present invention are especially designed to induce blood stagnation or clot to rapidly treat the aneurysm. The micrografts are configured for delivery to an intracranial aneurysm, although they can be utilized for occlusion in other aneurysms in other areas of the body as well as for occlusion in other vascular regions or in non-vascular regions.

An over the wire delivery system is provided to deliver the micrograft of the present invention to the aneurysm. Variations of these delivery systems of the present invention are discussed in detail below. Preferably, multiple micrografts are delivered so that the aneurysm sac is densely packed.

Turning first to the biocompatible micrografts of the present invention (the delivery systems are subsequently discussed) the preferred tubular body 12 of micrograft 10 is constructed of substantially 100% 20 denier/18 filament polyester (e.g., PET) multi-filament interlaced yarns, but can be made of other combinations of denier and filament such as 10 denier/16 filament yarn, or 15 denier/16 filament yarn, for example. That is, each yarn is composed of a plurality of polyester filaments having pores or spaces therebetween, and the plurality of yarns also have pores or spaces therebetween, for reasons described below. The tubular body has a proximal end 14 and a distal end 16, with proximal defined as closer to the user and distal defined as further from the user such that the distal end is inserted first into the aneurysm. Blood then flows through the micrograft 10 in a distal to proximal direction. The tubular body 12 has a preferred inner diameter in the range of about 0.001 inches to about 0.068 inches, and more narrowly in the range of about 0.006 inches and about 0.040 inches, for example about 0.008 inches. It has a length ranging from about 2 mm up to about 150 cm and a preferred outer diameter in the range of about 0.002 inches to about 0.069 inches, more narrowly in the range of about 0.010 inches to about 0.041 inches, for example about 0.010 to about 0.020 inches. Note that although these ranges and dimensions are the preferred ranges and dimensions, other ranges and dimensions are also contemplated. These dimensions provide a sufficiently small size micrograft so that the micrograft can be navigated to and into the cranial vasculature for placement within a cranial vessel.

Each of the multi-filament yarns are made of multiple wettable micro-filaments, or fibers, assembled with spaces (pores) between them, referred to as inter-fiber spaces or pores. The pores are sufficiently sized to induce capillary action when contacted by a liquid, resulting in the spontaneous flow of the liquid along the porous yarn (i.e., wicking). This capillarity between fibers (intra-fiber) within the yarn is termed as "micro-capillary" action. As a result, a sufficiently wettable and porous yarn will have high wickability and transport liquid along its length. The multiple filaments also provide a high surface area and can be hydrophilic or hydrophobic.

This assembly of the two or more wickable multi-filament yarns into a permeable structure (such as a textile) results in a "macro-capillary" action, i.e., the transporting of liquid between the yarns and throughout the structure. Such yarns and/or fibers can be textured, flat, twisted, wettable, non-wettable, with beads, of various cross-sections (tri-lobal, multi-lobal, hollow-round, etc.), coated or having a modified surface, composite, reticulated, porous, pre-shrunk, crimped or modified using similar heat treatment or chemical processes.

The multi-filament yarns can be assembled into a textile tubular structure using a braider or other textile manufacturing equipment and methods. In general, the braider can be set-up with a program or recipe, spools of multi-filament yarn and an optional core mandrel to braid over. Anywhere from about 8 to about 288 strands of multi-filament yarn may be used to form the tube, depending on the desired final structural properties such as density, picks per inch (PPI), porosity, compliance, etc. If desired, multiple braiders or a braider in combination with a coil winder can be run simultaneously to form a braid over braid or braid over coil design.

The vascular graft (micrograft) has a proximal opening at the proximal end and a distal opening at the distal end for blood flow into the distal end and through the lumen (the proximal and distal openings aligned with a longitudinal axis), thereby forming a conduit for transport of blood through the continuous inside lumen (inside diameter). A capillary effect is created within the vascular graft when the biocompatible structure is exposed to blood such that blood is transported in a proximal direction through the distal opening in the vascular graft and through the vascular graft wherein blood clots. Thus, blood initially flows through the distal opening, through the vascular graft and towards the proximal opening, with blood quickly stagnating within the graft. In some instances, blood will exit the proximal opening (e.g., if there is sufficient pressure); in other instances capillary action will only fill the graft and not cause flow out the proximal opening. The vascular graft retains blood, and becomes saturated with blood, to promote clotting. The outer member, i.e., the textile structure, as disclosed herein is configured as a tubular member for flow therein, functioning as a capillary tube. That is, the tubular textile member is configured in a closed cell fashion so as to form a tube for flow therethrough, i.e., the lumen inside the textile structure is sufficiently small to enable function as a capillary tube, but the textile structure still has sufficient sized openings/spaces for absorbing blood through and along the yarns and filaments as described herein. Thus, a continuous wall (continuous inner diameter) is formed along the length of the textile structure to retain blood while also maintaining small spaces (micro-capillaries) in between fibers to wick and absorb blood. This closed cell or tight textile, e.g., braided, structure is maintained in the non-expanding embodiments disclosed herein since the diameter of the textile structure (and thus the diameter of the vascular graft) does not change from the delivery to implant positions. That is, the textile structure is non-expanding such that when it is delivered to the aneurysm its outer diameter X is equal to its outer diameter X when positioned within the delivery member. In an expanding textile structure, at least upon initial expansion or expansion to a certain size/percentage, spaces between filaments and/or yarns would increase as the device expands to a larger outer diameter, thereby increasing openings so as to increase or create an open cell structure. In some embodiments, the closed cell structure of the embodiments disclosed herein forms such small openings that the inner element, i.e., the core element, covered by the textile structure is not visible through the outer textile structure.

As noted above, the tubular textile structure (which forms a braid in some embodiments) forms a continuous circumferential wall along a length without large spaces between the filaments and/or yarns. This continuous wall is shown in the tight spacing of FIGS. 4A-4D and thus creates a continuous outer member (low porosity wall) to contain and direct flow. In contrast, the use of large open pores between filaments would result in an outer member (outer textile structure) with a non-continuous wall that would allow blood to pass radially through the large pores or gaps between strands of the textile structure (forming a highly porous wall) so the structure will not contain or direct blood flow and thus capillary action (effect) will not take place nor will it behave like a vascular graft that transports blood therethrough. Instead, it will act more like a net or strainer rather than a conduit for blood, let alone a capillary tube (tubular structure). That is, the yarns of the textile structure in preferred embodiments are close enough to form a continuous wall to wick and transfer blood via the wall and inside lumen.

Capillary action, or capillarity, can be defined as the ability of liquid to fill fine gaps or voids with wettable walls driven by capillary forces that arise from wetting of the walls (e.g., fiber surface). Wettability, or wetting, is the ability of a solid surface to attract a liquid in contact with it such that it spreads over the surface and wets it. Wickability, or wicking, is the spontaneous flow of a liquid driven by capillary forces. Capillary flow through a textile medium is due to a meniscus (wetting) formed in microscopic, interconnected voids between fibers and yarns. Wicking in a textile or fibrous medium can only occur when a liquid wets fibers assembled with capillary spaces between them. Because capillary forces are caused by wetting, a structure experiencing capillarity is constructed of wettable fibers with sufficiently small, inter-connected gaps. Since the textile structures disclosed herein are composed of wettable yarns and the yarns are made up of wettable fibers, which wick blood, capillary flow in such a wall structure of the textile structure can be considered as the filling of capillary spaces between fibers within a yarn (inter-fiber) and between yarns (inter-yam) in the wall of the textile structure. The capillary spaces formed between yarns can be termed as macro-capillary and capillary spaces formed between individual fibers of a yarn may be termed micro-capillary as described herein. It should be appreciated the capillary action occurs as the yarns making up the wall of the textile structure and the fibers making up the yarns are assembled close enough, as shown for example in FIGS. 4A and 4M, to create micro-capillaries that induce wicking as in the textile structure of the vascular grafts disclosed herein. Thus, the tubular textile structure of embodiments disclosed herein utilizes the three capillary actions (i.e., inside (inner) lumen, inter-yam and inter-filament capillary actions) to act as a capillary tube and also achieves blood retention inside the tubular structure. As can be appreciated, capillarity is dependent on pore size, meaning gaps in the textile structure have to be sufficiently small to initiate capillary flow (i.e., smaller pores or spaces result in better wicking). The textile structure will not induce capillary action if there is excessive porosity of the textile structure.

The vascular graft of the present invention advantageously promotes blood clotting, i.e., induces blood stagnation or clot to rapidly treat the aneurysm. This is achieved in part by the construction of the vascular graft holding blood therein once blood permeates the graft. The blood in some embodiments permeates the graft when still held by the delivery member and positioned in the aneurysm.

By forming the textile structure as a tubular member (rather than winding/braiding the filaments about an inner element), and then inserting/positioning the inner core element therein for attachment to the outer textile structure, portions of the inner surface of the inner wall of the textile structure are in contact with the inner element. In some embodiments, these contact portions can be end portions. In other embodiments these contact portions can be the areas of the valleys of the crimped textile structure. Other intermittent contact portions are also contemplated. Current embolic coils require an internal stretch-resistant member to prevent stretching or unraveling during use. In the tubular textile structures disclosed herein, an internal stretch resistant member is not necessary since the risk of unwinding or unraveling of the internal element, e.g., radiopaque coil, is not present since the textile structure provides stretch resistance. Thus, the implant structure of the implants disclosed herein can be devoid of such additional internal stretch resistant member(s). The absence of such stretch resistant member inside the structure also provides an obstruction-free lumen so as not to interfere or inhibit blood flow through the distal end and through the lumen of the vascular graft.

The micrograft 10 is braided over the core mandrel which sets the internal diameter (ID) of the braid. The core mandrel can be made of a variety of materials such as metal, wire, polymers or other textile fibers. It can also be formed of a stretchable material to aid in removal during manufacturing.

The micrograft 10 in preferred embodiments can also include a permanent core element such as shown in the embodiment of FIG. 4A discussed below. The core element can be made of a variety of materials, and can itself be formed of one or more filaments, and may optionally be coated. In one preferred embodiment, the core element is formed of a metal coil having a lumen therein. It can be composed of platinum-tungsten or other materials. The braid and coil can be heat set at a temperature that would not damage or disintegrate the braid.

The braiding process may be adjusted for the highest PPI possible so as to produce a tightly interlaced, dense braid without tenting (braiding over itself or overlapping). However, in some cases tenting may be desirable to produce a useable feature such as a braid bulge or ring for locking or wall thickening. The braid, while still mounted on the core mandrel, may be heat treated after manufacturing to set the braid structure, including PPI, and to relieve filament stresses produced during braiding.

The preferred PPI for the as-braided therapeutic structure, for example, may range from about 80 to about 200 PPI for a 16 strand braid, and more narrowly in the range of about 120 to about 180 PPI, preferably about 167 PPI. The PPI is dependent on the number of strands used to braid, the braid angle, and the braid diameter, such that a braided tube of a given diameter with 120 PPI and 16 strands would have a PPI of 60 when braided using 8 strands at the same diameter (assuming all of the variables constant). The preferred PPI should be high enough to produce a dense interlacing pattern, but not so high as to interfere with core mandrel removal, unless the core is stretchable. Crimping, which will be discussed later in detail, may be used to increase PPI (and braid angle), once again depending on final structural requirements.

The use of multi-filament yarns in combination with a relatively high PPI of the present invention results in a somewhat stiff, relatively small or closed cell (high pick density) braided tube. As mentioned above, there is a micro-capillary effect resulting in wicking of liquid along the porous yarns due to inter-fiber spaces and a macro-capillary effect resulting in liquid flow between yarns and throughout the textile wall due to inter-yarn porosity associated with using a wettable multi-filament yarn. Due to the manufactured tube's relatively small inner diameter and a sufficiently dense interlacing braid pattern (i.e., a filamentary wall structure with sufficiently small pore size such that it retains fluid), a third capillary effect is created. When properly sized, this third capillary effect is responsible for spontaneous flow of liquid inside the micrograft lumen, e.g., within the lumen of the braid, in a proximal direction. In the embodiment of FIG. 4A which includes the inner element, the third capillary effect is through either or both a) the lumen of the inner element which is in the lumen of the braid so the capillary effect is within the braid lumen; and/or b) in the gap between the inner diameter of the tubular braid and the outer diameter of the inner element. The liquid can also spread in other directions as it is absorbed. This structure thus results in a soft capillary tube that has absorbent walls. This triple capillary effect is beneficial for a vaso-occlusive device due to the fact that the yarns, the fibrous wall, and the micrograft lumen can become saturated with blood. Since blood absorbed by the micrograft is trapped within the structure, it becomes stagnant and will quickly thrombose or form clot. In an exemplary embodiment, the inner diameter is preferably about 0.003" to about 0.012", and more preferably about 0.007".

To achieve the capillary and clotting characteristics, the micrograft 10 achieves an optimal balance of porosity and fluid containment within the same structure. This is achieved by controlled interlacing of microporous yarns that allow blood wicking and cell ingrowth. When braided with sufficiently high PPI and tension, for example, the porous yarns are able to form a fluid barrier that maintains a degree of permeability. The resultant structure (textile tube) is an assembly of micro-porous yarns that may be interlaced with sufficient density to form a fluid-tight tubular capillary. This interlacing of the yarns or assembly of filaments can be achieved using textile manufacturing processes, such as weaving, knitting, or electrospinning. Porous or semi-porous filaments may also be used in place of multi-filament yarns to achieve desired absorbency. Additionally, the micrograft structure does not have to include a clearly defined inside lumen to maintain capillarity, e.g., a defined lumen formed within the wall of the braid or core element, but may alternatively be a porous assembly of fibers sufficiently spaced to allow transport of liquid (much like a suture or string wicking liquid) or a porous scaffold or biocompatible open cell foam.

While the semi-porous micrograft 10 as formed as described above has the desired effect of aiding thrombus formation, it is also relatively stiff as a result of the filaments being closely packed or tightly braided as mentioned above. One benefit of a stiff, denser braid is its ability to retain its non-linear heat-set shape as compared with lower PPI (less dense) braids. This may facilitate the use of stiffer, higher density 3D shaped micrografts as framing-type devices used for initial filling of aneurysm circumference, and then soft and highly compliant micrografts may be used as fillers or "finishing" devices towards the end of the embolization procedure. For example, a dense (or high PPI) 2×2 (two-over-two) configuration braid may be used as the initial "framing" device whereas a softer and more compliant braid having a lower-PPI 1×2 (1-over-2-under-2) configuration braid may be subsequently used to fill the framed space within the first device. However, even if used as a framing device, excessive stiffness is an undesirable mechanical property for the microcatheter delivery because an overly stiff device may cause unwanted movement of the microcatheter tip during delivery which can adversely affect navigation of the microcatheter or damage vessels during advancement through the tortuous vasculature. Excessive stiffness is also an undesirable property because stiff devices will conform less to the configuration of the aneurysmal sac and thus prevent efficient aneurysm packing.

Therefore, to reduce stiffness to assist delivery and packing of the aneurysmal sac, the micrograft tubular body (braid) 12 is crimped during manufacture, i.e., longitudinally compressed and heat set. As the braid 12 is compressed, axial orientation of the braided strands is reduced thereby increasing braid angle with respect to the longitudinal axis of the tubular body which reduces their influence on overall stiffness of the structure, much like a straight wire taking on a more flexible form when coiled. Crimping will also effectively increase the PPI, wall thickness, and linear density of the braid by axially compressing the structure and filament bundles. This compression causes an outward radial expansion and an increase in wall thickness of the tube. The resulting braid is much more deflectable, has reduced bend radius, a higher density and up to 2× to 3× or higher increase in PPI, depending on braid structure and compressive force applied.

This axial compression also causes the braid structure to "snake" or produce a spiral wavy form as shown in FIG. 1, which as viewed from the side is a series of macro peaks and valleys, termed "macro-crimps" in a sinusoidal shape. The sinusoidal undulations (macro-crimps) are typically more pronounced in braid structures where the ratio of wall thickness to overall braid diameter is larger (i.e., overall diameter decreases). Sufficient crimping may also re-orient individual yarn fiber bundles from a mostly flattened (longitudinally organized cross-section) state to a compressed (transversely organized cross-section) state. This increases surface unevenness of the braid since individual yarns bulge outward and produce micro peaks and valleys on the braid surface, termed "micro-crimps" (see FIGS. 4B and 25B for example) with the peaks 17 located at the height of the yarn and the valleys 19 between adjacent yarns.

The braid can have a series of coaxial aligned filaments and compressed so the filaments orient substantially transversely (with respect to a longitudinal axis of the mandrel).

Different braid patterns (such as 1×1, 1×2, or 2×2, etc.) may also produce varied results when crimped. For example, a 1×1 braid structure will tend to have a more uniform tubular shape and less distinctive macro-crimp pattern, whereas a 1×2 braid structure will produce a more sinusoidal (macro peaks and valleys) crimped structure in addition to the micro peaks and valleys (micro-crimps) of individual fiber bundles. These structural changes result in an ultra-deflectable, increased density, wavy-wall structure having macro-peaks 18 and valleys 20 as shown in the sinusoidal shape of FIG. 1.

Besides increasing braid flexibility, PPI and/or wall thickness, varying amounts of crimping imparts other potentially desirable features such as kink and crush resistance, reduced bend radius, as well as increased surface area per unit length via accordion-like compression of the wall (i.e., forming peaks and valleys). The uneven texture of crimped peaks and valleys also helps create localized hemodynamic turbulence and flow stagnation, resulting in improved thrombus formation. The crimps make the device more compliant, easily deflectable and conformable which facilitates packing confined spaces or voids in the vasculature, e.g., the aneurysm. Crimping may also be used to vary wicking and permeability of the textile wall since it reduces fabric porosity and increases yarn tortuosity.

The location, amount and magnitude of crimping can be controlled to impart different amounts of flexibility and elongation to the structure to achieve its desired characteristics. For example, extreme crimping can be applied so the braid is compressed until the individual fibers within each yarn bundle come together and cannot compress any further, giving the braid some rigidity and improving pushability through a microcatheter lumen. Other factors that impact crimping and the resulting longitudinal pattern are fiber diameter and stiffness, yarn tension during braiding, wall thickness, wall porosity (PPI), number of filaments, and mandrel diameter.

Figure 28B:
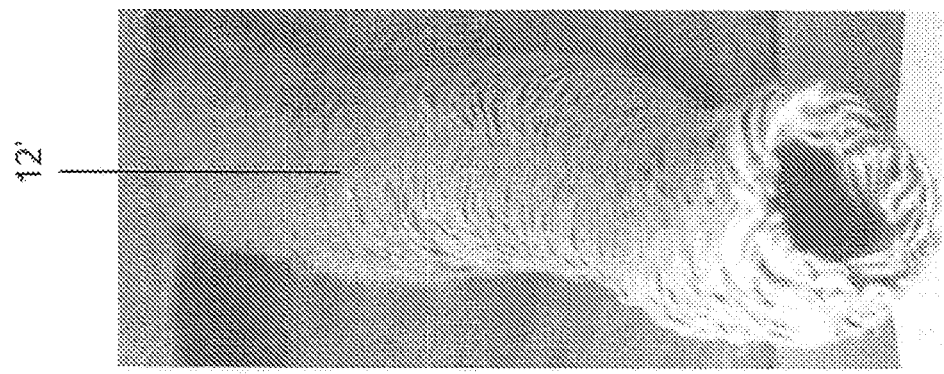
Figure 28A:
Figure 32:
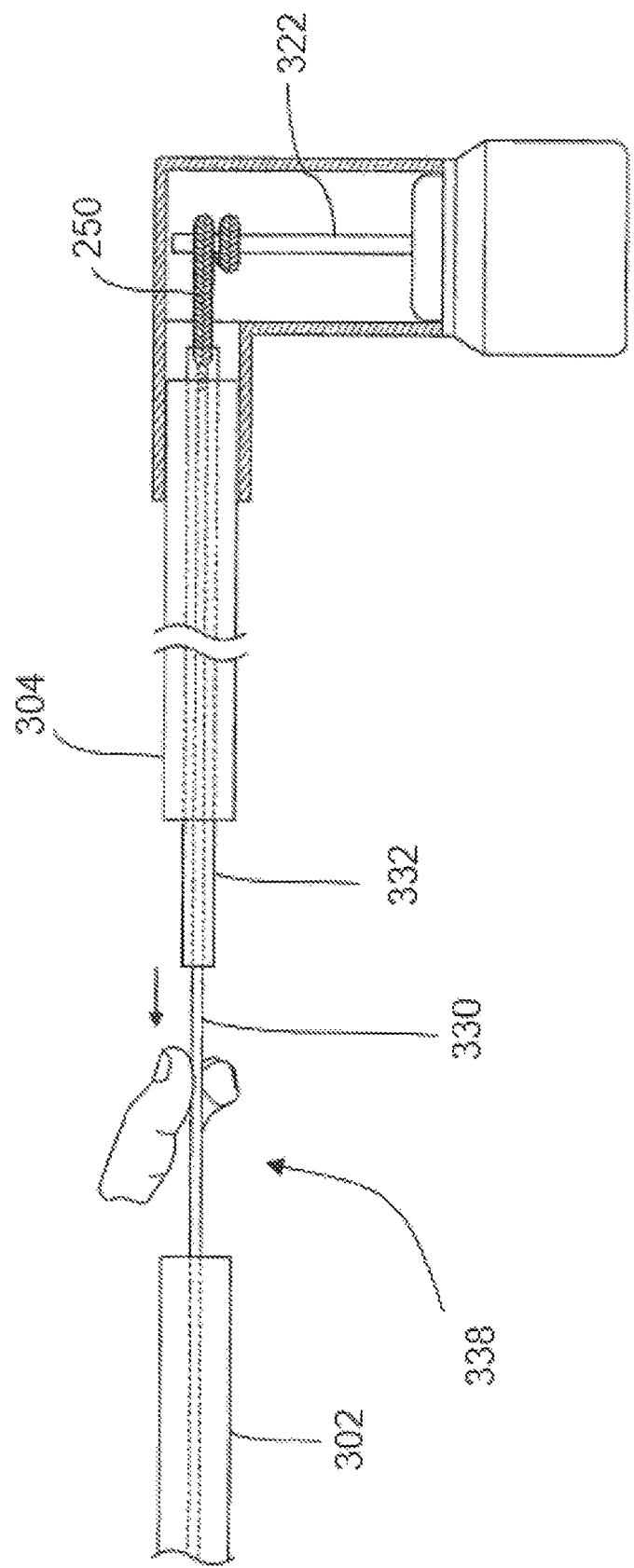
Figure 33:
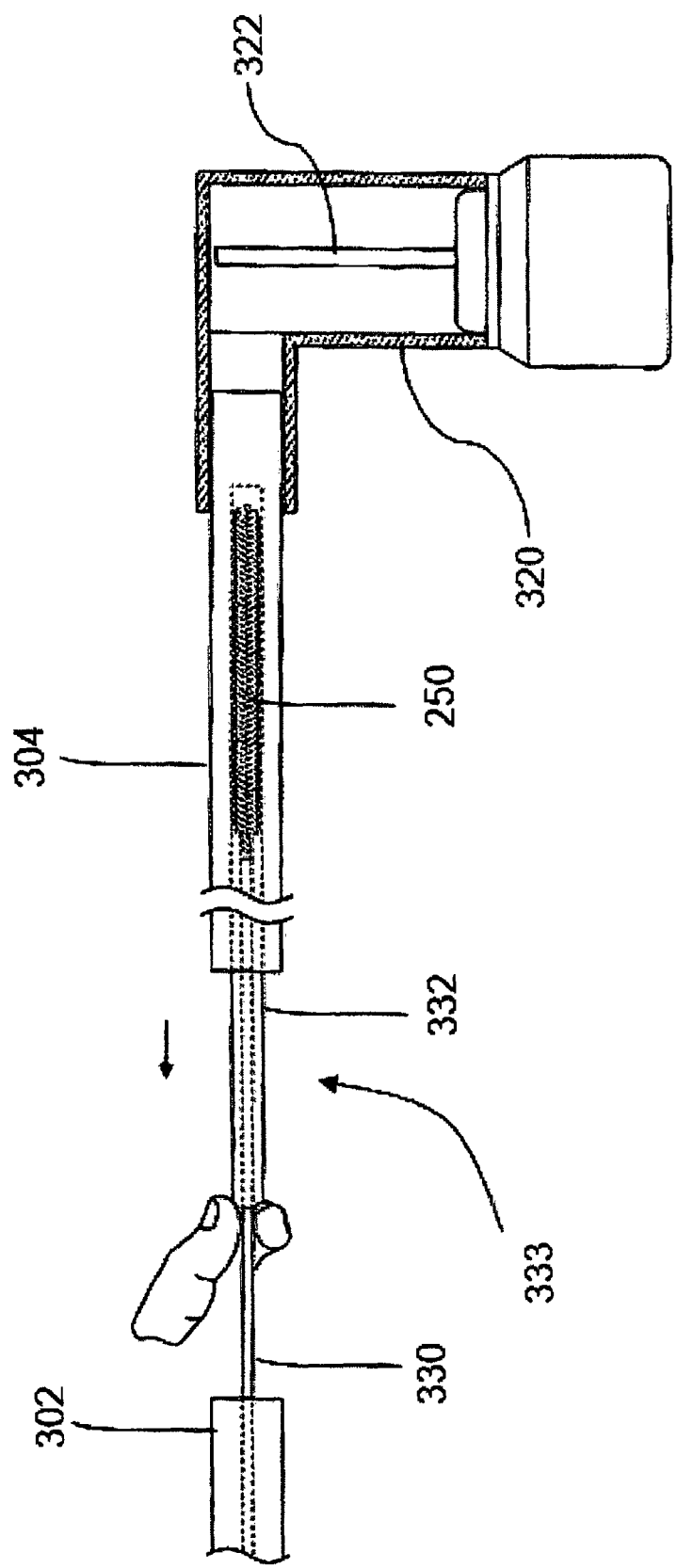
Figure 34:
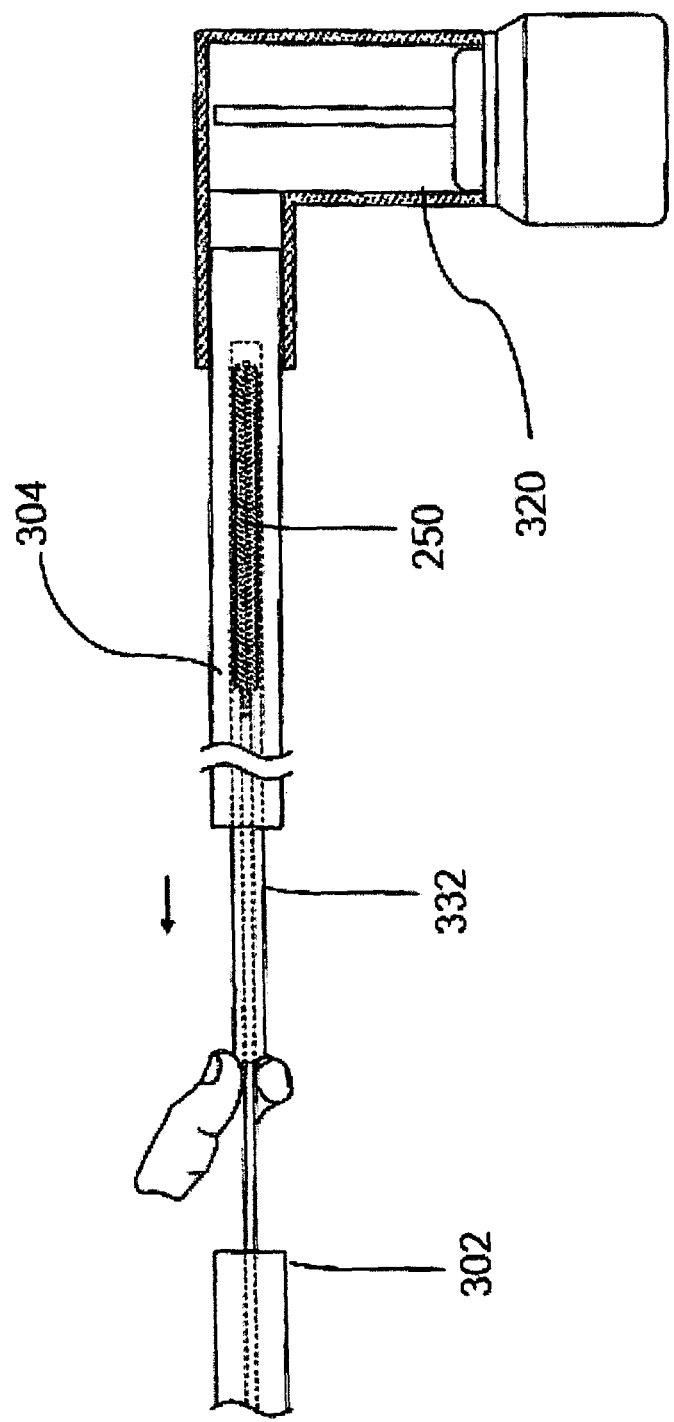
Figure 37A:
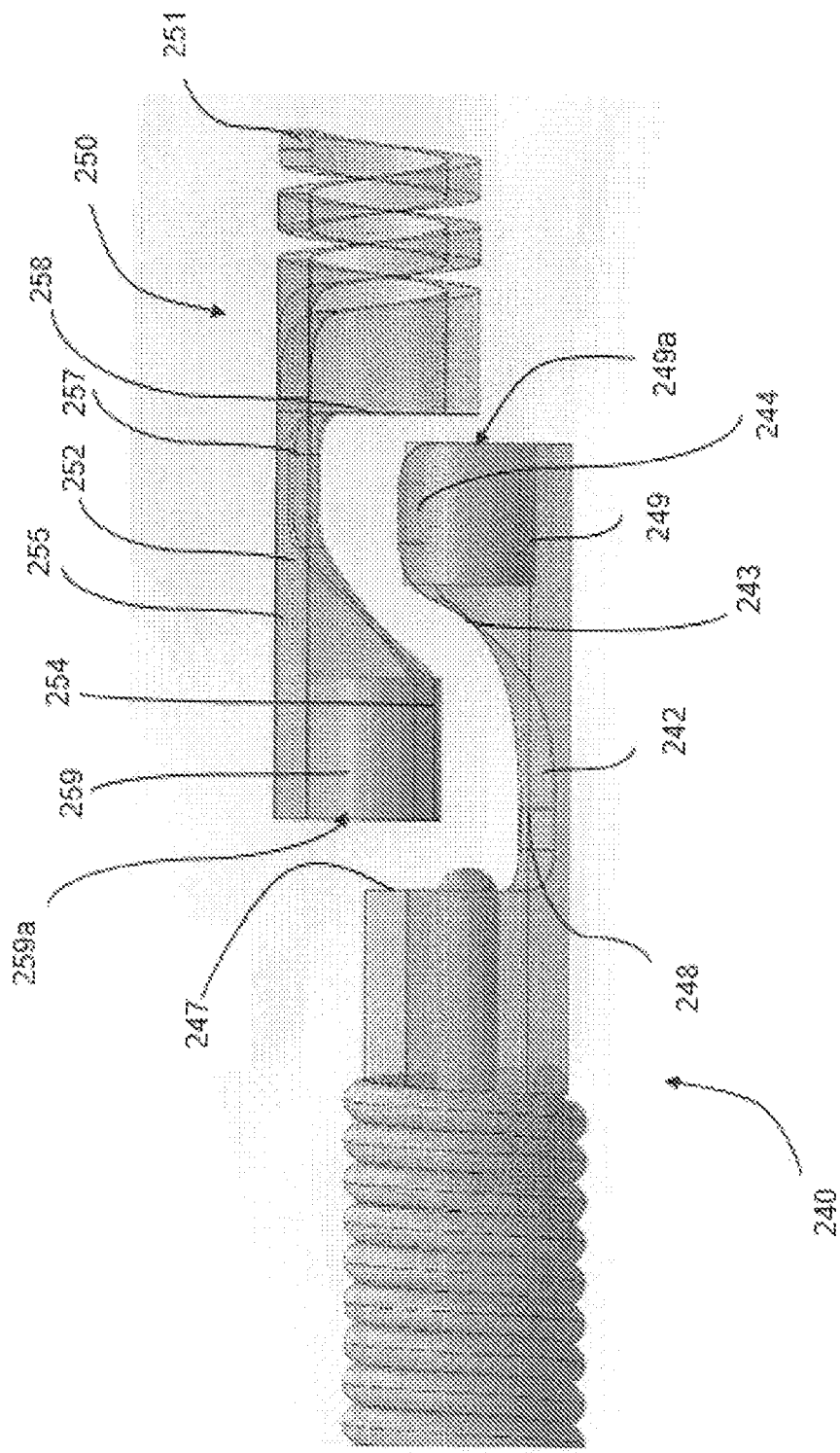
Figure 37B:
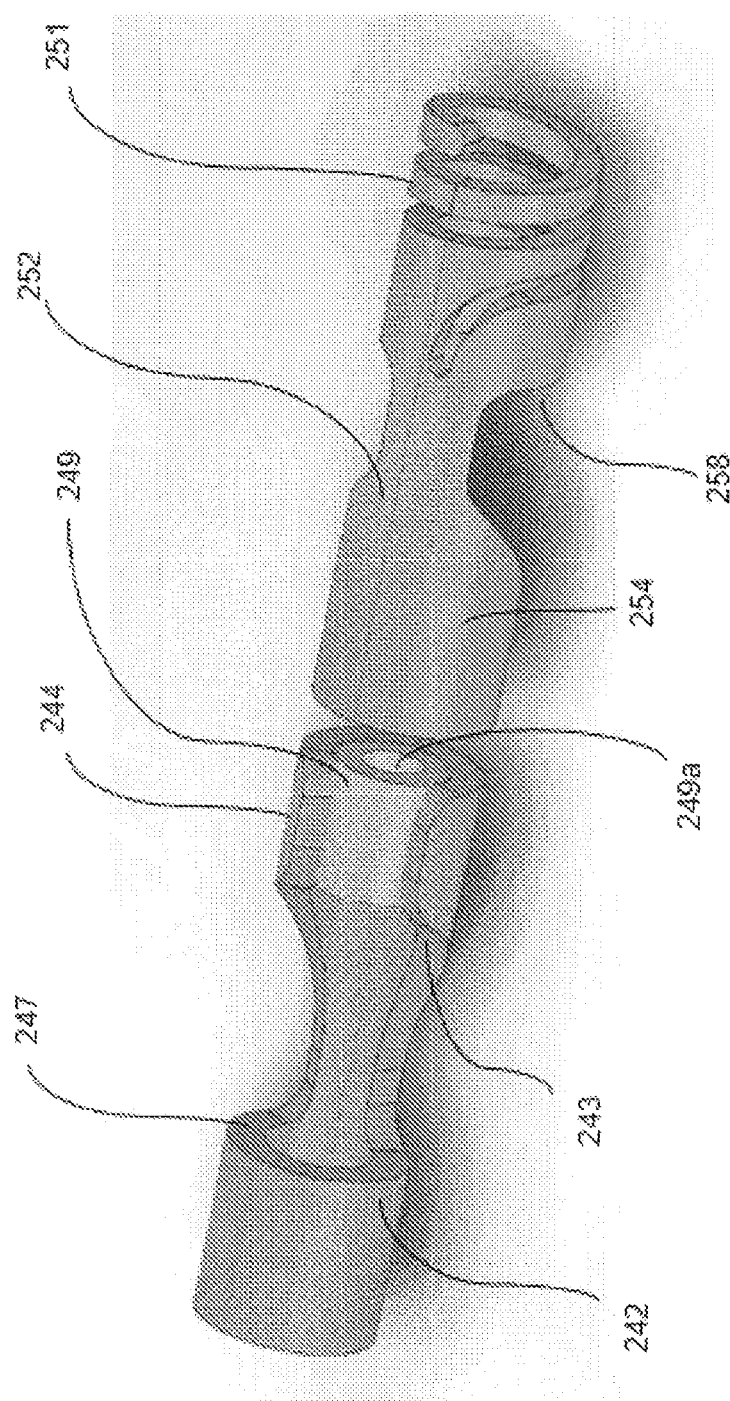

For example, larger diameter, thin walled tubular bodies (braids), i.e., low wall thickness to outer diameter ratio, may show macro peaks and valleys which are more dense and visible than small, thick walled crimped tubes. FIGS. 2A-2C show an example of such large diameter thin walled tube where crimping can form an accordion-like folds or pleat structure rather than a sinusoidal configuration as the peaks are closer together. Crimping smaller diameter braids (braids with higher wall thickness to outer diameter ratios) typically induces a wave-like, sinusoidal longitudinal (macro) contour that is larger in comparison to overall diameter and increases wall thickness of the structure, as shown in FIGS. 16A and 28B. It should be noted the sinusoidal contour is typically three-dimensional in form (like a spiral) and is visible from all sides of the braid. During crimping, the ends of the tubular body may also be rotated/twisted relative to each other and then heat set as another method to impart deflectability to the tubular body.

The crimps are produced by compressing the textile tubular structure axially to reduce length and thereby produce a longitudinally extending wavy shape. The crimping reduces an axial orientation of the fibers to increase a braid angle and increase a linear density and wall thickness by axially compressing the biocompatible tubular structure, and forms a series of alternating peaks and valleys along a length of a surface of a wall, i.e., in a longitudinal direction along the longitudinal axis, to form a longitudinally extending wavy sinusoidal shape. In some embodiments, crimping can increase the braid angle by at least 5 degrees. In other embodiments crimping can increase the braid angle by between 1 and 4 degrees. For example, in some embodiments, the braid angle pre-crimping can be between 1 degree and about 40 degrees and the post crimping angle can be between about 35 degrees and 90 degrees. Other angles are also contemplated.

The braid 10 can also be made more flexible by varying the braid angle or PPI, by reducing yarn tension, by adding cuts/slits, changing the number of filaments or strands, or heat setting repeating patterns along its length (such as flat sections or kinks). If a stiffer tube is desired, denser yarn and/or braid pattern may be used or crimping decreased. Additionally, the micrograft structure may incorporate a coaxial construction (i.e., having a graft inside a graft) or multi-ply or multi-lumen wall design, especially when using fine-denier textiles. Intra-luminal braid inserts, such as the coils mentioned above, may also be composed of, or coated with, a highly wettable/hydrophilic material to enhance the capillary effect. For example, the micrograft may be coaxially assembled with a secondary braid or internal coil structure that is highly hydrophilic and/or radiopaque, while maintaining the therapeutic external surface.

The tubular body 12 may be braided, woven or knitted, partially or completely, from monofilaments or multi-filament yarns, strands, sutures, microfibers, or wire that is synthetic, semi-synthetic, natural or thermoplastic. Such materials may include, but are not limited to, Dacron, poly ester amide (PEA), polypropylene, olefin polymers, aromatic polymers, such as liquid crystal polymers, polyethylene, HDPE (high density polyethylene), ultra-high-molecular-weight polyethylene (UHMWPE, or UHMW), polytetrafluoroethylene (PTFE), ePTFE, polyethylene terephthalate (PET), polyether ketone (PEK), polyether ether ketone (PEEK), poly ether ketone ketone (PEKK), nylon, PEBAX, TECOFLEX, PVC, polyurethane, thermo plastic, FEP, silk, and silicone, bio-absorbable polymers such as polyglycolic acid (PGA), poly-L-gllycolic acid (PLGA), polylactic acid (PLA), poly-L-lactic acid (PLLA), poly-caprolactone (PCL), polyethyl acrylate (PEA), polydioxanone (PDS) and pseudo-polamino tyrosine-based acids, extruded collagen. Metallic, metallic alloy or radiopaque material may also be included, Such material may be in the form of strands or filaments and may include, for example, platinum, platinum alloys (platinum-iridium or platinum-gold, for example), a single or multiple stainless steel alloy, nickel titanium alloys (e.g., Nitinol), barium sulfate, zinc oxide, titanium, stainless steel, tungsten, tantalum, gold, molybdenum alloys, cobalt-chromium, tungsten-rhenium alloys.

In preferred embodiments, the textile structure is formed of fibers of non-absorbable material such as the non-absorbable materials (materials which do not have a medical indication for the material to be absorbed into the tissues or absorbed by the human body) listed above.

The use of different manufacturing methods or materials to construct the tubular body may have an impact on the capillary effects discussed earlier. For example, a change in material or construction methods may result in a simple capillary tube with capillary flow restricted to only the inner lumen of the tube, and not the walls. It should be understood by those skilled in the art that strands or filaments may be braided, interwoven, knitted, or otherwise combined to form a fabric or textile structure.

With reference now to the drawings showing exemplary embodiments of the micrograft of the present invention, the micrograft 10 of FIG. 1, as discussed above has a tubular body 12 with a proximal end 14 and a distal end 16.

To provide radiopacity so the device is visible under fluoroscopy (x-ray), the micrograft 10 can include radiopaque structures such as radiopaque marker bands 22 which are inserted into the ends of the micrograft 10. FIG. 17 is a picture of an end of micrograft 10 with such marker band. The marker bands, which can also be in the form of coils or spheres, can be made from tantalum, platinum, platinum alloys (e.g., platinum-iridium alloy), gold, tungsten, or any suitable radiopaque material such as radiopaque polymer. The marker bands 22 are preferably approximately 1 mm or less in length and can be either of a sufficient inner diameter to slide over tubular body 12 or of a smaller diameter to fit inside the tubular body 12. FIG. 1 shows an example of the marker bands 22 fit inside the tubular body and the marker bands 22 can be secured by melting of the braid over the bands (the melted fiber) at region 24, or attached by gluing. The bands 22 can also be undersized and sliced lengthwise so that they can be swaged or folded over the outside of tubular body 12, or tubular body 12 can be stretched so that undersized bands can be slid over the stretched/compressed length in order to attach the bands 22 to the tubular body 12. In alternate embodiments, the bands can be flared at one end.

Although two marker bands are shown, in alternate embodiments, there may be one band or more than two bands placed around the tubular body along portions of its length to improve radiopacity. The bands positioned along the length can be in lieu of or in addition to a marker band at one end or a marker band at both ends. A radiopaque fiber can be utilized to connect the bands, and the radiopaque fiber incorporated into the textile structure, or placed inside the tube. The bands can be composed of metal, or alternatively of a non-metallic material such as radiopaque shrink tubing or polymer.

The marker bands can be adhered to the tubular body 12 using adhesive, mechanically by swaging or winding directly on to the tubular body, or by heating (when possible) and melting one of the materials. The bands can alternatively be attached by being screwed onto or into the core element, e.g., a helical core element, as discussed below.

In an alternate embodiment, radiopaque balls or spheres can be put inside the braid lumen to provide radiopaque structure. This provides the radiopacity while providing a less stiff, i.e., more deflectable, device. The balls or spheres can be spaced apart axially along the tubular braid, or alternatively one or more can be in contact with one another, and can be either as an addition to the radiopaque coil and/or marker bands or as an alternative. The coils and spheres can be made of the foregoing materials utilized for the marker bands.

As an alternative or in addition to the marker bands, radiopacity can be obtained by coating, wetting, staining, or impregnating the micrograft with a radiopaque material such as contrast media solution or nanoparticles. This can be done in manufacturing or in the operating room as part of the clinical procedure. The fibers or yarns themselves may be doped or impregnated or coated with radiopaque substances as described above. The micrograft may also contain a series of equally spaces radiodense inserts along its length, resulting in intermittent radiopacity which may be sufficient for visualization in clinical settings.

In addition to providing radiopacity, bands 22 can also be used to indicate structural changes in tubular body 12, as a means to control fraying, or as an integral part of the delivery system (e.g., stop-collar) as will be better understood in the discussion below of the delivery of the micrograft.

As another alternate to the bands, laser cut Nitinol structures that are made increasingly radiopaque can be utilized. These structures can be glued, melted over, sewn or otherwise attached to the proximal and/or distal ends of the micrograft, either on the inner or outer diameter, and/or attached along a length of the tubular body. Sections of the micrograft or meltable/fusible sleeves of a braided polymer may also be heated and used to adhere bands or other radiopaque structures (components) to the micrograft. Bands or other radiopaque components can alternatively be attached by screwing into the coil windings inside the braid as discussed in more detail below. The bands or other radiopaque components can either be self-expanding or non-self-expanding. When mated with the delivery wire and pusher catheter described below, they can serve to control micrograft linear movement relative to the wire.

As an alternative to the bands or other radiopaque structure for providing radiopacity, a radiopaque agent as described above could be utilized which would allow complete visualization of the full length of the graft. Another way to provide visualization is the inclusion of a radiopaque coil or insert across the entire length of the inner lumen of the micro-graft. The addition of such coil would make the entire length of the graft radiopaque, however, preferably, to avoid such coil adding an unwanted increase to the structure's radial stiffness, and to minimize such stiffness while maximizing x-ray visibility, such coil may be wound using very thin wire typically not visible via fluoroscopy, but when coiled with sufficiently small pitch (spacing between each loop) it becomes increasingly dense and visible. Pitch of the coil may also vary to make some sections more radiopaque or flexible than others. The coil can be made of materials such as platinum, platinum-iridium, tantalum, gold, silver or other radiopaque materials used for medical device visualization. The coil can have a continuous diameter or variable diameter along its length, depending on use. The coil can also be used in combination with radiopaque bands, coatings or as a stand alone radiopaque solution. Insertion of such coils inside the micrograft may also reduce the amplitude of macro-crimps formed during crimping if desired, depending on radial apposition of coil to braid. It should also be noted that coils or other internal inserts may be partially visible through the braid wall depending on the amount of crimping, although in preferred embodiments, the braid is closed cell, defined herein as the inner coil not being directly visible between braid strands or not being directly visible through gaps of the braid. However, in preferred embodiments, the closed cell configuration still has sufficient spaces between the yarns and filaments for blood flow via capillary action as discussed herein.

If needed, a simple "J" shape can be heat set into tubular body 12 to aid with introduction into the aneurysm. Agents may also be added to the tube to aid in delivery and/or endothelial cell growth. For example, a hydrophilic coating can be applied to the surface of tubular body 12 to aid in delivery through a microcatheter or a swellable hydrogel infused with drugs can be added to provide medicinal treatment and additional filling of the aneurysm. Another example is a clotting agent which may be added to either slow or inhibit the clotting process or to promote clot formation. Bio-absorbable and bio-compatible fibrous elements such as Dacron (polyethylene terephthalate), polyglycolic acid, polylactic acid, a fluoropolymer (polytetrafluoroethylene), nylon (polyamide) or silk can also be incorporated into the braid, or to the surface, to enhance the ability of the tubular body 12 to fill space within the vasculature and to facilitate clot formation and tissue growth. Similarly, hydrogels, drugs, chemotherapy beads and/or fibers can be added to the inner diameter of tubular body 12 or infused into the walls, yarns, or fibers depending on specific use (for example embolic chemotherapy). On the finishing side of the micrograft (proximal end), a microcoil (not shown) may be added to provide a barrier between the aneurysm sac and the parent vessel. FIG. 1 can include similar features or functions as will be described below.

FIGS. 2A-2C illustrate a micrograft similar to micrograft 10 of FIG. 1 except having a larger diameter and thinner wall. FIG. 2A illustrates the thin walled micrograft 25 crimped in the process described above to forms peaks and valleys resulting in circumferential corrugations or folds. FIG. 2B is provided for illustrative purposes to highlight the peaks and valleys by stretching the tubular body. FIG. 2C shows a portion of the micrograft 25 in the bent position. In some embodiments, the micrograft is pre-set in this bend, e.g., a U-shaped configuration, to improve packing within the aneurysmal sac. As shown, due to the structure of the micrograft, when bent, it maintains its radius in the similar manner to a bent coil. (The micrograft would be delivered in a substantially linear position as described below). As shown, the compression and heat setting (crimping) process creates an "accordion like" structure with peaks 18' and valleys 20'. In FIGS. 2A-2C, the wall of the micrograft 25 is a fine braid, or textile structure, and will approximate a solid structure when placed in direct blood flow, causing high flow disruption. Another feature of the graft is its white color, which may vary depending on PET formulation and processing. If desired, colors other than white may be used to denote different body diameters or transitions in mechanical or therapeutic properties, for example.

Note crimping alters the direction/orientation of the yarns/filaments with respect to a longitudinal axis of the tubular braid. In some embodiments, after crimping, the yarns/filaments are substantially transverse to the longitudinal axis. In other embodiments, the yarns/filaments after crimping are at about 35 degrees to the longitudinal axis, or between about 35 degrees and about 90 degrees. In alternate embodiments, the yarns/filaments after crimping are at about 45 degrees to the longitudinal axis, or between about 45 degrees and about 90 degrees. The effect of crimping is to increase the angle of the yarn or filament relative to the longitudinal axis, i.e., if the uncrimped braid angle is X degrees with respect to the longitudinal axis, the braided angle when crimped is X+Y degrees. In preferred embodiments, Y>5 degrees, although other values of Y are also contemplated. It is understood to those familiar in the art that braid angle relative to longitudinal axis (typically referred to as the alpha (a) angle) is measured while braided structure is in a straight orientation, however, the angle may also be measured between crossing yarns or filaments (typically referred to as beta (I) angle) in which case the value would be double (2× degrees) as exemplified in FIG. 25B discussed below (compare angles B and C).

In relation to braided structures described herein, for example, tubes braided with 16 ends (yarns) and braid angles above 40 degrees (relative to longitudinal axis) become increasingly challenging to process, are much stiffer, and increased friction between the tight braid and mandrel hinders removal of the mandrel from inside the braid. As a result, such braids are typically manufactured with braid angles below 40 degrees. For tubes braided with 12 or 8 ends for example, the typical maximum a braid angle is even lower, around 30 degrees. Crimping, therefore, as disclosed herein, as a secondary process, allows increase of PPI and braid angle while maintaining softness/conformability/flexibility.

Crimping increases the amount of thrombogenic (fiber) surface exposed to the body. That is, crimping increases the amount of fiber material per unit length as the length of the braid decreases and the diameter increases. In some embodiments by way of example, the length of the tubular body can decrease as a result of crimping by about 50%, although other decreases in length are also contemplated.

Figure 4E:
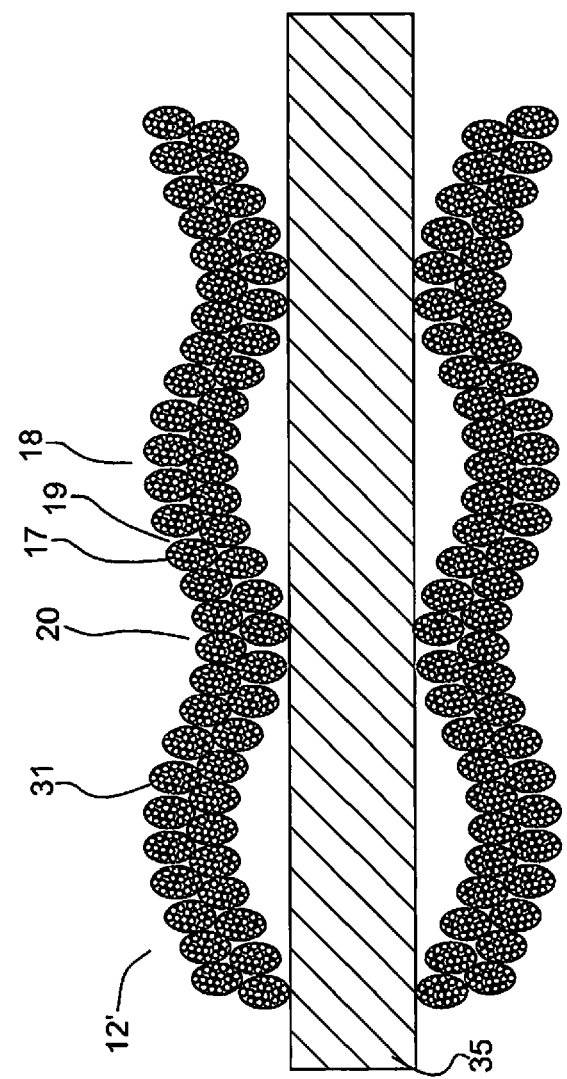
FIG. 4E is a cross-sectional side view of the micrograft of FIG. 4A after crimping.
Figure 4I:
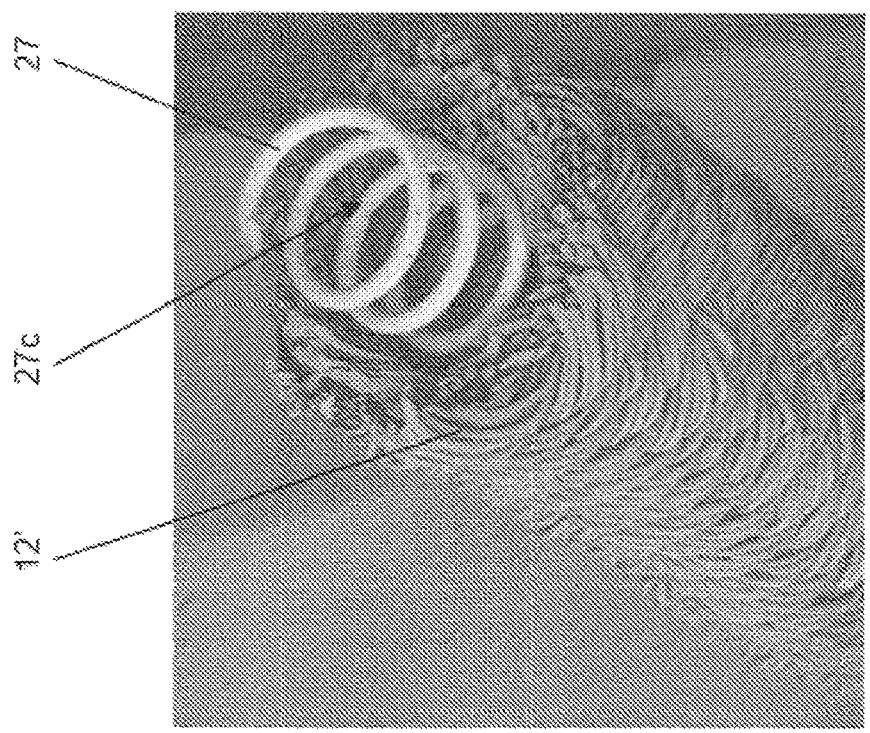
FIG. 4I is a bottom perspective view of the micrograft of FIG. 4A with the braid cut to illustrate the inner coil.
Figure 4H:
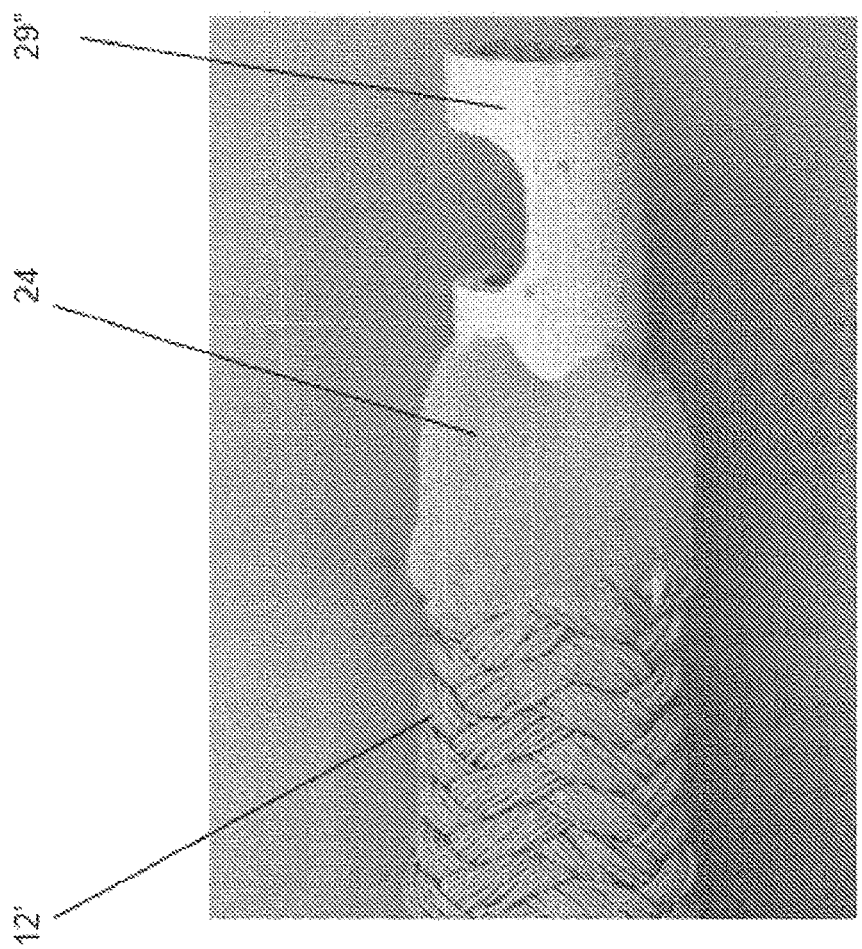
FIG. 4H is side view of the proximal portion of the micrograft of FIG. 4A with an alternate tube.
Figure 4K:
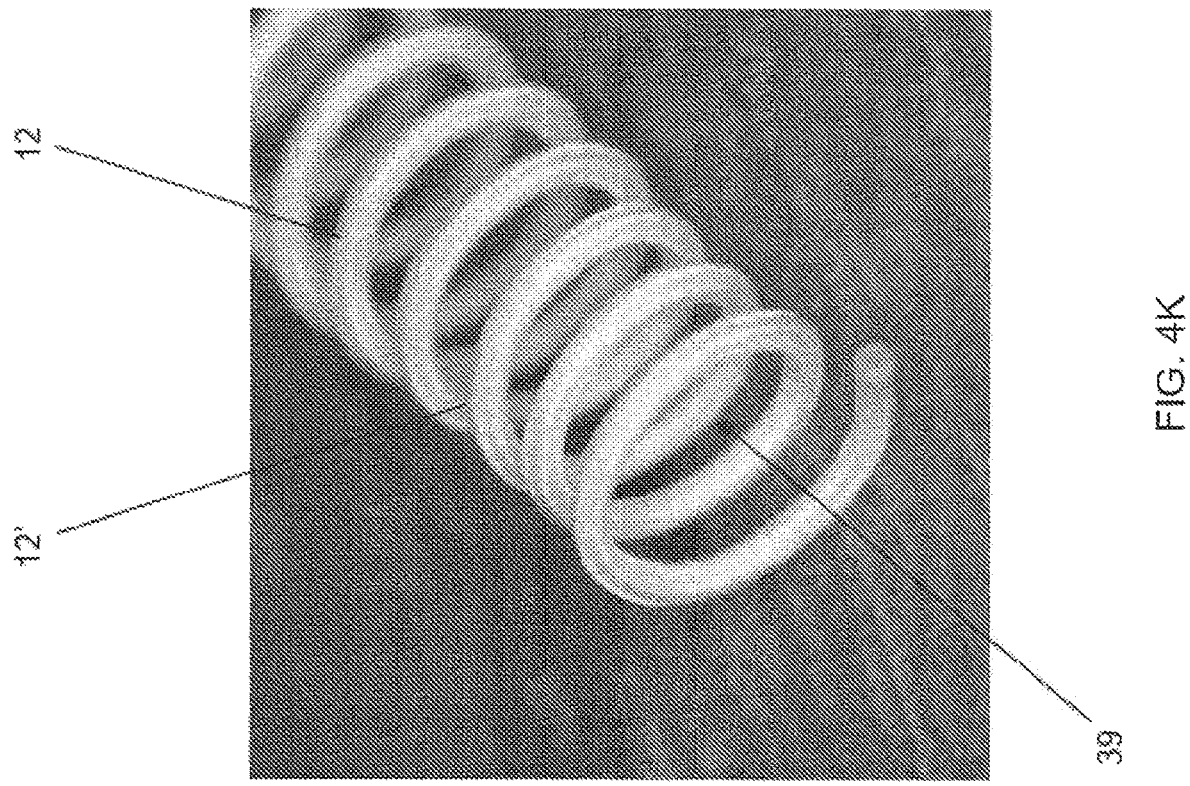
FIG. 4K is a perspective view of the micrograft of FIG. 4A formed in a secondary helical configuration.
Figure 4J:
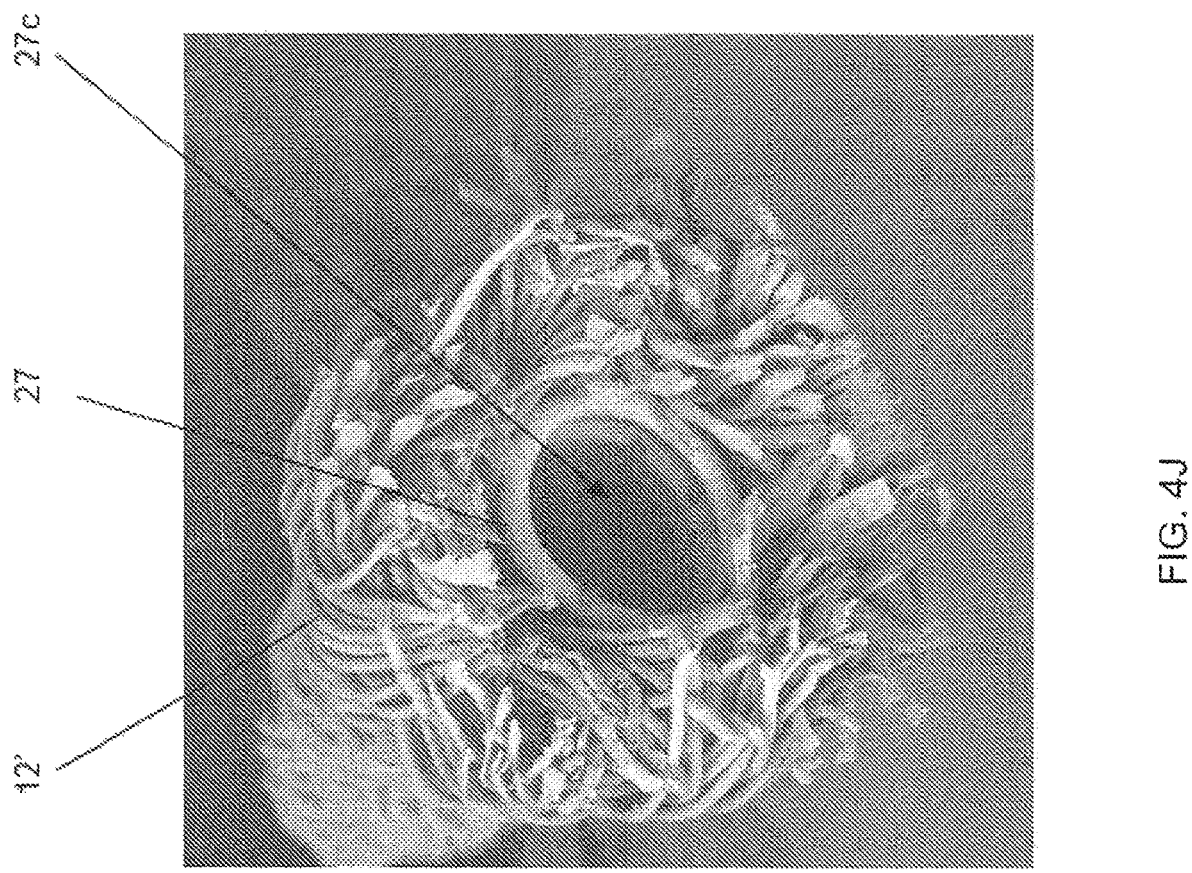
FIG. 4J is a front perspective view showing the inner coil within the braid.

FIGS. 4A, 4B, 4D and 4E-4M show an alternative and preferred embodiment of the micrograft, designated generally by reference numeral 10'. Micrograft 10' is similar to micrograft 10 as it formed from a braided tube 12' and has the same features and functions of tube 12 as well as can include any of the alternate braid constructions described herein. Thus, the various descriptions herein of the filaments, yarns, capillary effects, shape set, etc., are fully applicable to the micrograft 10' of FIG. 4A. However, micrograft 10' has a core element 27, preferably formed by a helical coil, having a lumen for blood flow in the aforementioned capillary effect. The coil is formed into a helical shape and has a proximal end 27a (FIG. 4F) and a distal end 27b. Lumen 27c extends through the coil 27 from the proximal end 27a to the distal end 27b. In a preferred embodiment, the coil 27 is composed of a metal such as platinum or a platinum tungsten alloy. In manufacture, the textile structure in the form a tubular braid 12' is positioned over the coil 27. That is, the braid is formed separately into a tubular shape with a lumen or longitudinally extending opening 39 extending from the proximal end to the distal end for receipt of the coil 27. The braid 12' is preferably composed of PET or other thrombogenic material. The braid 12' can be in the forms disclosed herein and is preferably substantially a closed cell design to provide a large percentage of outer surface area for contact with the blood and/or vessel/aneurysm wall. However, although generally a closed cell design, it has spaces between the yarns and filaments as described herein to enable blood flow into and/or through the device. Such flow achieves the capillary effects described herein. This configuration promotes tissue ingrowth in a relatively short amount of time, and in some instances within 30 days of implantation. The micrograft 10', with braid 12' and attached inner coil 27, is formed into a helical coil shape as shown in FIG. 4K with a lumen 39 extending along its length.

Figure 26B:
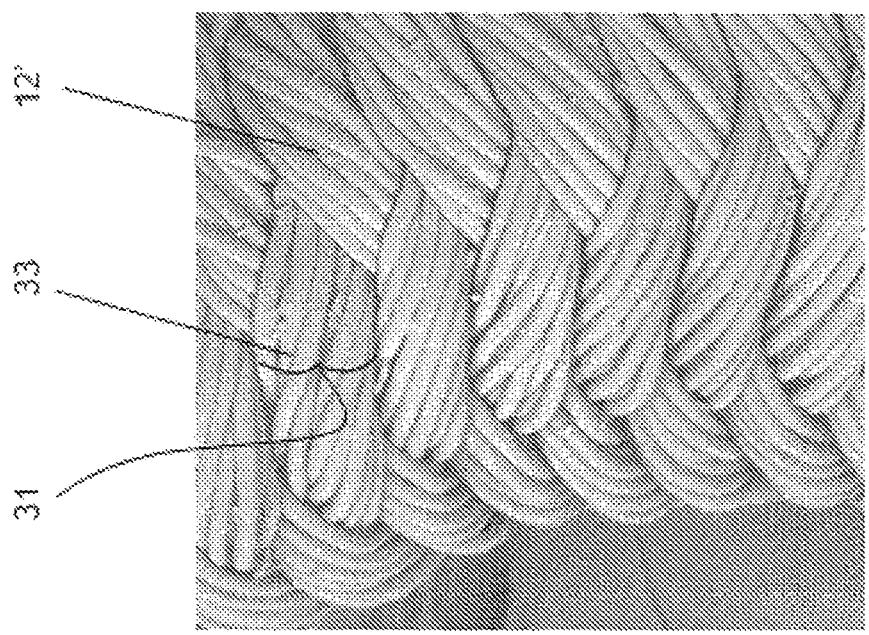
Figure 26A:
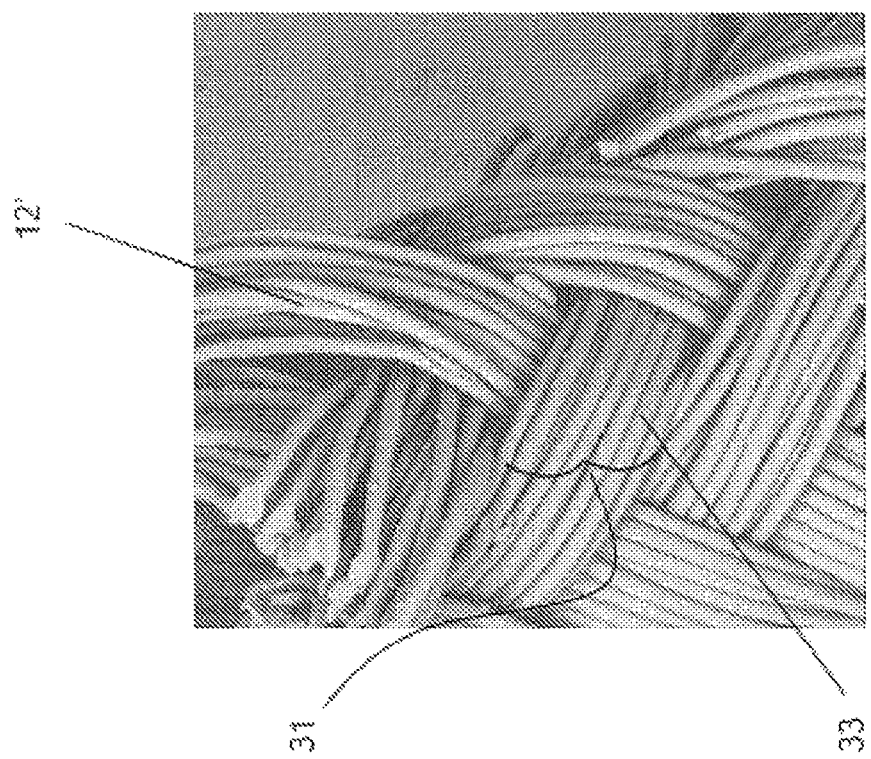
Figure 27B:
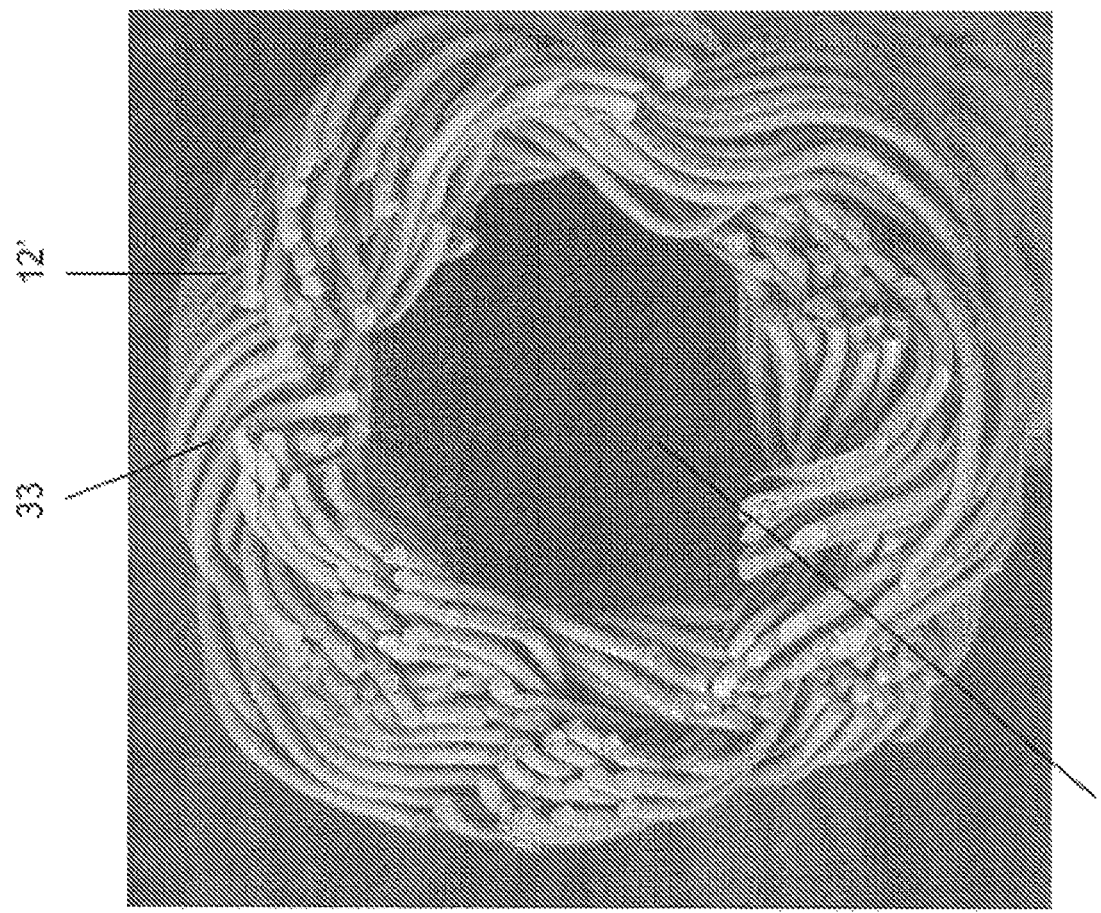
Figure 27A:
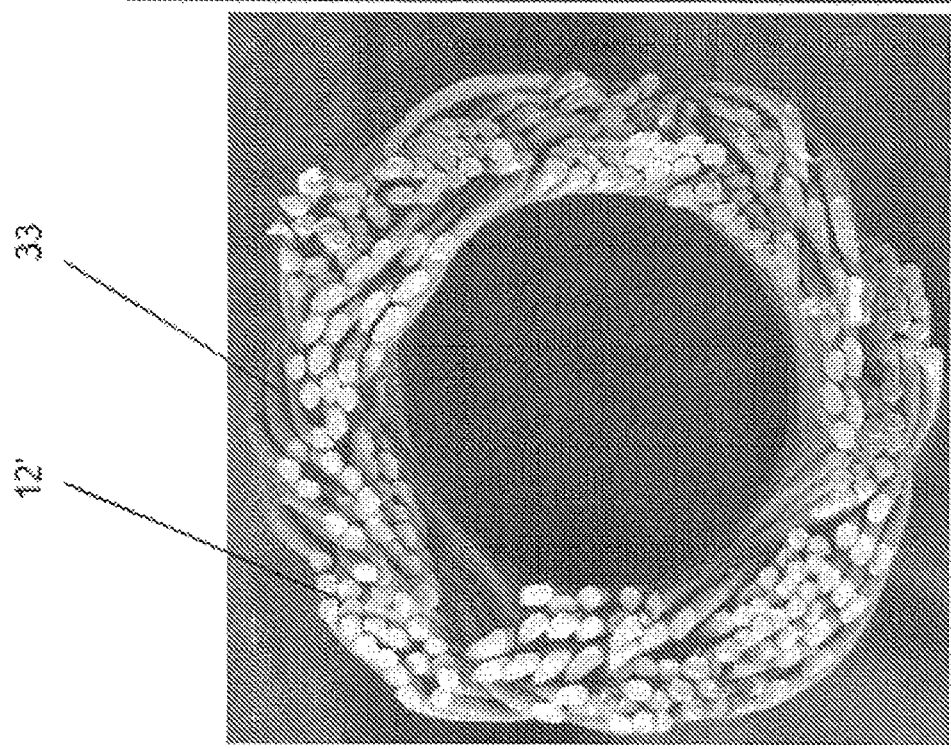

As discussed herein, the braid is preferably crimped to increase the braid angle and increase softness, compressibility and amount of thrombogenic surface area in the device. The structural effect of such crimping can be appreciated by the comparative views of FIGS. 25A-28B. FIGS. 25A and 26a show the braid 12' before crimping wherein the braid 12' has an angle A with respect to the longitudinal axis L of the tubular braided textile structure 12'. FIGS. 25B and 26B illustrate the braid 12' after crimping where the braid 12' has an angle B with respect to the longitudinal axis L of the tubular braided textile structure 12' which is greater than angle A. Angle C of FIG. 25C depicts the alternate way to measure braid angle by measurement between crossing filaments.

Figure 4L:
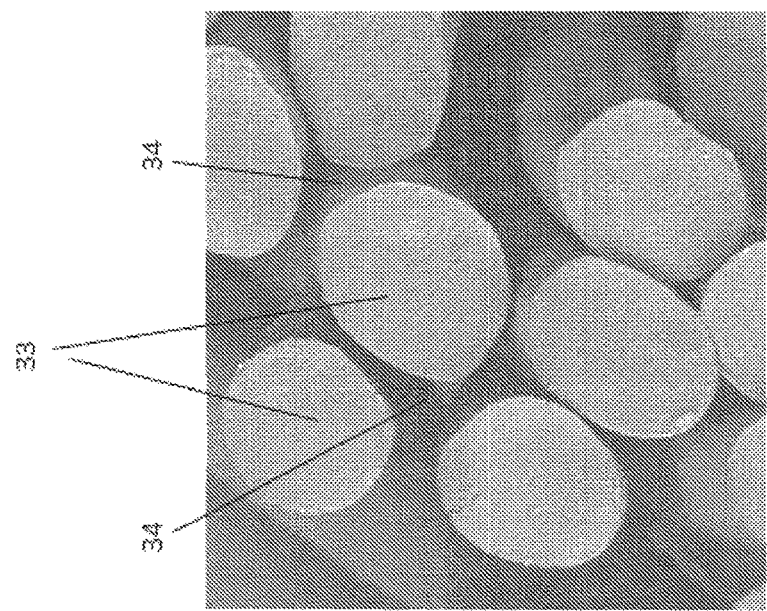
FIG. 4L is a close up view of a transverse cross-section of the filaments of FIG. 4A.
Figure 4M:
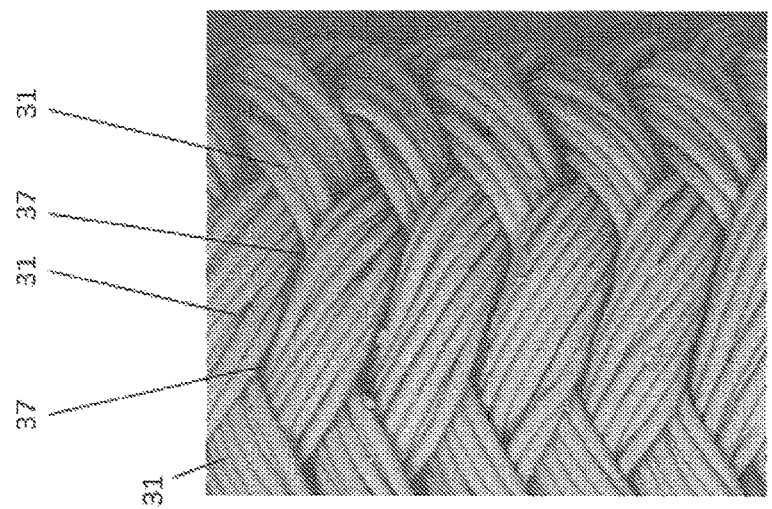
FIG. 4M is a close up view of the braid of FIG. 4A.

The aforedescribed spacing between the filaments and yarns, and the resulting capillary effects can be appreciated with reference to FIGS. 4L and 4M. Filaments or fibers 33 have spaces or gaps (voids) 34 therebetween for blood absorption and flow. Yarns 31 (fiber bundles) composed of filaments 33, have spaces or gaps (voids) 37 therebetween. These create the aforedescribed first and second capillary effects. The longitudinal opening 27c extending through the braid inner coil 27 and overlying braid 12' (FIG. 4J) creates the third capillary effect described above.

This configuration of the embodiment of FIG. 4A also encourages rapid blood clotting and in some instances clotting can occur immediately upon implantation. In fact, in this configuration, when the micrograft (implant) 10' is held in the delivery system within the vessel/aneurysm but prior to release from the delivery system, the micrograft 10' becomes filled partially or entirely with blood so that blood stagnation can commence even before the micrograft 10' is released and implanted, thereby expediting thrombus formation. Saturation of the micrograft in the delivery assembly and once implanted accelerates and/or improves thrombosis.

Note the braid fibers are not only thrombogenic (attract blood platelets and proteins which promote clot) due to their material, e.g., PET can be used as the filaments or as a thrombogenic surface, but also promote stasis as the braid structure traps blood.

In the embodiment of FIG. 4A, a tube 29, preferably composed of Nitinol, although other materials can be utilized, is seated within proximal coils of the helical core element (coil) 27, preferably screwed or twisted into the proximal coil windings of the helical core element 27 to provide structure for engagement with a delivery device. The braid is melted onto tube 29, with region 24a showing the melted fibers, to attach the tube 29. As illustrated, the tube 29 (and tube 29' 29", 29"') extends proximally of the core element 27. It also extends proximally of the tubular textile structure 12' so a proximal region is exposed for engagement by a delivery member. A distal portion of the tube 29 is within the tubular textile structure. The formation of threads in the tube 29 for attachment to the core element windings allows the textile structure, e.g., braid, to melt into the threads, thereby further stabilizing/reinforcing the attachment of the outer textile structure 12 to the inner elements. That is, the cut feature in the tube 29 provides a better joint (increased bond strength) between the textile structure 12' and the tube 29 as the melted material (textile structure) flows into the spaces between the threads. It is contemplated that instead of threads, laser cut holes or tabs or other engagement features can be provided to attach the tube to the inner (core) element by screwing into, pressing into or other methods of interlocking. That is, these engagement features, e.g., cut features or surface gaps, can be used instead of threads for twisting into or other attachment of the tube to the proximal coils of the core (inner) element and such features can also be provided to receive the melted material (textile structure). It is also contemplated that other laser cut features such as holes or surface gaps can be made in the tube to provide additional spaces for the melted material to increase the strength of the attachment These additional spaces can be in addition to the features for attaching the tube to the inner element. In some embodiments, tube 29 has a deflectable tab 29a and a window 29b to receive a delivery wire as described below in conjunction with the delivery method. The tab 29a is biased to the aligned position of FIG. 4B and is moved to an angled position to receive the wire through the window 29b, the tab 29a providing an engagement/retaining structure for engagement with a wire of a delivery system described below. Region 24b (FIG. 4F) illustrates the region at the proximal end where the fibers of braid 12' are melted onto the proximal end of coil 27. Note in FIG. 4F an alternative tube configuration is illustrated, with tube 29' having a slot to receive a ball or hook as in FIG. 22A. In FIG. 4G, electrolytic detachment of the implant is disclosed with wire 230 held within tube 29" by epoxy 232 or other material to which it is attached, e.g., glued or fused. The material 232 provides an insulator to ensure the wire 230 is not in contact with the tube 29". In FIG. 4H, another embodiment of the tube 29"' is illustrated. Except for the tube 29', 29", 29"' and electrolytic detachment, the micrografts of FIGS. 4F-4H are identical to micrograft 10' of FIG. 4A. Tube 29', 29" and 29"' can be screwed into the coils of core element 27 in the same manner as tube 29. It should be appreciated that tubes 29', 29", 29"' (and electrolytic detachment) can be used with the braid of FIGS. 4A-4M as well as with any of the other micrograft and braid or textile structure embodiments disclosed herein.

As noted above, braid (braided tube) 12' is made up of yarns 31 each containing multiple fibers 33. When removed from the braider, the yarn(s) 31 of tube 12' will lay relatively flat with the fibers 33 bundled horizontal and spaced apart (see FIG. 4D showing tube 12' positioned over mandrel 35). FIG. 4E illustrates the braided tube 12' which has been crimped over mandrel 35 to create crimped braided tube 12' prior to formation into the structure of FIG. 4A. This is also described below in conjunction with the method of manufacture. When the braid 12' is fixed to the mandrel 35 (FIG. 4D at one or more points and a longitudinal force is applied to the braid, the fibers 33 in the yarn 31 will move closer together and bundle vertically creating micro peaks 17 and micro valleys 19 between peaks 17 (FIGS. 4E and 25B) and corresponding macro peaks 18 and macro valleys 20 along the tube length creating a sinusoidal shape (FIGS. 4E and 28B). (The peaks and valleys of the FIG. 1 embodiment disclosed herein can be formed in a similar manner). The extent of the peaks and valleys is dependent on the amount of force applied and the desired amount of softness. The tube can be completely crimped or selectively crimped at intervals along its length.

In an exemplary embodiment, the inner diameter of the tubular braid 12' is preferably about 0.003" to about 0.012", and more preferably about 0.007". The coil 27 can have an inner dimeter of about 0.002" to about 010". In some embodiments, the coil can have an inner diameter between about 001" to about 0.002" less than the inner diameter of the braid. In other embodiments, the coil can have an inner diameter greater than the inner diameter of the tubular braid since the braid expands in diameter upon crimping.

In the alternate embodiment of FIG. 4C, instead of a locking tab, a marker band 22' is attached to the tube to provide retention structure for engaging structure on the delivery wire. In all other respects, the micrograft of FIG. 4C is the same as the micrograft 10' of FIG. 4A and has therefore been labeled with the same reference numerals.

As noted above, the braid of the implant is preferably non-expandable. That is, after formed, a dimension measured through a transverse cross-section of the implant (braid and coil) is the same in a delivery position within a delivery member as in the placement position. The implant, however, may be stretched to a reduced profile position for delivery and then released for placement to assume its coil shape discussed above. However, when it moves from the delivery to the placement position, the braid does not expand. The change is to the implant (braid and coil) from the linear shape within the delivery member to its secondary helical shape within the body, but the combined thickness of the braid and coil (i.e., the outer diameter of the braid) remains constant during delivery and placement. This is in contrast with expandable braids wherein the diameter of the braid increases when exposed from the delivery member and in the placement position. As discussed herein, such expansion increases the inside diameter of the braid and at least in initial expansion or expansion to a certain percentage, can increase pore size (openings) in the braid.

The method of manufacturing the implant of FIG. 4A will now be described. Note in the method, the braid is formed separately into a tubular form and then the coil is positioned within the braid before heating and melting of the braid onto the coil. Thus, as can be appreciated, the braid is not wound onto the coil but is formed separately and the two elements/components (structures) subsequently attached.

Set forth below is one example of a manufacturing method that can be utilized to make the vascular implant (micrograft) of FIG. 4A, it being understood that other methods can also be utilized. Additionally, different implant structures are disclosed herein which could entail other manufacturing methods. The steps of an exemplary manufacturing method are as follows:

1) The braid (formed by the aforedescribed filaments) is formed on a mandrel. Note the braid in a preferred embodiment is composed of PET, although as noted above, other materials are contemplated. (Note that as discussed herein, the textile structure can alternatively be in the form of a woven textile structure, an electrospun structure formed from one or more polymeric fibers, or other overlapping fiber arrangements/structures formed into a tubular shape as in step 2 below).
2) The braid is relaxed and annealed to set into a tubular shape (tubular structure).
3) After cooling, the tubular braid is compressed on the mandrel to crimp the braid, increasing the amount of fiber per unit length and/or in certain embodiments forming peaks and valleys as described above. Note when the tubular braid is compressed, the inner coil is not within the braid, so that the crimping does not affect the coil.
4) The tubular braid is heated again to set in the compressed state.
5) After cooling, the braid is removed from the mandrel to ready for attachment to the inner element, i.e., the metallic coil.
6) The metallic coil is formed by winding a wire about a mandrel into a helical shape, and the opposite ends of the coil wire are attached, e.g., glued, in tension around the mandrel. The tensioned metallic coil is positioned within the tubular braid, i.e., inserted into the tubular braid or the tubular braid is slid over the tensioned metallic coil, which in either case means the metallic coil is "insertable into" the braid. Note in this tensioned position, the metallic coil is tightly wound around the mandrel and of a reduced height (the height defined as the diameter or transverse dimension measured from a topmost point along the length to a bottommost point along the length of the coil). As noted above, the coil wire in a preferred embodiment is composed of platinum alloy for radiopacity, although other radiopaque materials can also be utilized.
7) Once within the tubular braid, the attached glued ends of the tensioned coil are cut, causing the coil to slightly spring back and unwind, resulting in some expansion (increase in overall coil diameter) toward the braid, with portions of the coil coming into contact with the braid. Note in some embodiments, only some contact portions of the coil come in contact with the tubular braid, with other portions of the coil not in contact with (spaced from) the braid. An example of this is shown in the cross-sectional view of FIG. 4F wherein the contact portions are only at the proximal and distal end 27a, 27b. In other embodiments, more portions come into contact with the tubular braid. In some embodiments, since the tubular braid has peaks and valleys due to crimping, the coil wire 27 comes into contact with some or all of the inner surface of the valleys and not in contact with the peaks. An example of this is shown in the cross-sectional view of FIG. 4G wherein coil 27 contacts the inward portions of the braid 12'.
8) One end of the tubular braid is heated to melt onto the coil to attach the tubular braid and coil (at a melt joint) to form the braid/wire assembly (implant). The mandrel can be left during melting or alternatively removed prior to melting.
9) A filament (yarn or wire) is threaded through the device lumen (so the device is able to slide over the filament) to aid in formation of a second device configuration.
10) The filament (yarn or wire) is wound with the braid/coil assembly (device) on a mandrel or other fixture to a secondary helical shape and then the assembly is heated to set in the secondary shape. In some embodiments, each successive heat treatment is at a higher temperature and/or a longer duration to improve shape retention of that treatment and to control shrinkage of the braid. By controlling previous heating, the final heat treatment can be used to impart the most shrinkage of the braid to aid in setting the secondary shape. In the illustrated embodiment, the secondary shape is a helical shaped, although, alternatively, the secondary shape could be other 3D shapes, such as spherical, conical, etc.
11) The device (attached braid and coil) is removed from the oven to cool and the filament and shaping mandrel/fixture removed, leaving the assembly (implant) in its set secondary shape.
12) A nitinol tube such as tube 29 as discussed above (or alternatively a stainless steel tube) is inserted into the coil at one end of the tubular braid. The tube has a helical feature cut into one end. The tube in some embodiments is attached by rotating or screwing it in between the windings of the coil wire so the helical feature interlocks with the windings. Note that Nitinol provides resiliency which reduces the likelihood to break when acting as a lock component with the pusher of the delivery system. Also Nitinol provides more favorable MRI visualization (less interference). Note although the tube is preferably made of Nitinol, alternatively other materials such as stainless steel can be utilized. Preferably, the inner diameter and outer diameter of the tube is the same or substantially the same as the inner diameter and outer diameter of the coil wire so that the tube and coil wire are substantially flush. However, it is also contemplated, that the coil and tube can have a stepped surface.

13) In the next step, the braid is heated to melt onto the nitinol tube and the end of the coil, thereby attaching the tube to the braid and coil, forming the final assembly (micrograft/implant). Note that in some embodiments, the melted braid region covers the entire region where the helical feature (thread) of the tube and coils of the metallic coil are intertwined. The material flowing into the helical feature reinforces the joint.

Crimping makes the tubular braid softer as there is more room for the tubular braid wall to compress. The increased compressibility enables a higher packing density in the aneurysm, i.e., more implants can be fitted in the aneurysm, and fill a higher volume. The increase in the amount of thrombogenic fiber per unit length of the device is also directly proportional to the amount of crimping (compression) and as stated earlier, depending on the braid filament type or pattern, does not always result in peaks and valleys. It does, however, reduce braid cell size while increasing braid angle and outer diameter. As an example, crimping a tubular braid by 50% (via axial compression) in effect doubles the amount of fiber per unit length in the resultant structure. This can be used to increase the amount of thrombogenic material and surface area in a braided device as a secondary (post-braiding) step.

The sufficiently crimped braids (high braid angle) disclosed herein made with multifilament yarns maintain a closed cell structure on the outer bend surface even if deflected or coiled in a secondary shape. That is, although the tubular braid in its coiled secondary shape will experience compression of the yarns/filaments on the inside of its bend radius and stretching/expansion of crimped yarns on the outside of the bend radius, it still does not allow visibility of the internal coil through the braid surface. In other words, the crimped braid will maintain its closed cell configuration in the linear as well as in a non-linear, e.g., bent or curved or coiled, configuration. In contrast, for un-crimped and monofilament tubular braids, the inside bend surface will experience compression and a reduction in cell size and porosity whereas the outer bend surface will experience cell/pore size increase (resulting in open cell structure).

As can be appreciated, in the exemplary embodiment, the implant is formed into a secondary shape after insertion of a filament through the device lumen. Also, as can be appreciated, the inner coil is released from a tensioned positioned once inside the tubular braid to move to its less tensioned more relaxed position. In this position, in some embodiments, portions of the coil may remain out of contact with the braid.

By crimping the braid without the internal coil, avoidance of compression of the coil is achieved, which due to different heat set temperatures of the braid and coil materials, could result in the coil not being shape set to a shorter length and remaining in tension relative to the braid. Also, since crimping increases the inner diameter of the braid, the inner diameter of the braid can be set and then a coil positioned therein, which in some instances can have an outer diameter larger than the internal diameter of the uncrimped braid. This enables a larger coil to be used. Note in an alternate method, the braid is compressed with a coiled wire positioned inside, but the coiled wire is a closed pitch coil so it is not compressible. In this alternate manufacturing method, the closed pitch coil is mechanically clamped to a mandrel, so that when the braid is crimped, the coil cannot change in length so therefore would not be under tension. Note that in either method, compression of the braid is achieved without compression and tensioning of the inner coil wire. The former method utilizes an open pitch coil which facilitates healing. In yet another alternate method, the braided tubular structure is formed directly over the metallic member whereby releasing the metallic member causes it to expand within the braid.

FIG. 3A illustrates another embodiment of an intra-aneurysmal micrograft. A variable stiffness micrograft 26 with tubular body 28 includes the same features and functions as described above with respect to FIG. 1, or its alternatives, e.g., multifilament yarns, capillary effects, etc. However, in this embodiment, the micrograft 26, after forming and crimping, is wound about a mandrel to form a secondary coil shape as shown. This is also shown in FIG. 16B wherein the micrograft 26 is pictured both after braiding and crimping (still straight) and after it is wound into a coil after formation of such braided and crimped structure. Such helical configuration is also shown in FIG. 4K where a secondary configuration of the micrograft 10' of FIG. 4A is formed. Other micrografts described herein, with the varying features described herein, can also be wound into a coil shape of FIG. 3A if desired. The tubular body 28 of micrograft 26 is composed of a variable stiffness braid having a proximal stiff section 30 and a distal flexible section 32, the varying stiffness achieved in the ways described above. Tubular body 28 also has a primary diameter D. A radiopaque band 36 can be provided to allow visualization under fluoroscopy and is shown in the approximate center of the braid where it transitions in stiffness. The radiopaque band 36 can alternatively be positioned in other locations and multiple bands can be provided. Alternatively, radiopacity can be achieved in the various ways described above.

Device 26 is shape-set with heat in a pre-biased (secondary) helical shape of FIGS. 3A (and 16B). This is the delivered shape-set form of the device 26. This device may not have such pronounced peaks and valleys as micrograft 10 due to the stretching, bending and heating needed to form secondary shapes. However, the original crimping operation induces the desired properties and makes the micrograft more compliant. Partial stretching or partial un-doing of the crimping also results in a braided lumen that is more compliant radially for improved packing.

Although shown helically-shaped, device 26 can be shape set into any complex three dimensional configuration including, but not limited to, a cloverleaf, a figure-8, a flower-shape, a vortex-shape, an ovoid, randomly shaped, or substantially spherical shape. As mentioned earlier, a soft, open pitch coil can be added to the inner diameter of the braid to aid in visualization. If stiffness of such metal coil is sufficiently low, the secondary shape-set of the polymer braid will drive the overall shape of the device. In other words, the secondary shape of the braid molds the unshaped metal coil which normally shape sets at temperatures much greater than the glass transition temperature of polymers.

The micrograft 26 also has frayed end fibers 38 shown on one end of the device. These loose frayed fibers can alternatively be on both ends of the braid, if desired (other micrografts disclosed herein could also have such frayed ends). When these frayed ends come in contact with another braid within the aneurysm sac having the same feature, the mating ends act like Velcro, allowing the micrografts to interlock and move together. For delivery and introduction into catheter, device 26 would be elongated, e.g., moved to a substantially linear configuration, and inserted into a loading tube having an inner diameter of sufficient size to accommodate primary diameter D. An optional filament (not shown) may extend from the proximal end of the braid to allow pinching/anchoring of the micrograft between a stent or flow diverter and the parent vessel wall upon release to obstruct flow at the aneurysm neck. Packaging and delivery is discussed in detail below.

FIG. 3B illustrates another embodiment of an intra-aneurysmal micrograft. Sliced micrograft 40 has a tubular body 42 that can include the same features and functions as described above for the previous embodiments, e.g., multifilament yarns, capillary effects, etc. Tubular body 42 has a longitudinal cut 44 and is shape set to expose its inner surface 46, thereby providing a flared distal end. Micrograft 40 is configured with a portion of the inner diameter exposed to maximize surface area constricted by flowing blood and to aid in movement with blood flow. Device 40 can include a proximal marker band 48 (or alternatively any of the other aforedescribed radiopaque features) for visualization. Holes 50 and 52, formed by laser cut or other methods, provide for communication with the blood. Micrograft 40 is particularly suited for placement at the neck of the aneurysm either manually with a delivery system or through movement with blood flow circulating within the aneurysm. Delivering micrografts 46 to an aneurysm may result in clogging at the neck/stent interface as they get caught up in exiting blood flow and accumulate at the aneurysm neck. This structure can also be a round tube, flattened tube, or other shape that is easily moved by blood flow.

The tubular bodies for the above embodiments have been described as crimped braided tubes, however, the tubes can be made using other manufacturing methods such as weaving, knitting, extruding, or electro-spinning. Structures can also be manufactured with alternating diameters or cross-sections, such as flat to round. In addition, the tube can be made from a rolled sheet or other material formed into desired tubular or substantially cylindrical structures. Structural flexibility can then be adjusted either by crimping or selective laser cutting, for example. If desired, the tubular body can also be flattened to create a thin walled tape or heat pressed to create oval sections.

Also, although crimping, or the use of axial/longitudinal compression and heat is described to produce crimps or peaks and valleys, other manufacturing methods of constructing peaks and valleys can be utilized to achieve similar effects. For example, a wire may be wound tightly around a braid placed on a mandrel. The gaps between windings will create peaks and when the assembly is heat set (with or without longitudinal compression) and the wire removed, valleys will be formed where the wire compressed the braid and peaks where the braid was exposed.

FIGS. 16A through 16C and FIG. 17 illustrate a portion of micrograft 10 tubular body 12 constructed of 20 denier/18 filament polyester yarn. FIG. 16A shows examples of an uncrimped tubular body 171 alongside a crimped micrograft 10 tubular body 12 to illustrate the formed macro peaks and valleys. FIG. 16B shows a crimped tubular body alongside a tubular body that has been shape set into a helical coil 172 post crimping similar to FIG. 3A. FIG. 16C shows micrograft 10 that has fluid 174 which has been drawn into the micrograft via capillary action described earlier. FIG. 17 shows a tubular body with a marker band (stop collar) 22 attached to the body as in FIG. 1.

Turning now the delivery of the micrografts, several embodiments of delivery systems of the present invention are disclosed. Many of the delivery systems enable over the wire insertion which minimizes micrograft snaking inside the catheter as well as enables delivery of longer length micrografts. The delivery systems also enable retrievability of the micrograft after partial deployment, and in some embodiments, even after full deployment.

Turning to a first embodiment and with reference to FIGS. 5A-5D, an intra-aneurysmal micrograft delivery system is illustrated and designated generally by reference number 54. The delivery system is described below for delivering micrograft 10 but it should be understood that it (as well as the other delivery systems described herein) can be used to deliver any of the micrografts disclosed herein. Delivery system 54 includes a pre-loaded delivery wire 62 for carrying the micrograft and a pusher catheter 58, the pre-loaded delivery wire 62 positioned within the pusher catheter 58. Optionally the system could include a loading sheath similar to the loading sheath of FIG. 7 described below which is positioned thereover to retain the micrograft on the delivery wire 62. The individual components of the delivery system can be removed from the packaging during the procedure and assembled by inserting the delivery wire 62 proximally through the catheter 58 creating a junction 57 at the proximal end of the micrograft 10 and the distal end of the pusher catheter 58. Alternatively, they can be pre-packaged with the delivery wire 62 already positioned within the pusher catheter 58 and a protective loading sheath similar to the loading sheath of FIG. 7 positioned thereover to retain the micrograft 10 on the delivery wire 62. This delivery system may be used as a standalone delivery system to access the target anatomy, or with a microcatheter as described below. Any necessary flushing or coating activation can be done per physician's discretion prior to insertion into the patient.

Delivery wire 62 has micrograft 10 mounted thereon at region 56. Delivery wire 62 has a body with a length extending from proximal end 64 to distal end 66 can range between about 20 cm and about 400 cm, and more particularly between about 100 cm and about 300 cm, and even more particularly about 200 cm. Suitable diameters for the delivery wire 62 can range from about 0.0025 inches to about 0.040 inches, and more narrowly between about 0.002 inches and about 0.035 inches. The overall diameter of the delivery wire may be continuous, for example about 0.014" or the wire may taper from proximal to distal direction, for example about 0.007 inches to about 0.003 inches. Other sizes are also contemplated, dependent on the pusher catheter and/or microcatheter ID used for the procedure.

The distal portion 68 of the delivery wire 62 can include a coil and the very distal tip 66 of delivery wire 62 can be bulbous, of increased diameter, or fitted with a marker band or coil. The distal portion 68 of the delivery wire may be radiopaque as well as able to be shape set to aid in tracking, vessel selection, and intra-aneurysm maneuvering. For example the distal portion can be shape set to J-shape as in FIG. 11A described below. The delivery wire 62 may also be coated with a hydrophilic coating. The delivery wire 62 includes a retaining structure such as a tapered region to aid in retention of the micrograft 10 thereon. In alternative embodiments, to further aid retention, or if a delivery wire is utilized which does not have such retention structure such as a standard guidewire, then a protective loading sheath can be utilized. In another embodiment, the micrograft can be mounted using the micrograft introducer system 136 as described below with regard to FIG. 9.

Delivery wire 62 has a tapered region 70 (FIG. 5C) forming an engagement structure for mounting the micrograft 10. A proximal stop collar 22 is positioned over the tapered region 70. The stop collar 22 can be attached to the delivery wire 62 or alternatively and preferably form a retaining feature attached to an internal portion of the micrograft 10. In either case, the proximal end of the micrograft 10 is frictionally engaged and retained by the delivery wire 62. Micrograft 10 is mounted coaxially (and slidably) on wire 62 a distance L from the wire distal tip 66. The distance L is set by the proximal stop collar 22 which interacts with wire taper 70 as shown in FIG. 5C, or other hard stop on the wire (e.g., a marker band), and the overall length of the micrograft. For instance, longer micrografts may have a small distance L. In some embodiments, distance L may be zero and the hard stop may be on, inside or near the distal end of the micrograft 10 to interact with a bump, bulb or head (such has a head 184 of FIG. 5E described below) on the distal end of the delivery wire 62 to prevent the delivery wire 62 from passing through the distal end of the graft. In this instance, the distal tip of the micrograft 10 would be adjacent the distal end of the delivery wire 62 as in the embodiment of FIG. 5E.

FIG. 5C shows an enlarged cross sectional view of the proximal end of micrograft 10 with stop collar 22 engaging tapered region 70 of the delivery wire 62. The stop collar 22 as shown is in the form of a marker band to provide radiopacity for visualization. The wire taper 70 acts as a proximal stop to prohibit proximal movement of the micrograft 10 over the wire 62.

Other ways to couple or mate the micrograft and the delivery wire 62 are also contemplated. As mentioned earlier, proximal and distal Nitinol parts may be added to the micrograft as stops, or other parts and/or features (e.g., platinum marker band, notch, bump, etc.) can be added to the delivery wire to act as stops. In some instances, there may be no stop collar, the stop may be on the distal end of the braid (as mentioned above), the pusher catheter may act as the proximal stop, or the micrograft 10 can be sized to be free to slide across the entire length of the delivery wire, proximal to distal.

The pre-loaded delivery wire 62 may be supplied with one or more micrografts covered by a protective cover such as cover 92 of FIG. 7. This cover 92 has a tapered tip tapering to a smaller outer dimension for introduction into the lumen of a microcatheter or component thereof.

In some embodiments, more than one micrograft can be loaded on the delivery wire. They can be linked together on the delivery wire for delivery using one of the frayed, Velcro-like ends 38 described above with respect to FIG. 3 or inter-connected with assistance of the coaxial delivery wire running through them. That is, the device can in some embodiments be supplied pre-packaged with a plurality of micrografts in line along the delivery wire.

As mentioned above, the delivery system 54 includes a pusher catheter 58 having a lumen through which the delivery wire 62 extends. Pusher catheter 58 includes a catheter body 72 and a Luer lock 74. Catheter body 72 is preferably of a variable stiffness construction with a stiff proximal section, softer mid-section and still softer distal section. Individual sections of the catheter may be made up of polymer tubing with varying durometers to control stiffness, proximal to distal. The body may also be made from a variable stiffness, laser cut tube made of stainless steel alloy or Nitinol, for example. If polymer tubes are used, the catheter may also be a braid or a coil reinforced to keep from ovalizing. A lubricous liner made from materials such as PTFE, ePTFE, or FEP may also be added to the structure.

The outer diameter of the pusher catheter 58 is dimensioned to slide freely inside microcatheters with inner diameters ranging from about 0.008 inches to about 0.070 inches. Catheter body 72 can include a hydrophilic coating on its outer diameter for lubricity. The length of the catheter body 72 is preferably slightly shorter than the delivery wire 62 to allow proximal access to the delivery wire 62, i.e., holding the wire 62, while a micrograft (or multiple micrografts) is loaded on the distal end. The inner diameter of pusher catheter body 72 or the distal end is sized and shaped so that the micrograft 10 cannot be forced inside the catheter body 72 during distal advancement or proximal pulling of delivery wire 62. When loaded in the pusher catheter 58, the delivery wire 62 is preferably free to rotate and to move in a linear (back and forth) motion relative to the pusher catheter 58. Additionally, the pusher catheter 58 can be designed to accommodate delivery of stents or other devices or fluids to the target anatomy. In some embodiments, a clearance between an outer dimension of the delivery member and an inner dimension of the occluding device is substantially fluid-tight before delivery into the aneurysm but sufficient to enable slidable movement of the delivery member with respect to the occluding device.

At or near the distal end of pusher catheter body 72 is radiopaque marker band 76 which can be made of platinum/iridium and attached with adhesive, heat shrink tubing, a swaging process, or other known methods. Alternatively, the marker band can be placed inside the pusher catheter 58 with the delivery wire 62 passing through it. Other suitable radiopaque materials for marker band 76 include gold, silver, and radiopaque shrink tubes, or metal coils for example. A luer lock 74 can be positioned at the proximal end of the catheter 58 and attached to the luer lock 74 is a rotating hemostatic valve (RHV) 78 for saline, drug, contrast media or other fluid introduction though the inner diameter of pusher catheter 58. The RHV 78 also serves as a lock to stop relative movement between the pusher catheter 58 and the pre-loaded delivery wire 62 when the RHV 78 is tightened over (clamped onto) the wire. In some embodiments, the pusher catheter 58 can be delivered pre-packaged and sterile with an RHV as an accessory. In embodiments where a co-axial catheter stent delivery system is used, a pusher catheter may not be required as after stent deployment by the stent delivery catheter, the micrograft loaded delivery wire can be inserted into the stent delivery catheter to deploy micrografts.

As described earlier, the delivery wire 62 may be used as the primary access wire as in conventional guidewires. FIG. 6 illustrates an alternate design to the over-the wire pusher catheter, which is a rapid exchange pusher catheter designated generally by the reference number 80. The rapid exchange (RX) pusher catheter 80 has a catheter body 82 with marker band 76 at a distal end and a stiff push wire 84. Catheter body 82 will share many of the same features as the mid and distal section of catheter body 72 described above, including coating. The stiff pusher wire 84, which may taper, can be made of stainless steel alloy, Nitinol, or other suitable material. The pusher wire 84 may alternately be a hypo-tube, with or without laser cutting, or a wire featuring a non-round cross-section. The device may be supplied pre-packaged and sterile. In use, the RX catheter may be inserted over the delivery wire or guide wire before or after the aneurysm is accessed by the wire.

Figure 5A:
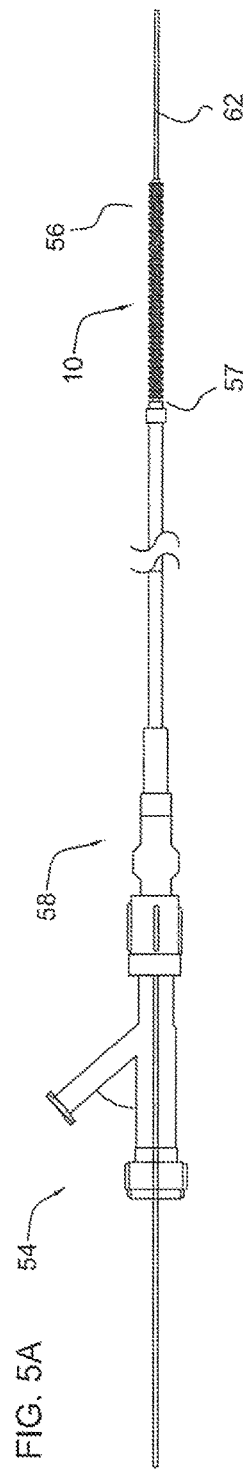
FIG. 5A is a side view of an intra-aneurysmal micrograft delivery system in accordance with an embodiment of the present invention.
Figure 5B:
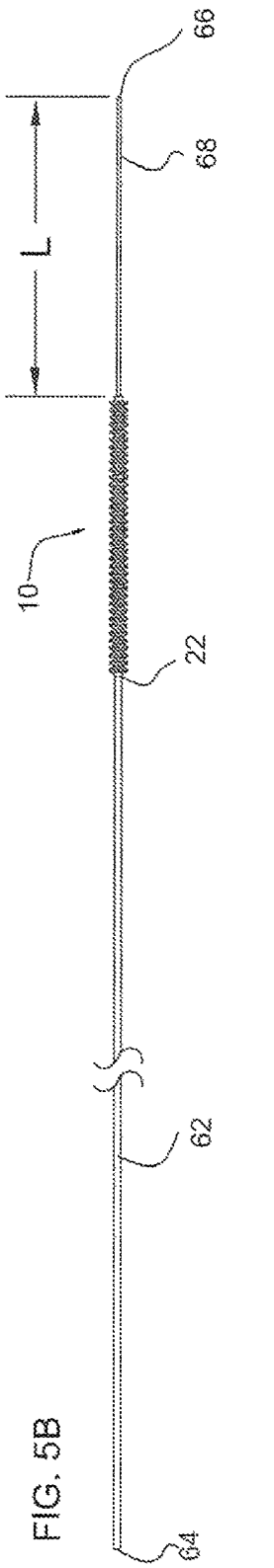
FIG. 5B is a side view of the delivery wire and mounted micrograft of FIG. 5A.
Figure 5C:
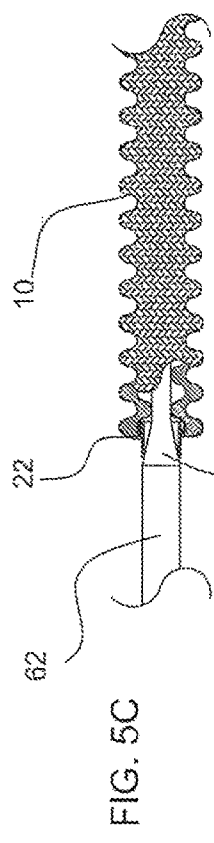
FIG. 5C is an enlarged partial cross-sectional view of the intra-aneurysmal micrograft of FIG. 5B showing the mating of the micrograft with the taper of the delivery wire.
Figure 5D:
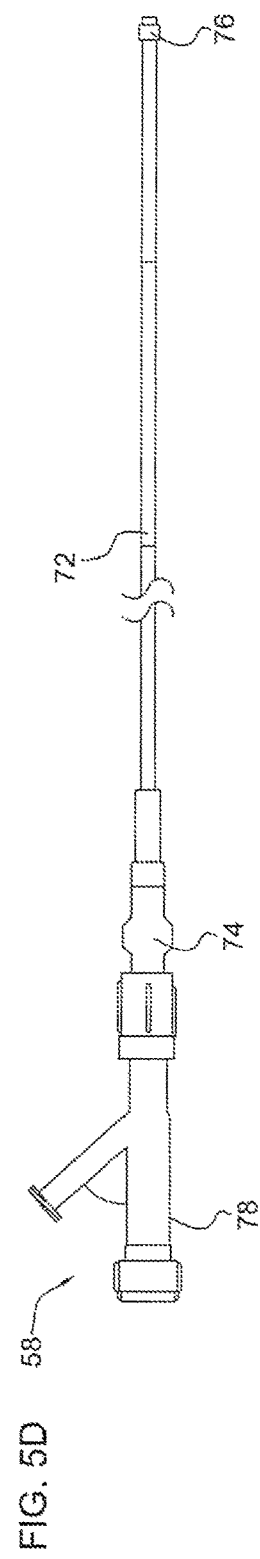
FIG. 5D is a side view of the pusher catheter of FIG. 5A without the delivery wire.
Figure 5E:
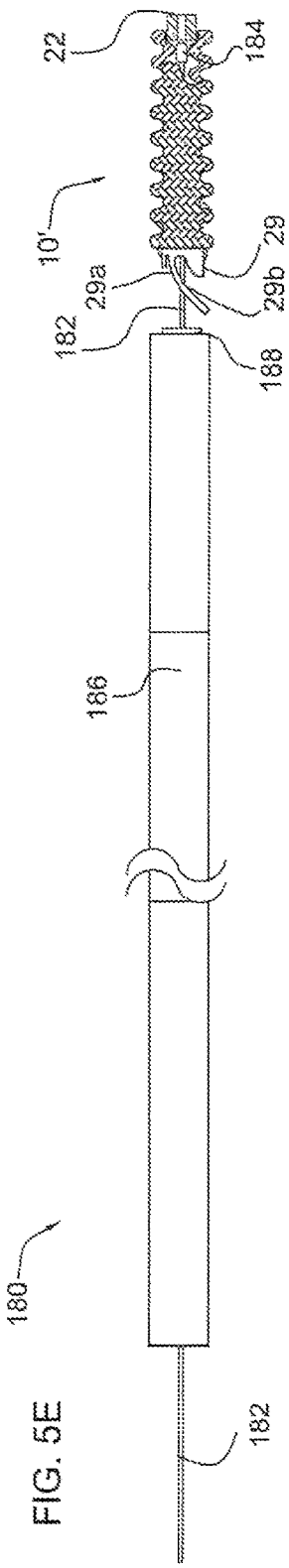
FIG. 5E is a side view of an alternate embodiment of the micrograft delivery system of the present invention.
Figure 5F:
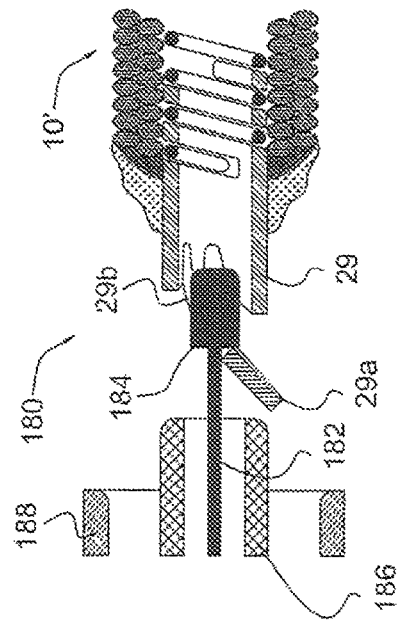
FIG. 5F is an enlarged cross-sectional view of a portion of the delivery system of FIG. 5E shown in the locked position.
Figure 5G:
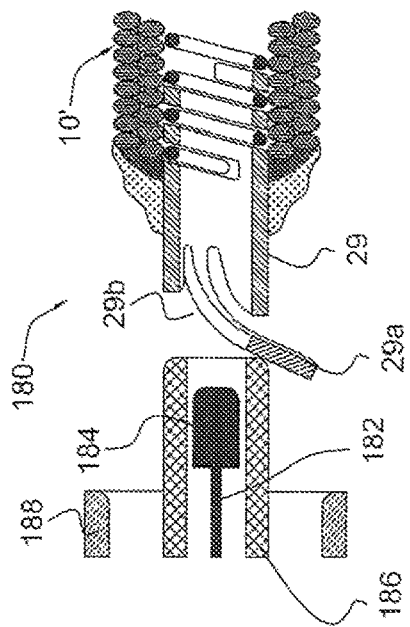
FIG. 5G is view similar to FIG. 5F showing the delivery system in the unlocked position.

FIG. 5E-5G illustrate a delivery system 180 for delivering the micrograft 10' of FIG. 4A. The delivery system has a pusher member 186 and delivery wire 182 with an enlarged head 184. In the initial position of FIG. 5E the tab 29a of micrograft 10' is bent downwardly and the delivery wire 182 passes through window 29b. The delivery wire 182 extends within micrograft 10' to the distal end of the micrograft 10'. In this position, head 184 engages the proximal edge of stop 22, e.g., distal marker band 22, on micrograft 10'.

The pusher member or catheter 186 has an internal stop 188 at its distal end to aid with pushing micrograft 10' as well as to inhibit movement of micrograft 10' into the pusher member's inner diameter. The pusher catheter 186 is shown by way of example without a luer attachment. Both the pusher catheter 186 and the delivery wire 182 may be constructed as previously described. In addition, although not shown, system 180 can include a protective introducer sheath similar to the loading sheath 92 of FIG. 7 to limit micrograft movement as well as to assist in micrograft introduction into a microcatheter.

In the initial position, tab 29a of micrograft 10' is bent downwardly and the delivery wire 182 passes through window 29b (FIG. 5E). The delivery wire 182, as mentioned above, extends inside the graft 10' such that enlarged head 184 comes into contact with the proximal edge of stop 22. Note, although the stop 22 is shown as open, it may be completely closed. Also, the stop may be excluded and the braid may be melted to narrow or close the distal end of the braid to prohibit the wire 182 from exiting. The use of a distal stop also serves the purpose of keeping the micrograft 10' in tension which aids in delivery by stretching and reducing the outer diameter of the micrograft 10'.

Figure 5H:
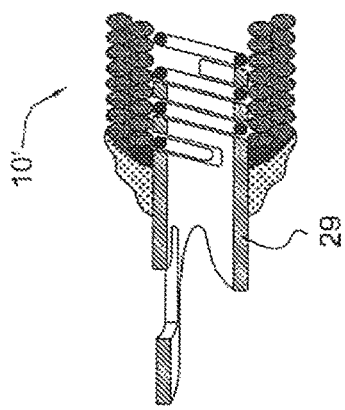
FIG. 5H is a view similar to FIG. 5G showing the delivery system withdrawn and the micrograft fully deployed.

The tab 29a provides a force against the delivery wire 182 to retain the micrograft 10' on the wire 182. Upon delivery, the wire 182 is retracted to the position of FIG. 5F where delivery wire enlarged tip 184 engages the tab 29a. Up to this position the micrograft 10' can be retrieved from the aneurysm and/or maneuvered therein. Next, pusher catheter 186 is advanced (or wire tip retracted) to force the tab 29a to the position of FIG. 5G, therefore enabling full retraction of the enlarged head 184 of the delivery wire 182 through window 29b for release of the micrograft 10' from the delivery wire 182. FIG. 5H shows the tab 29a returned to its original position longitudinally aligned with the micrograft 10' after retraction of the delivery system.

FIG. 7 illustrates another embodiment of an intra-aneurysmal micrograft delivery system generally referred to by reference number 86. Delivery system 86 comprises a pusher wire 88 and a loading tube 92. Pusher wire 88 includes an elongate tapering flexible wire that can be made from stainless steel, or alternatively, Nitinol, plastic or other inert or biocompatible material or combination thereof. Although shown as a wire, the pusher wire can alternatively be a hypo-tube with a Luer lock.

At the distal end of pusher wire 88 are expanding grasper members or arms 94, 98. Although there are four grasper arms in this design, more or less than four arms may be used. The arms 94, 98 can be made of shape set shape memory material such as Nitinol, spring tempered stainless steel, radiopaque metal, or other suitable material. The arms 94, 98 can alternatively be manufactured from a metal or elastic tube which is laser cut to create deflectable arms. Attached to the distal end of one or more of the grasper arms are radiopaque bands (see labeled bands 102, 106, and 108; the fourth band not shown since the fourth arm is not shown). The bands can be attached with glue, solder or other methods. The proximal ends of the arms are attached to the pusher wire 88 by a coil 110 which can be made of wound stainless steel or platinum iridium, for example. Attachment methods may include gluing, welding, or soldering. The use of the grasping arms has the advantage of enabling grasping of the micrograft after full deployment to retrieve/remove the micrograft or to maneuver/reposition the micrograft within the aneurysm as described below.

The pusher wire 88 has a length (including arms) between about 20 cm and about 400 cm, more narrowly between about 100 cm and about 300 cm, for example about 200 cm. Suitable diameters for the pusher wire 88 can range from about 0.006 inches to about 0.040 inches, more narrowly between about 0.008 inches and about 0.035 inches. The overall diameter of the pusher wire 88 may taper from proximal to distal, for example about 0.014 inches tapering to about 0.003 inches. The pusher wire 88, either in part or whole, may be coated with a hydrophilic or PTFE coating for lubricity.

Loading tube 92 is made of either metal or plastic and preferably has distal taper 112 for mating with a microcatheter Luer taper. The loading tube 92 preferably has a length sufficient to cover the entire micrograft 90 and at least a portion of coil 110. The inner diameter of the loading tube 92 is preferably close to the inner diameter of the microcatheter to which it will mate. A range for the inner diameter may be between about 0.008 inches and about 0.070 inches. The loading tube may have a crimp or other fixation method to prevent relative movement to the pusher wire 88. If used on a structure having a Luer or other attachment on its proximal end, the introducer may have a lengthwise slit to aid in removal (i.e., peel-away).

One way to load micrograft 90, which has proximal band 114, e.g., a marker band, is to position the loading tube 92 on pusher wire 88 just proximal to the two pair of grasper arms 94, 98 so that the arms are in their normal expanded position. The band 114 on micrograft 90 is then positioned between bands 102 and 104 (one on each arm of arms 94) and bands 106 and 108 of arms 98. Note to achieve axially spaced bands, the arms 94 can be shorter than arms 98 so the bands 102, 104 are proximal of bands 106, 108, or alternatively, the arms 94, 98 can be the same size and bands 102, 104 can be placed on a more proximal position of arms 94 (spaced from the distal end) while bands 106, 108 can be placed on a distal end or more distal position of arms 98. The loading tube 92 is then advanced forward (distally) compressing the pusher arms 94, 98 to a collapsed or compressed position to engage (grasp) the band 114 to retain the micrograft 90 in place. Thus, band 114 forms an engaging or retention structure for engagement by the pusher (delivery) wire 88 to retain the micrograft 90 on the wire 88.

Note micrograft 90 is similar to micrograft 10 except for the proximal band 114 which is positioned around a portion of the braided structure.

Note alternatively, instead of the micrograft having a single proximal marker band, it may have two proximal bands where the bands of the pusher wire sit to create a lock when compressed inside the lumen of the loading tube. Alternatively, a micrograft with an internal coil may have proximal coil windings spaced to have a gap that allows radial compression and grasping by the bands of the pusher wire.

FIG. 8 illustrates yet another embodiment of an intraaneurysmal micrograft delivery system generally referred to by reference number 116. Delivery system 116 is a neurovascular stent-graft kit that comprises a pusher wire 118 with distal band 120, stent or flow diverter 122 with proximal arms with bands 124 and 126 and distal arms with bands 128 and 130, micrograft 132 with proximal band 134, and loading tube 133. The micrograft 132 is locked proximally by the stent 122 and stent bands 128 and 130 and loading tube 133. Stent or flow diverter 122 is in turn locked to pusher wire 118 using a similar locking concept as bands 124, 126 are blocked by band 120. The number of arms for both locking systems may vary to be more or less than two. Delivery system 116 can also be configured to have a through lumen for guidewire delivery.

The delivery system 116 provides a single delivery system that can deliver a micrograft and a stent that can be combined on site to form a neurovascular stent-graft. Alternately, the stent may be permanently attached to the pusher wire and acts as a temporary stent to push grafts into the aneurysm.

FIG. 9 illustrates a micrograft introducer system 136 which may be used to mount micrografts on a delivery wire or on a guidewire before or during a medical procedure. Micrograft loader introducer system 136 comprises introducer sheath 138 loaded with micrograft 10. The introducer sheath includes tubular body 140, Luer lock 142, and stop tube 144. Tubular body 140 can be made of metal, plastic or a combination of materials and sized with an inner diameter between about 0.008 inches and about 0.070 inches and a length that covers all or substantially all of the micrograft 10. The distal tip of the tubular body 140 may be straight or tapered to help in micrograft introduction and handling. The Luer lock can be attached to an RHV such as RHV 78 of FIG. 5D for the introduction of fluid such as, saline or contrast media, guide or delivery wires and pusher catheters. The stop tube 144, which is optional, has a through lumen and can be made of plastic or metal and may have a taper proximal to distal. The purpose of the stop tube is to prohibit the micrograft from exiting the tubular body 140 prior to loading and may be removed prior to insertion.

Although FIG. 9 shows only one micrograft, multiple micrografts may be delivered in a single introducer sheath. They may be free to move relative to one another or linked together using the frayed ends method, for example, as described above. Micrografts having secondary shapes will generally be linear or straight when loaded into the introducer sheath such that they are concentric.

Introducer system 136 is delivered pre-packaged and sterilized. Once opened, an RHV and syringe may be attached to the Luer to introduce fluids. A delivery wire or guidewire may be pushed into the introducer sheath 138 to mount the micrograft(s) on the wire or alternatively the introducer sheath 138 may be mated with the proximal end of the microcatheter and the micrografts may be pushed proximally through the sheath 138 and into the microcatheter using a pusher catheter, with or without a wire, or with a commercially available pusher wire.

The micrografts disclosed herein can be preset to a non-linear configuration and advanced to the aneurysm in a substantially linear configuration and then return to the same non-linear configuration or different non-linear configuration when delivered into the aneurysm, depending on the space within the aneurysm.

Figure 11A:
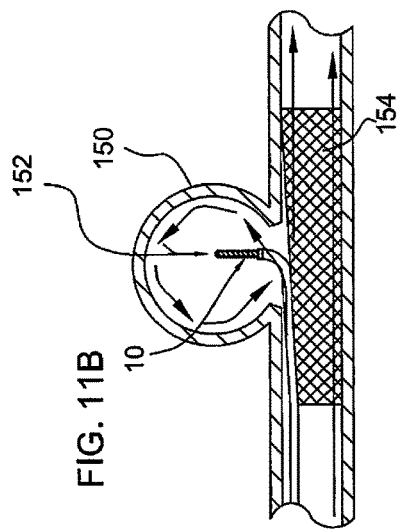
Figure 11B:
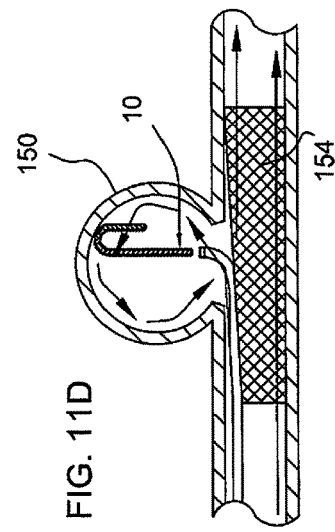
Figure 11C:
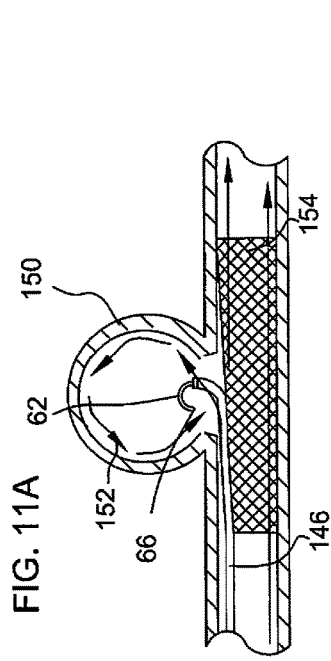
Figure 11D:
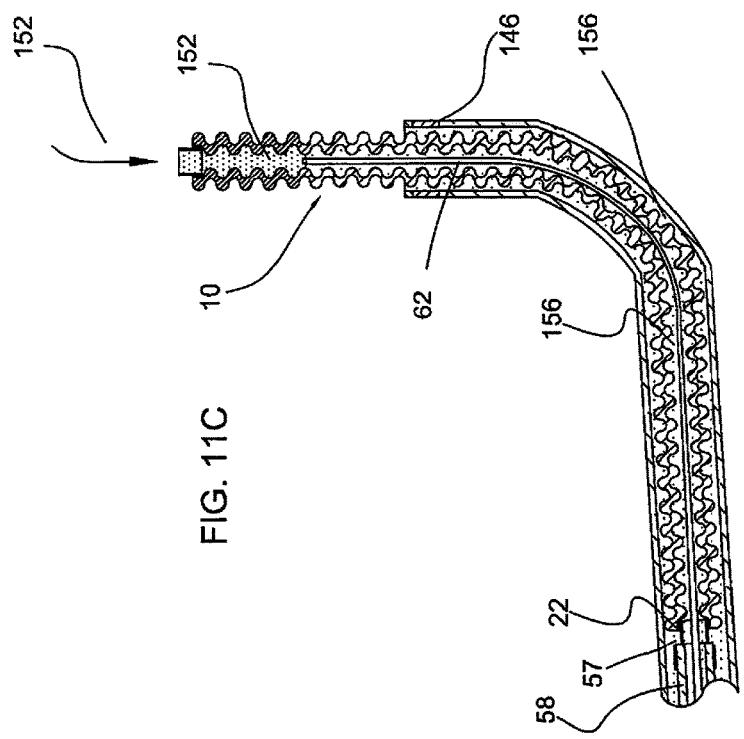
Figure 11F:
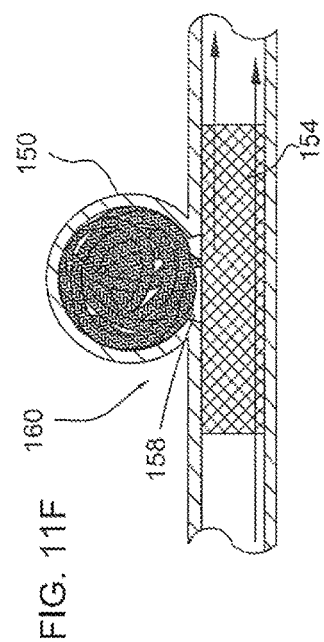

FIGS. 10 through 11F show the preferred method of using intra-aneurysmal micrograft delivery system 54 of FIG. 5A to deploy micrograft 10 of FIG. 1. (Other micrografts described herein can be inserted in a similar fashion). The micrograft delivery method, as well as the "viscosity lock" function (described below) are depicted in flow chart form in FIGS. 18 and 19. Before implantation, the delivery system may be prepared prior to patient insertion as described above or as preferred by the physician.

Typical intracranial aneurysm access requires inserting a guide catheter into the femoral artery and then tracking a microcatheter in combination with a primary guidewire through the vasculature until the aneurysm site is reached. Once there, the primary guidewire is removed and replaced with an embolization system. FIG. 10 shows micrograft delivery system 54 of FIG. 5A being inserted as a unit into the proximal end of microcatheter 146 (with attached RHV 148), the microcatheter 146 having been inserted through the guide catheter and advanced to the aneurysm site and the primary guidewire removed.

FIG. 11A illustrates the distal tip 66 of delivery wire 62 exiting microcatheter 146 that has been positioned inside aneurysm 150 and is held in place using a "jailing" stenting technique, surrounded by blood 152. Jailing refers to the use of a stent or flow diverter 154 to pin the distal tip of the microcatheter between the parent vessel intima and the stent or flow diverter 154, so that the microcatheter tip is held within the aneurysm and delivered occluding devices, e.g., micrografts 10, are kept out of the parent vessel lumen. Other techniques that may be used instead of jailing include temporary stenting and balloon remodeling. It is also contemplated that the micrografts of the present invention be deployed without the use of such parent vessel support (stent or flow diverter) devices.

Once the system is in place as shown in FIG. 11A, the exposed delivery wire tip 66, which has the pre-bent curve as shown, is slowly retracted into the micrograft 10. The retraction can be done in incremental steps of a few centimeters or completely until it reaches a location at, or near, the pusher/micrograft juncture 57 (see FIG. 5A). As the delivery wire 62 is retracted proximally toward junction 57, blood 152 will be drawn into the micrograft's inner lumen to fill the volume previously occupied by the delivery wire 62, as depicted in FIGS. 11B and 11C. This filling action occurs through a combination of the unique internal capillary features of the micrograft described earlier and due to a syringe-like "piston" effect of the receding wire.

With the delivery wire 62 pulled back and in some embodiments pulled back to a locked position against tab 21a, as in the embodiment of FIG. 5F, the micrograft 10 can be pushed forward off the wire 62 and into the aneurysm as illustrated in FIG. 11D using the pusher catheter 58 (FIG. 5A) as it is advanced distally and engages the proximal end of the micrograft 10. Note that if the delivery system does not feature a mechanical lock physically connecting the pusher catheter 58 or delivery wire 62 to the micrograft 10, the micrograft 10 may still be retrieved due to a "viscosity lock" (described below) that is formed inside the microcatheter 146, between the delivery system components and micrograft, once surrounded by a viscous liquid (e.g., blood). This lock allows the micrograft 10 to be advanced and retracted while the proximal end of the micrograft 10 remains inside the lumen of the microcatheter 146 until desired placement is achieved.

Micrograft 10 is pushed forward by pusher catheter 58 and the wire 62 can be pulled further proximally to junction 57, if it is not positioned there already. Once the wire 62 reaches junction 57, the inner lumen of the micrograft 10 will be completely filled with blood 152 that displaces the wire 62 and with any liquid that has been present (e.g., contrast). Since blood now fills the inside lumen of the micrograft 10 and has already permeated the braided walls via the aforedescribed capillary action, the saturated device is composed in part of the patient's blood. Thrombosis and cell in-growth through the microporous yarns will be accelerated as the blood becomes trapped and stagnant within the micrograft (implant) after delivery.

Note that blood can enter the lumen of the micrograft 10 through a distal opening of the lumen and/or through other intermediate or proximal regions of the lumen spaced from the distal end as blood is absorbed through the braided structure. As blood enters such intermediate or proximal regions, it spreads in various dimensions as well as is directed proximally due to the aforedescribed capillary action.

Figure 11E:
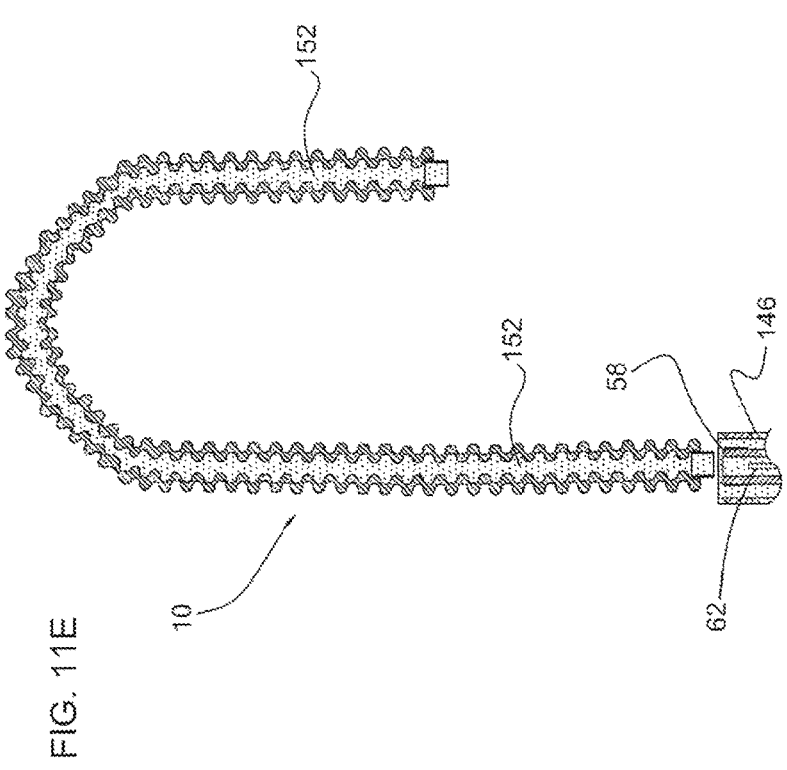

As the micrograft 10 is deployed into the aneurysm, it will take on any preset secondary shapes and random shapes due to contact with aneurysm walls or the stent/flow diverter 154, as shown in FIGS. 11D and 11E. That is, in these Figures, micrograft 10 has a pre-set U-shape as shown, however, this shape can change as it contacts the aneurysm wall and/or stent 154. If the proximal end of micrograft 10 remains inside the microcatheter, the micrograft 10 can be retracted and repositioned at any time prior to full deployment as described above. The micrograft 10 will be fully deployed and disengage from the delivery system once the distal tip of the pusher catheter 58 reaches or exits the distal end of the microcatheter 146. FIG. 11E shows an enlarged cross section of the fully deployed pre-shaped blood filled micrograft 10 of FIG. 11D.

After the first micrograft 10 has been deployed, the delivery wire 62 and pusher catheter 58 are removed and, if needed, another micrograft 10 is loaded on the wire 62 or a new delivery system is opened, and the deployment process is repeated as described above. Multiple micrografts can be deployed by repeating the above steps until the aneurysm is sufficiently packed (per physician discretion) as shown in FIG. 11F. If needed, the microcatheter tip or the delivery wire 62 can be used in between packing or during packing to move or compress micrografts within the aneurysm. Once the aneurysm is sufficiently packed, the microcatheter is removed and the stent or flow diverter 154 continues to expand to cover the neck of the aneurysm 158 to thereby block exit of the micrografts 10 from the aneurysm sac. Together, micrograft 10 and stent or flow diverter 154 form neurovascular stent-graft 160, as shown in FIG. 11F.

As mentioned above, delivery system 54 features a temporary liquid seal or "viscosity lock" effect inside the microcatheter which allows limited retrieveability (push/pull) of the micrograft during placement. The "pull" of the lock is generated by the tip of the pusher catheter 58, which creates a syringe-like "piston" within the fluid-filled microcatheter 146. Functionality of this lock is dependent on clearances between the microcatheter lumen, proximal micrograft 10 body, adjacent pusher 58 tip, the delivery wire 62, as well as the viscous and cohesive properties of the fluid medium.

Figure 19:
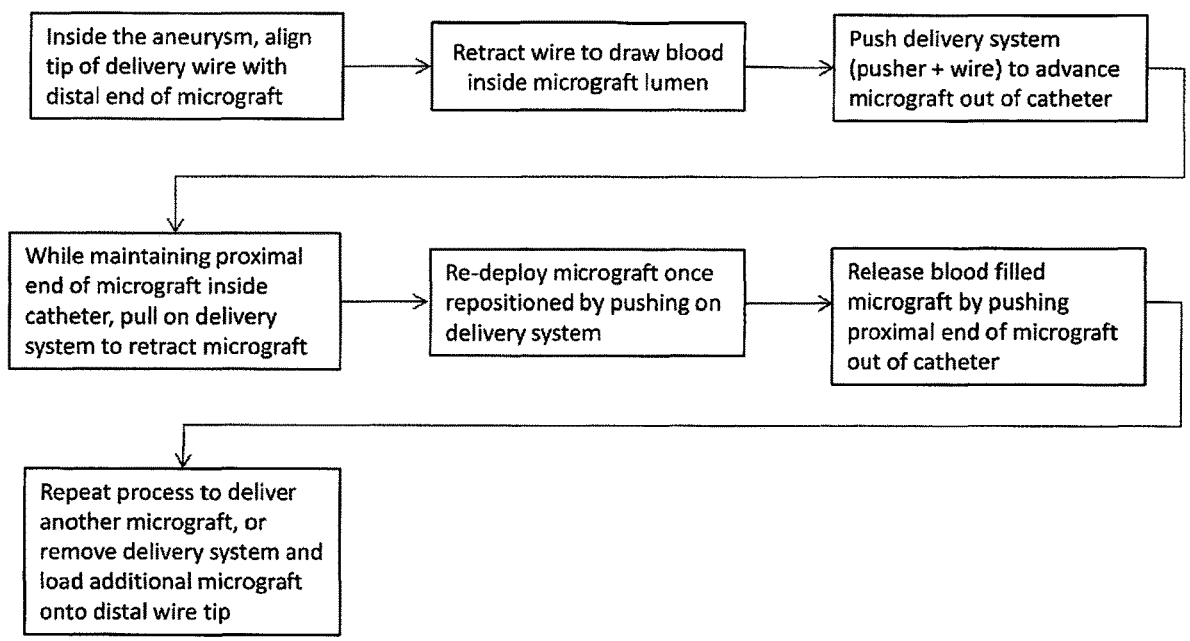
FIG. 19 is a flowchart summarizing viscosity lock function in accordance with an embodiment of the present invention.

The flow chart of FIG. 19 describes the steps of the viscosity lock function which are as follows:
1) Inside the aneurysm, align tip of delivery wire 62 with distal end of micrograft 10.
2) Retract wire 62 to draw blood inside micrograft lumen up to the pusher junction 57.
3) Push delivery system (pusher 58+wire 62) to advance micrograft 10 out of catheter 146.
4) While maintaining proximal end of micrograft 10 inside catheter 146, pull on delivery system to retract micrograft 10.
5) Re-deploy micrograft 10 once re-positioned by pushing on delivery system.
6) Release blood filled micrograft 10 by pushing proximal end of micrograft 10 out of catheter 146.
7) Repeat process to deliver another micrograft 10, or remove delivery system and load additional micrograft 10 onto distal wire tip.

In order for the viscosity lock to work, viscous liquid (i.e., blood) must fill the microcatheter past the micrograft/pusher junction. Once viscous fluid fills the micrograft(s) 10 and gaps around the pusher junction 57, it acts as a "gasket", or a seal, around the pusher/micrograft junction 57 during any displacement (i.e., as the pusher is retracted). The action of pulling the pusher 58 (i.e., the piston) adjacent to the proximal end of the micrograft now creates a low pressure volume. This causes the micrograft(s) 10 suspended in blood to get suctioned and retract within the microcatheter 146.

The micrograft 10 may also be retractable if the delivery wire distal tip 66 is pulled back proximal to the distal tip of pusher 58 or removed completely. High friction or pull resistance is more likely to break the "viscous lock", so the preferred application for this retrieval method is with shorter, lower friction devices or where minimal tortuosity and resistive forces are involved.

In some embodiments of the micrograft delivery system, a pusher wire or delivery wire may not be present inside the micrograft lumen and internal filling of the micrograft with blood will be induced by pressure from the patient's circulatory system or via capillary forces. Capillarity can be achieved by the micrograft having appropriately sized inner diameter or pores, as described earlier. Hence, the absorption of blood into micrograft depicted in FIG. 11C can occur upon contact with blood even if delivery wire or external force is not used to draw blood in.

FIG. 20A-24 illustrate alternate embodiments of the delivery systems of the present invention having alternate locking systems which include a compression coil to apply a distally directed force on the micrograft to facilitate advancement to the target site. The coil is compressed by the micrograft when loaded in the delivery catheter and when the engaging member is released from engagement with the micrograft, the spring returns to its normal state to exert a force on the micrograft. Micrograft 100, identical to micrograft 10' of FIG. 4, except without the deflectable tab 29a, is shown in the delivery systems of FIGS. 21A-22C, 23B, and 24, however, it should be understood, that the delivery systems of FIGS. 20A-24 can be utilized to delivery other micrografts disclosed herein, as well as other micrograft structures or other implantable devices.

Figure 20A:
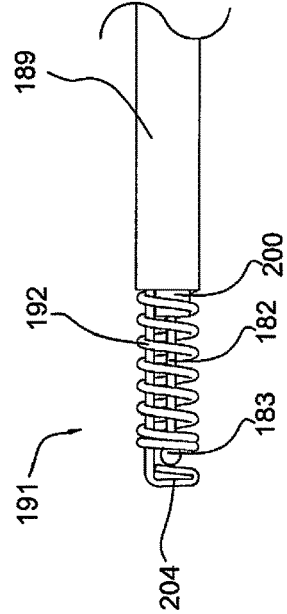
FIG. 20A is a side view of an alternate embodiment of the delivery system of the present invention.

Turning first to the embodiment of FIG. 20A, this version does not include a pusher wire or delivery wire within the micrograft lumen, relying on the micrograft configuration to achieve capillarity as mentioned above. The locking system of FIG. 20A is designated generally by reference numeral 190 and includes a compression coil 192 with a distal end 194, an elongated member in the form of a wire or ribbon 196 with a locking/engaging member in the form of a ball 198 at a distal portion, and a marker band 200. A hood 202 can be provided overlying the locking ball 198 and a portion of the lock wire 196 and coil 192. The locking ball 198 is configured to releasably engage the micrograft as described below.

Compression coil 192 can be made of spring tempered stainless steel, Nitinol, polymers or any other material suitable for manufacturing compression coils, including radiopaque materials such as platinum/iridium. The compression coil in some embodiments has a length between about 2 mm and about 5 cm, more narrowly between about 3 mm and about 2 cm, for example about 5 mm. Suitable diameters for the compression coil 192 in some embodiments can range from about 0.006 inches to about 0.035 inches, more narrowly between about 0.010 inches and about 0.018 inches. Other lengths and diameters are also contemplated. The coil can be open or closed pitch and can have optionally square or ground ends which optionally can be welded, e.g. laser welded.

At the distal end 194 of the coil 192 a hood 202 can be provided which extends over the top of locking ball 198. Hood 202 can be made of plastic or metal, but preferably the hood is made of plastic. It illustratively extends over the first 2 to 3 distal windings of coil 192, but can be made of different lengths to extend over a different number of coils. The hood 202 is secured to coil 192 by various methods such as melting it into the coil windings using a hot air source and removable shrink tube or other methods such as over molding. The hood 202 can extend distally beyond coil 192 and be cut at an angle (as shown), square, or flush with the coil depending on the mating component. The hood 202 limits vertical motion (i.e., transverse movement with respect to a longitudinal axis of the ball lock wire 196) of the locking ball 198 and keeps it from disengaging from the micrograft during tracking of the system through the vasculature to the target site. The hood 202 can have a smooth outer surface to reduce friction inside the catheter. An alternative way to control vertical (transverse) movement of the locking ball 198 is to add material (such as glue or solder) to the top surface of lock wire 196 or locking ball 198.

The ball lock wire 196 with locking ball 198 can be made of material with a flat, round, or varying cross-section with one end of the material melted or formed to create the ball or enlarged feature. The lock wire material can be spring tempered stainless steel, Nitinol, polymer or any other material suitable for manufacturing ball-end wires, including radiopaque materials such as platinum/tungsten. The ball lock wire 196 can in some embodiments have a length equal to or longer than the length of the compression coil 192. The locking ball 198 at the end of the wire can in some embodiments have a diameter in the range of about 0.004 inches to about 0.040 inches, and more narrowly in a range of about 0.006 inches to about 0.012 inches. The locking ball 198 can be centered or offset relative to the longitudinal axis of the wire 196, depending on the structure it is intended to mate with. In the embodiment of FIG. 20A it is shown offset.

The locking system sub-assembly of FIG. 20A can be assembled by inserting the ball lock wire 196 into the compression coil 192 and aligning it so that the locking ball 198 is covered by the hood 202. The locking ball 198 can be positioned inside the compression coil 192 or a distance away from the distal end 194 of coil 192 depending on desired coil compression (release force). The larger portion of the ball 198 (if offset) preferably faces down or away from the hood 202. An optional marker band 200 is partially or completely inserted into the proximal end of coil 192, pinning the wire 196 between the band 200 and the coil 192. The mated components are then soldered or glued to form a joint at the proximal end of compression coil 192 resulting in the locking system sub-assembly 190.

The locking system sub-assembly 190 can be attached to a pusher wire 188 (FIG. 20A) similar to pusher wire 88 described in the embodiment of FIG. 7 above except without the grasper arm. The pusher wire 188 can be solid if desired since a delivery wire need not be utilized. Alternatively, the locking system sub-assembly 190 can be attached to a pusher member or catheter such as pusher 189 of FIG. 20B similar to pusher member 186 described in the embodiment of FIG. 5E above. In this embodiment of FIG. 20B, the pusher member 189 has a lumen extending therethrough for receiving a delivery wire.

In assembly of the delivery system of FIG. 20A the distal end of the pusher wire 188 is slid through the marker band 200, which is positioned inside, and can extend partially outside (proximal) of proximal end of the coil 192, and soldered or glued in place to the marker band 200. Thus, if the marker band 200 is used, the locking wire 196 is directly attached to the marker band 200 (and coil 192). If a marker band is not used, the locking wire 196 can be directly soldered or otherwise attached to the pusher wire 188 (and coil 192). Also, a shrink tube (not shown) can be melted over the proximal end of the joint to smooth out any edges and improve tracking around bends. Alternatively, the push wire 188 can be flattened or round at its distal end and a locking ball such as locking ball 198 can be formed on its tip, which would eliminate the need for ball lock wire 196. The locking system components can also be attached to the pusher wire individually and not as a sub-assembly as described above.

Figure 20B:
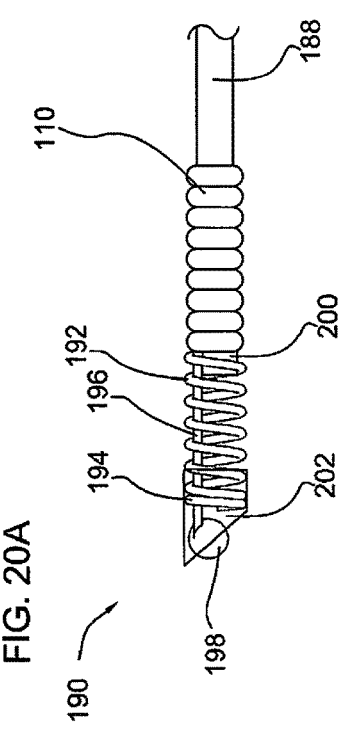
FIG. 20B is a side view of another alternate embodiment of the delivery system of the present invention.

In the embodiment where the locking assembly 190 is attached to a pusher member (pusher tube) such as the pusher member 189 shown in FIG. 20B, the marker band 200 can have an open lumen to accept delivery wire 182 therethrough which also extends through a lumen in the pusher member 189. The band 200 extends slightly proximally from the proximal end of coil 192 so that it can be inserted into pusher member 189 for assembly. Optionally, a shrink tube (not shown) can be melted over the proximal end of the joint to cover any edges and improve tracking around bends. The locking system components can also be attached to the pusher member individually and not as a sub-assembly as described above.

Note FIG. 20B shows an alternate locking mechanism attached to pusher tube 189, but, as noted above, the locking mechanism 190 of FIG. 20A can be used with the pusher tube 189. In the embodiment of FIG. 20B, instead of a locking ball, the locking wire or ribbon (elongated member) of locking mechanism 191 has a flat wire form 204 bent transversely (downwardly as viewed in the orientation of FIG. 20B) with respect to the longitudinal axis. This forms a V-shaped hook like structure to engage the micrograft. Note this embodiment is shown in use with a delivery wire 182 such as the delivery wire 182 of FIGS. 5A-5E, which has an enlarged head 183. Like the embodiment of FIG. 20A, the locking subassembly includes a compression coil 192 positioned over the wire (or ribbon) 204 and marker band 200, with the longitudinally extending portion of wire 204 pinned between the coil 192 and marker band 200.

Figure 22C:
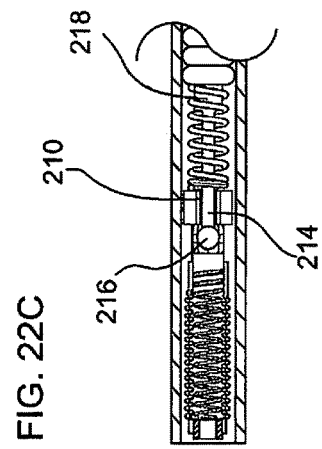
FIG. 22C is a top view of the delivery system and micrograft of FIG. 22A.
Figure 22B:
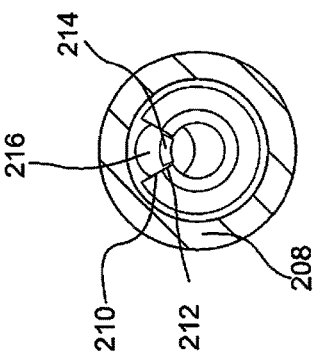
FIG. 22B is a cross-sectional view taken along line A-A of FIG. 22A.
Figure 22A:
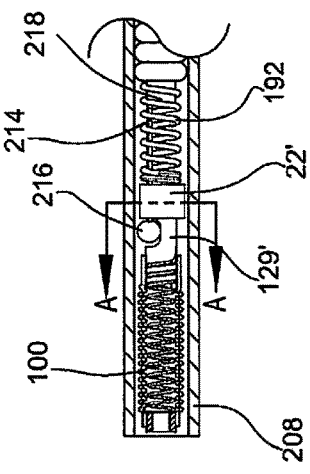
FIG. 22A is a side view of another alternate embodiment of the delivery system of the present invention shown interlocking with a micrograft of the present invention.

The locking wire and locking ball may be formed from a single laser cut tube 218, as shown in the embodiment of FIGS. 22A-22C, which extends within, e.g., is concentric with, compression coil 192, the pusher member (e.g., pusher member 189 (not shown)), and tube 129' of the micrograft 100 to aid in assembly and delivery. This is achieved by laser cutting a long thin section of tubing wall to make a locking wire 214 that transitions on the proximal end from a tube 218, while a distal end of the long thin section is melted into a lock ball 216. Laser cut tube 218 material is Nitinol, but it can be any other shape memory material, metal or polymer, or other materials, with sufficient flexibility and tensile strength. Alternatively, instead of being formed monolithically, the locking ball may be formed by joining or melting a radiopaque material to the end of locking wire, such as soldering a platinum/iridium marker band to the distal tip of locking wire. In the embodiment of FIGS. 22A-22C, the locking ball 216 is shown in engagement with a cutout in the tube 129' of the micrograft. Note as in the embodiment of FIG. 22A, a compression coil 192 is assembled concentric with the wire 214 that is laser cut from tube 218. Note the tube 218 can be radiopaque to also function as a marker.

Figure 21A:
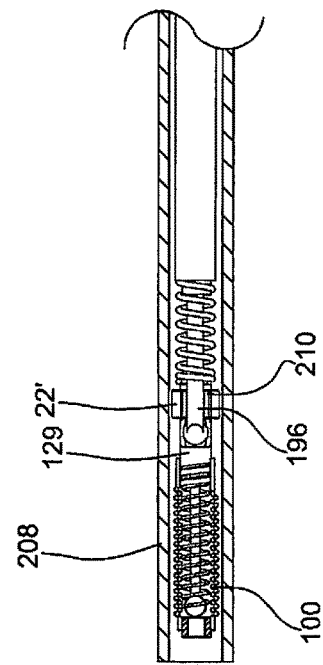
FIG. 21A is a side view of another alternate embodiment of the delivery system of the present invention shown interlocking with a micrograft of the present invention.
Figure 21B:
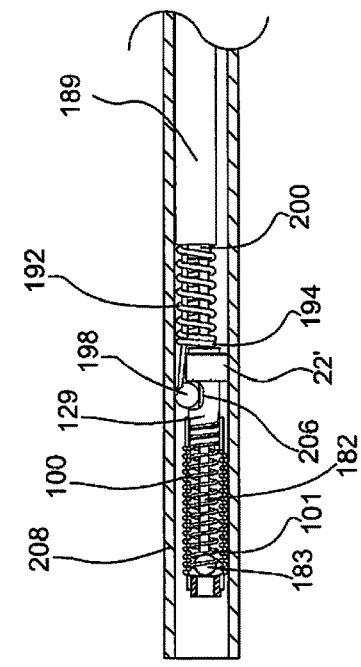
FIG. 21B is a top view of the delivery system and micrograft of FIG. 21A.

FIGS. 21A and 21B show locking sub-assembly 190 of FIG. 20A without the use of the hood 202 and with the use of a delivery wire 182. The locking assembly 190 is fitted to a pusher member 189 and shown locked to the micrograft 100 by way of example. The locking assembly 190 is shown inside introducer sheath 208 (shown in cross section). Core element 101 (identical to core element 27 of FIG. 4A) is positioned inside micrograft 100 (shown in cross section) and is connected to tube 129 (similar to tube 29 of FIG. 4A but without the tab 29a) in a similar manner as core 27 and tube 29. Tube 129 has a window (opening) or cutout (slot) 206 forming a receiving portion therein configured to accommodate insertion (and releasable engagement) of locking ball 198 from the top (as viewed in the orientation of FIG. 21A). Proximal of window 206 on tube 129 is a marker band 22' similar to marker band 22' of the embodiment of FIG. 4C, except having a lengthwise slot 210. The marker band 22' can be attached to tube 129 via welding, soldering, adhesive, or other methods. Marker band slot 210 is sized and positioned such that the wire portion of ball lock wire 196 sits inside slot 210 when lock system is engaged with micrograft 100. Tube 129 may be laser cut from any metal tubing such as stainless steel or other alloys, like platinum/iridium or platinum/tungsten.

To couple the micrograft 100 to the locking system mounted on a push member 189, delivery wire 182 is advanced past the distal end 194 of coil 192 and micrograft 100 is then slid over the delivery wire 182 until tube 129 comes in contact with locking ball 198. Tube 129 is then pushed further proximally (pushing locking ball 198 out of the way), pushing against distal end 194 of coil 192 causing the coil 192 to compress. When coil 192 is sufficiently compressed, lock ball 198 slips into and engages window (opening) 206 of tube 129. While keeping the coil 192 in compression and locking ball 198 seated in window 206, introducer sheath or catheter 208 is advanced over the assembly to prevent locking ball 198 from deflecting out of window 206 and to complete the lock. The lock is engaged as long as tube 129 and lock ball 198 remain inside the sheath 208. Once outside the sheath 208, the compressed coil 192 returns to it normal non-compressed configuration, pushing tube 129 distally with a distally directed force, causing lock ball 198 to slip out and disengage micrograft 100 and pushing the micrograft 100 to the target site. (Note the delivery wire 182 is retracted from the micrograft 100). In the embodiments where the locking system is placed on a push wire assembly such as push wire 188 of FIG. 20A, the coupling steps for locking a micrograft to the lock would be the same with the exception of inserting the delivery wire 182, which is absent in the push wire design. The micrograft would be released in the same fashion as described above as the ball is freed from the confines of the sheath (and hood if provided) to enable it to move laterally to disengage from the tube 129. Also note that the locking hook 204 of the embodiment of FIG. 20B would be assembled/coupled to the micrograft in the same manner as described above (depending if attached to a pusher member 189 as in FIG. 20B or attached to a pusher wire such as pusher wire 188 of FIG. 20A). The micrograft would be released from the hook 204 in the same manner as the locking ball 198 is released from the sheath (and hood if provided) to enable it to disengage from the tube 129.

The embodiment of FIGS. 22A-22C is similar to the embodiment of FIGS. 21A and 21B, however, in addition to the slot 210 of marker band 22', tube 129' has a matching slot 212 as shown in the cross-sectional view of FIG. 22A which runs lengthwise from window (opening) 206 to proximal end of tube 129'. Otherwise, tube 129' is similar to tube 129. Also, FIGS. 22A-22C differ, as noted above, as they depict a version of locking system 190 which has laser cut locking wire 214 and ball 216 formed from a single laser cut tube 218. Inside and outside dimensions of the laser cut tube 218 can overlap with those of tube 129. That is, the dimension of tube 218 at wire region 214 could be greater or less than or equal to the dimension of tube 129'. FIG. 22B provides an example where the dimension of wire portion 214 is less than the dimension of tube 129. Utilizing tubes of the same diameters prevents laser cut lock tube 218 and tube 129' from stacking and achieves minimal radial profile while the lock wire and ball sit inside the slot and window of tube 29. In FIG. 21A, the locking wire 192 extends external of tube 129 within slot 210 of marker band 22', positioned between tube 129 and the inner wall of the sheath 208 while in FIG. 22A, the locking wire 214 is internal of the marking band 22' and extends in slot 212 of tube 129'. When aligned, slot 210 and slot 212 form a V-shaped cross-sectional cut through the walls of marker band 22' and tube 129, which gives the locking ball a tendency to slide radially toward the wider section of the slot while in tension (when the coil is compressed). The lock ball 216 diameter is large enough to prevent the ball from pulling out of the tube/marker band V-slot when the assembly is inside an introducer sheath or delivery catheter. The ball 216 will easily slip out and disengage from tube 129' when the system is advanced out of sheath 208, with the compression coil 192 applying a pushing force on the released micrograft 100. This version of the locking system may be used with or without delivery wire 182. This slotted tube 129' design can be used with any of the previously described locking ball or hook designs.

FIGS. 23A and 23B show an alternative version of the locking system attached to a pusher wire 188. This version of the locking system has a lock wire (elongated member) 219 with a bend or elbow 220, bending at an angle to the longitudinal axis of the lock wire 219. For this lock to engage, ball 221 is inserted into tube 129 of micrograft 100 so that elbow 220 sits partially or completely inside the lumen of tube 129 with ball 221 positioned inside window 206 while coil 192 is compressed by the coupling of the micrograft (coupled in a similar manner as described above). When the introducer sheath 208 is advanced over the engaged locking system, the assembly is constrained so that the curved lock wire 219 is hooked on tube 129 and micrograft 100 is coupled for delivery. Advancing the system out of the sheath 208 causes the compressed coil to push micrograft 100 off the lock wire and detach (release) from the lock wire 219.

Note that although the engaging members are shown in the form of a ball lock or hook in the delivery systems described herein, other engaging structures are also contemplated. It should also be understood that the locking assembly described herein can be utilized with or without a delivery wire, and a hood can be provided in any of the systems.

FIGS. 37A-40 illustrate another alternate embodiment of a locking system of delivery system for the implant. In this embodiment, a delivery member is engageable with the implant, and an elongated internal member, e.g., a wire, maintains the coupling of the implant and delivery member.

More specifically, delivery member 240 is in the form of a pusher tube. The delivery member 240 has a distal extension 242 laser cut to form a cradle at region 244. Region 244 is crescent shaped, forming a U-shaped channel, to receive a band 249. Distal extension 242 is preferably cut at an angle of at least 45 degrees to form a ramp or caroming surface 243. A gap or narrowed section 248 is formed proximal of region 244. The vascular implant 250 has a tube 252 at a proximal end, made of nitinol, stainless steel, or other materials and is similar to tube 29' of FIG. 4F and has a laser cut to form a cradle at region 254. Tube 252 is coupled to coiled inner element of the vascular implant 250. Implant tube 252 and delivery member tube 240 can be cut from the same tube to achieve a low profile when the tubes are nested concentrically, i.e., when coupled or in a locked position. Tubes 240 and 252 can have a different pattern or can have the same or symmetric cut pattern and maintain functionality. Region 254 of tube 252 is crescent shaped, forming a U-shaped channel, to receive a band 259. It is preferably cut at an angle of at least 45 degrees to form a ramp or camming surface 253. Camming surfaces 243, 253 facilitate separation of the implant and delivery member by pushing them apart as one is pulled relative to the other and they slide along these surfaces. That is, when the delivery member (tube) 240 is pulled proximally after retraction of the wire described below, the tubes 240 and 252 are longitudinally displaced and laterally displaced due to the camming surfaces. A gap or narrowed section 257 is formed distal of region 254.

Figure 38:
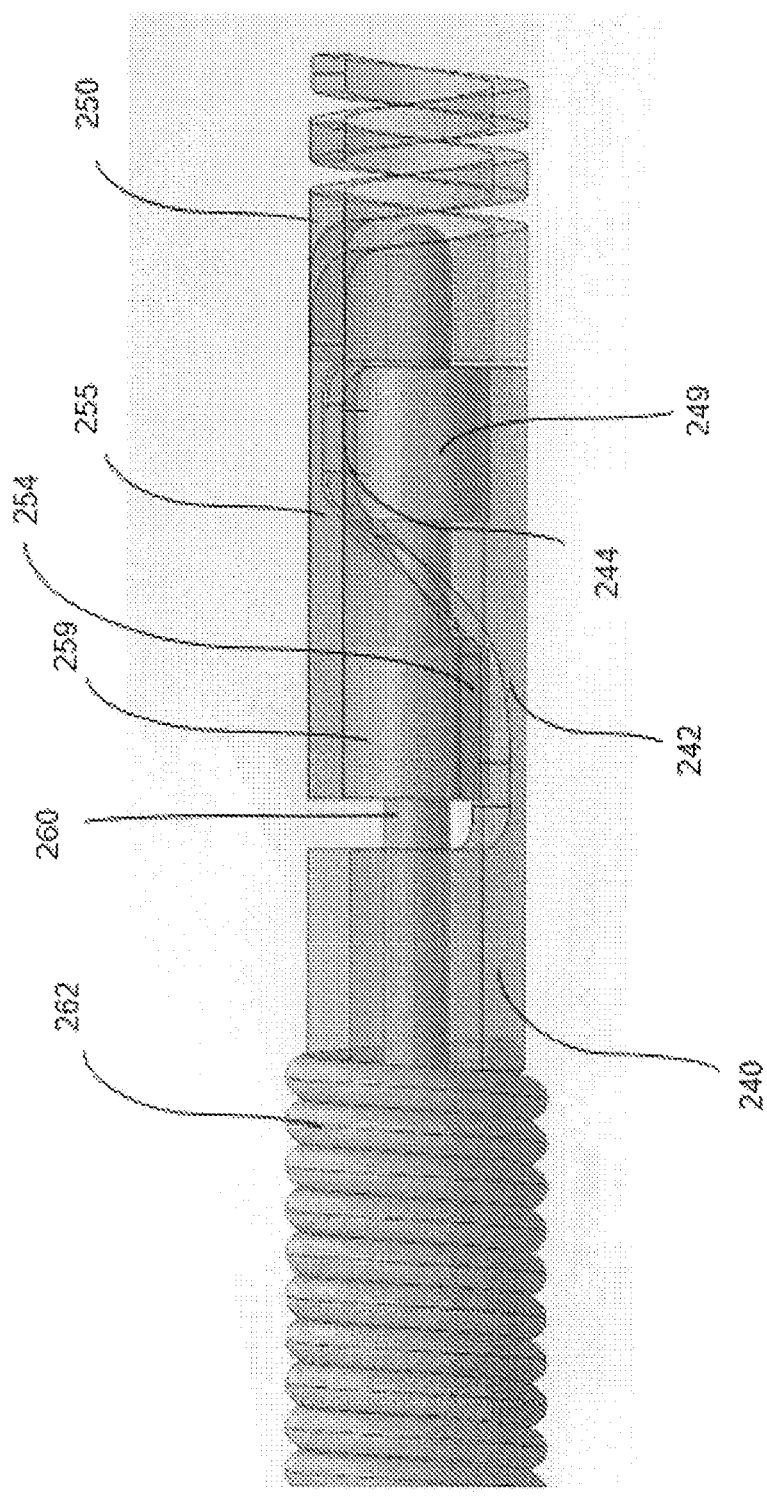
Figure 39:
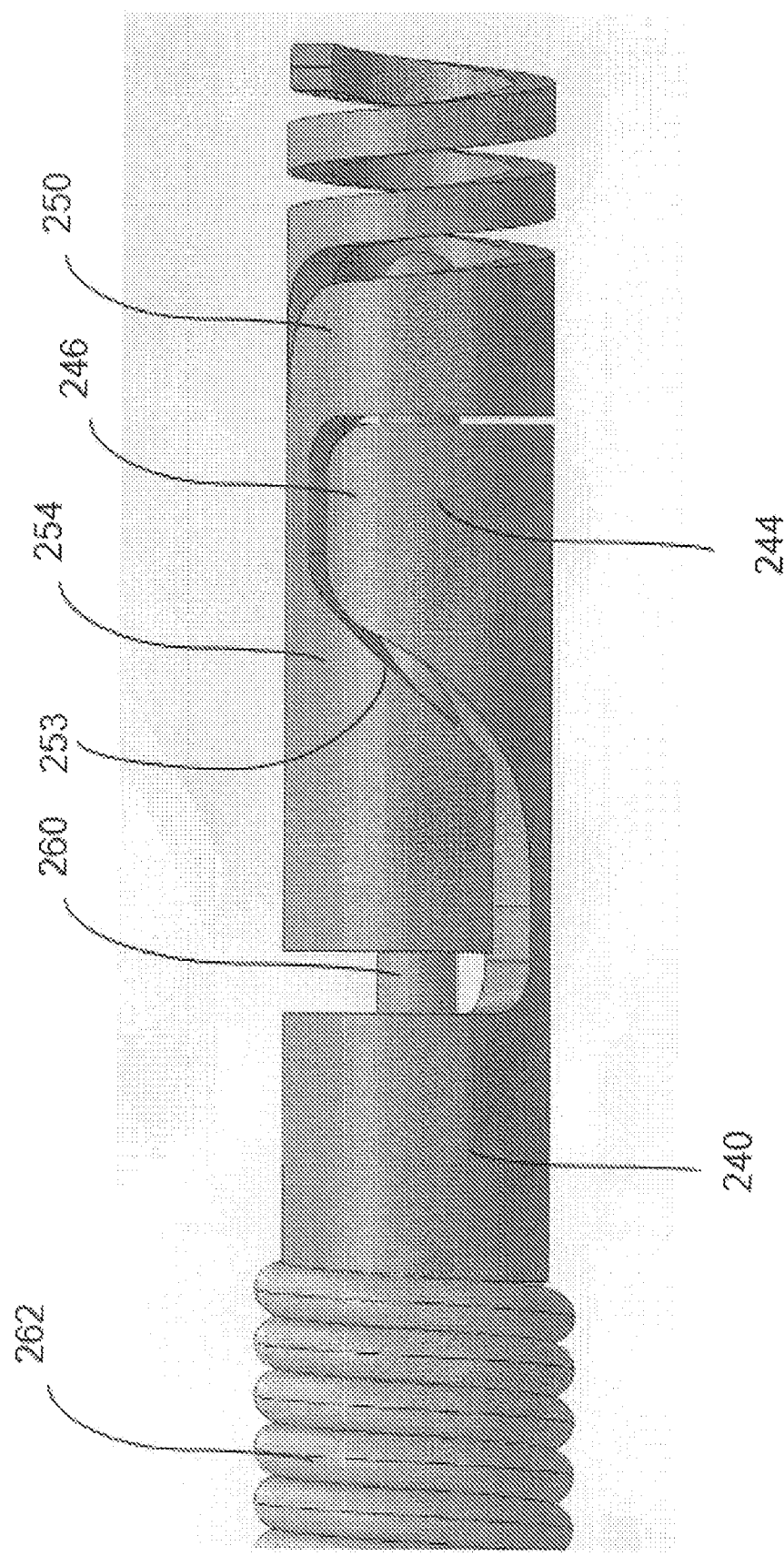
Figure 40:
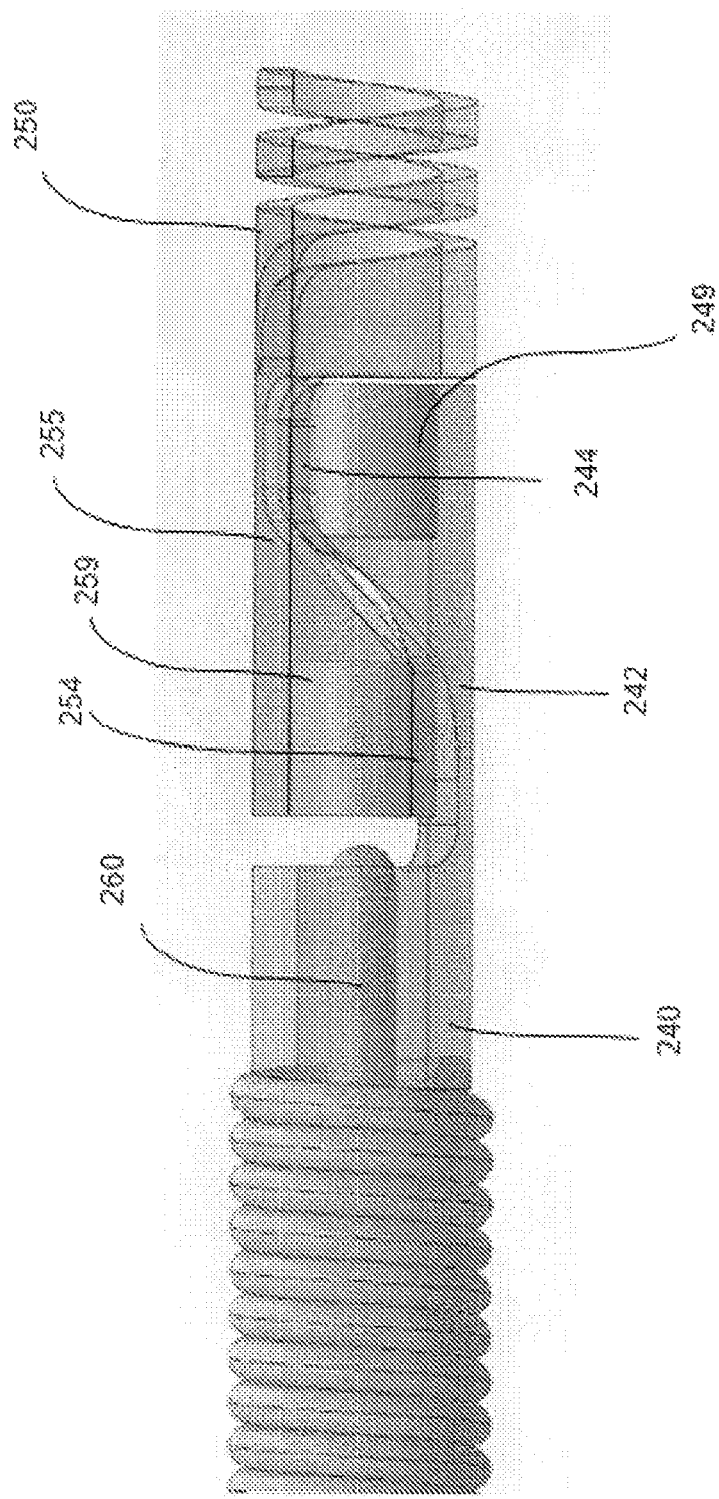

Tube 252 can be attached to the implant 250 in the same manner as tubes 29 and 29', e.g., the distal end of the tube 252 has a helical feature 251 inserted into a proximal end of the coil (inner element) within the tubular braid forming implant 250 and can be attached thereto by rotating or screwing it in between the windings of the coil so the helical feature interlocks with the windings. Other methods of attachment are also contemplated. Region (cradle) 254 is at the proximal end of the proximal extension 255 of tube 252 and is configured to fit within narrowed section 248 of delivery member 240 as shown in FIGS. 38 and 39. Narrowed section 257, formed between wall 258 and cradle 254 receives cradle 244 of delivery member 240. Note FIG. 39 is a side perspective view of the coupled tube 252 and implant 250 and FIG. 38 is a partially transparent view of the coupled tube 252 and implant 250 to show internal features.

The delivery member 240 includes a band 249, e.g., a radiopaque marker band or other radiopaque structure, mounted e.g., welded, within the region 244. Tube 252 of implant 250 includes a band 259, e.g., a radiopaque marker band or the other structure, which is mounted, e.g. welded, in region 254. The bands 249 and 259 each have an eyelet 249a, 259a, respectively, to receive elongated member 260 which maintains the coupling as described below, allowing concentric alignment of the implant with the delivery member. The delivery member can have a coil 262 over the outer region. The delivery member can also have radiopaque marker at its distal end, e.g., about 3 cm from the distalmost edge so it is coupled to the coil of the delivery member, although other distances are also contemplated, to aid in visualization and can have PET or other plastic cover over coil 262. The delivery member 240 and tube 252 can nest together, providing a reduced and smooth profile. They can be made of the same tube and can have different cutout patterns or the same cutout patterns.

In an alternate embodiment, tube 252 has an end that is circular so its continuous in circumference to form the eyelet for the delivery member. In such embodiment, the tube 252 does not have the marker band 259 although in alternate embodiments the marker band could be included. Thus, the configuration is in the form of a loop or ring and not a cradle with separate/spaced ears. Note in this embodiment, when the tube 252 is nested with the delivery member 240 it is not fully concentric as there is a slight gap between the tube 252 and delivery member 240.

An elongated member 260, illustratively in the form of a wire, but alternatively could be in the form of a tube or other elongated device, extends along the distal extension 242 of delivery member 240 and through the eyelet 259a of band 259 of proximal extension 255 of the implant 250, and into the band 249 of delivery member 240, exiting through eyelet 249a. In this position of the wire 260, which can be referred to as the coupling position or the locking position or the extended position (relative to a retracted position), the implant 250 and delivery member 240 remain coupled, i.e., they cannot be decoupled (released) due to wire 260 blocking their separation. When it is desired to decouple (release) the implant 250 from delivery member 240, i.e., after insertion into the body region and ready for placement within the body, the wire 260 is retracted to the position of FIG. 40 where it is moved proximally out of the band 249 (eyelet 249a) of delivery member 240 and out of band 259 (eyelet 259a) of implant 250. In this unlocked position of wire 260 (also referred to as the retracted position or decoupling position), the implant 250 can be decoupled (uncoupled) from the delivery member 240. As noted above, the marker bands 249 and 259 each contain an opening or eyelet, also referred to as a pusher eyelet or an implant lock eyelet, through which the wire 260 passes as shown in FIG. 38. The regions 244, 254 have openings through which the elongated member, e.g., wire, extends by extending through band 249, 259, thereby forming eyelets. Further note that the wire 260 is shown retracted just outside (proximal of) region 254 when retracted, however, it is also contemplated that the wire can be retracted further proximally. Also note that in the extended position, the wire 260 is shown just outside (distal of) region 244, however, it is also contemplated that the wire extends further distal of region 244 than illustrated when the wire is in the extended position. The wire 260 can extend proximally outside the delivery member 240 so it can be grasped at a proximal end by the user and retracted. Alternatively, a mechanism accessible to the user can be operatively coupled to the wire for retracting the wire.

In some embodiments, the elongated member 260 can have a non-linear region, e.g., a wave, bend, coil, etc. at a proximal end to form a contact region within the internal diameter (wall) of the delivery member 240. This provides slight interference (frictional engagement) to limit longitudinal movement and lateral movement of the elongated member 260 during shipment but is minimal enough so that it does not affect the functionality of the delivery member, i.e., does not limit its desired proximal movement during use. In an alternate embodiment, to achieve such interference, a projection such as a bump or ball on a proximal end can extend from the elongated member 260 to engage the internal wall of the delivery member. In another embodiment to achieve a friction point or region, the delivery member can be crimped to reduce its internal dimension for engagement by the elongated member 260.

Figure 41:
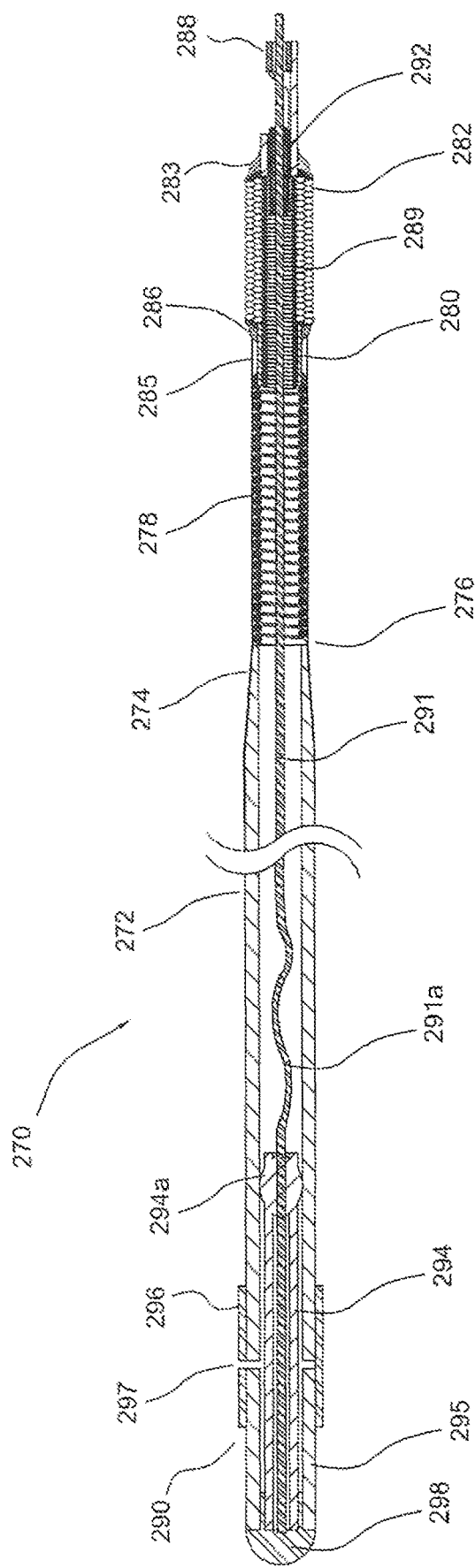
Figure 42:
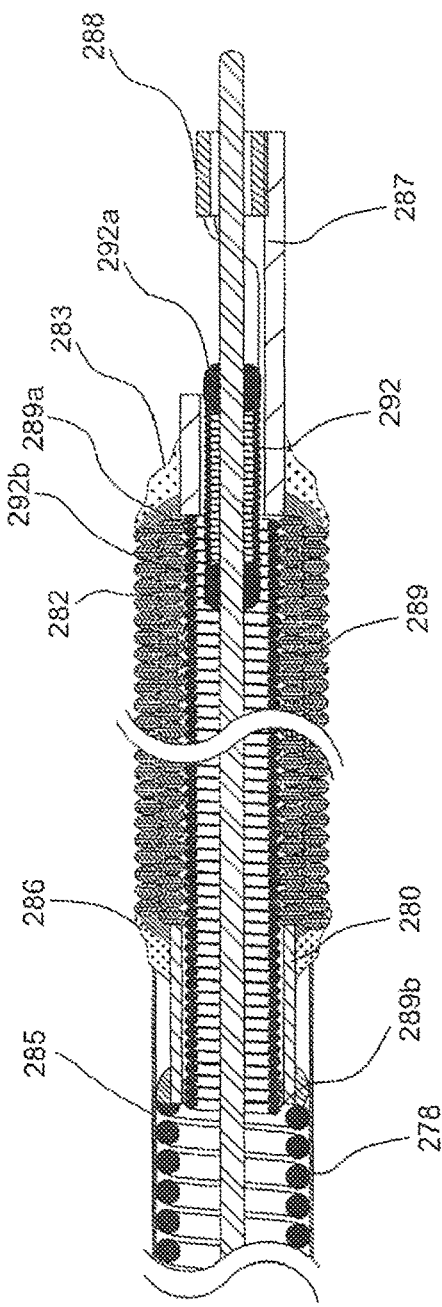
FIG. 42 is a close up view of the distal region of the delivery system of FIG. 41.
Figure 43:
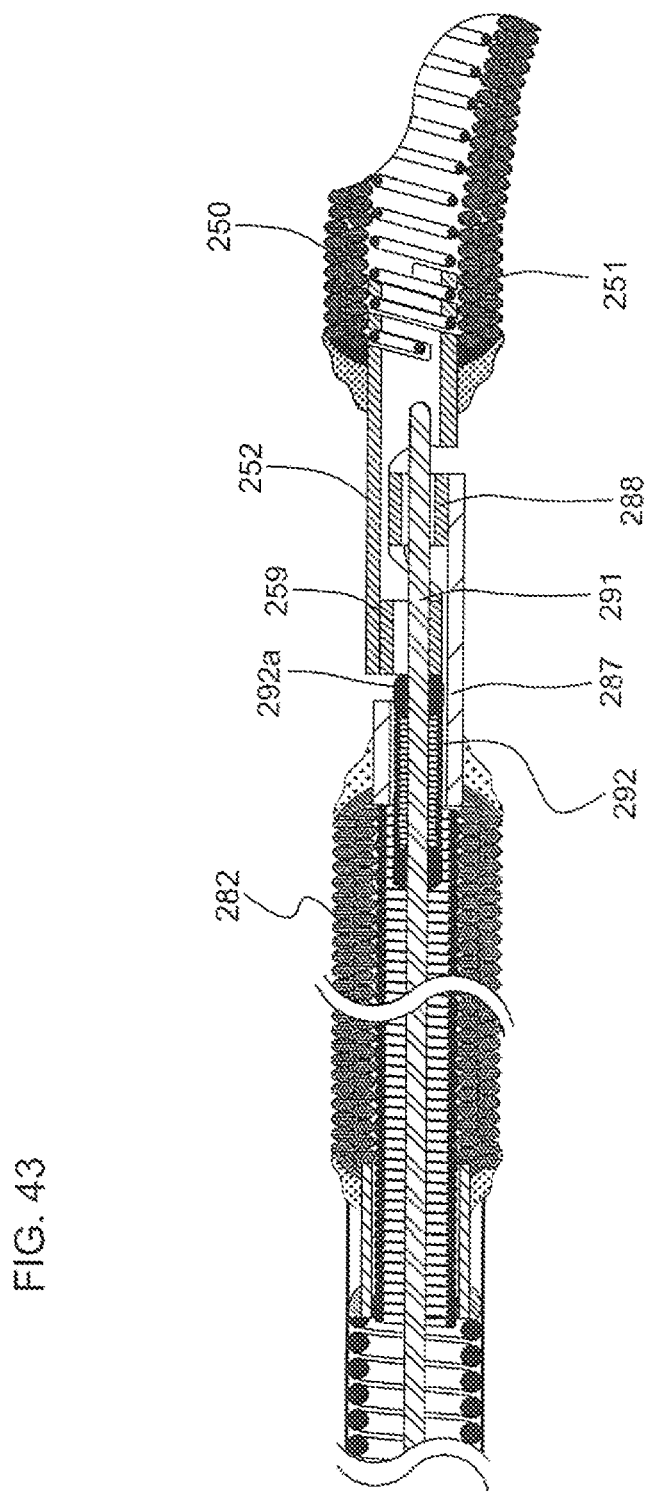
FIG. 43 is a side view showing the surgical implant nested in the delivery member of FIG. 41.

FIGS. 41-43 illustrate an alternate embodiment of the delivery system for delivering an implant in the vasculature. The delivery system 270 includes a hypodermic tube (hypotube) 272 which can be made of stainless steel or other suitable metal or composite tubing having an outer diameter of 0.014" or less and an inner diameter of 0.010" or less.

Other dimensions are also contemplated. The tube can have a taper 274 on the distal end so as to reduce the tubing diameter or it can be a continuous diameter along its length. The reduction in diameter allows for more distal materials to be added over the hypotube without increasing the delivery system diameter, which may increase friction inside the catheter and/or reduce delivery system flexibility.

Welded to the hypotube at joint 276 is stainless steel coil 278. The inner diameter and outer diameter of coil 278 can be sized so as to mate with the hypotube diameters to maintain continuous inner and outer profiles. Attached to the distal end of coil 278 is a radiopaque marker band 280, typically 1 mm to 2 mm in length, although other lengths are contemplated. The band 280 preferably extends from coil 278 to within a proximal end of braid 282. The band 280 has an outer diameter greater than or equal to the inner diameter of the coil 278, although in alternate embodiments it could be less than the inner dimeter of the coil 278. The band 280 can be attached to the coil 278 by welding or other suitable method. Attached to the band 280 is outer braid 282. The braid 282 is bonded at its distal end to tube 287 at distal joint 283 and extends proximally over band 280, where it is bonded at a proximal end to band 280 at proximal joint 286, preferably bonded at the proximal and distal ends through heat but other methods can be used. As shown, the band 280 extends proximally of the braid 282.

The braid 282 provides a softer tip (softer distal end) for the delivery system which aids delivery. That is, typically implants are delivered to the aneurysm through a catheter having a J-shaped tip. This J-tip catheter is straightened by an internal guidewire for delivery through the tortuous vasculature. When the catheter tip reaches the aneurysm, the guidewire is removed and the tip returns to its J-shape. Oftentimes, when implants are inserted through the catheter, the stiffness of the delivery system disadvantageously moves the J-tip from its 90 degree angle to a straighter position, e.g., can move it to 70 degrees or less. This movement away from a 90 degree position to a smaller angle adversely affects placement of the implant in the aneurysm. The braid 282 of the delivery system of FIGS. 41-43 provides a softer tip (of reduced stiffness) so as to minimize deflection, e.g., straightening, of the J-tip.

The braid 282 is made of a series of multifilament PET yarns which may be melted on either end to provide adhesion and a joint. The braid 282 can be crimped to increase its flexibility but it is understood that the braid may also be uncrimped to provide increased stretch resistance and lower outer profile. Note the braid will not compress longitudinally because of the closed pitch inner coil 289. Attached to the distal end of braid 282 is laser cut lock tube 287 with marker band 288, also referred to as an eyelet. This lock tube 287 is similar to the distal lock of FIG. 37A. The narrowed section of the lock tube 287 receives the cradle of the proximal tube 252 of the vascular implant as in FIGS. 37A-40. The proximal end of the laser cut tube 287 is mated end-to-end with a distal end 289a of a smaller metal coil 289 which is attached at a proximal end to the marker band 280. Coil 289 has a proximal end 289b which can extend within distal coils of coil 278. The coil 289 may fit and be attached, via welds or such, to the inside lumen of the marker band 280 or alternatively it can match the inner diameter and outer diameter of the band 280 and mate end-to-end, e.g., the proximal end of coil 289 abutting the distal of marker band 280. Marker band 288 is positioned within tube 287 in a similar manner that marker band 249 is seated within tube 242 of the aforedescribed embodiment and shown in FIG. 37B. Marker band 288 has an opening forming a eyelet for the delivery wire 291. The outer diameter of the coil 289 is sized so that it fits inside the braid 282 and is attached to the braid 282 by a melt joint 283 or it may have a distalmost open pitch winding such that it screws into a mating coil within the braid 282 or mating helical cut threads of tube 287. Thus, it can be the same method of attachment as the implant tube/coil/braid at the proximal end.

Covering the stainless steel coil 278 is PET shrink tubing 285 which extends proximally over the tapered section 274 of hypotube 272 and distally over marker band 280 to the proximal end of braid melt joint 286. The shrink tubing cover 285 can be other polymers or coatings that provide a smooth, low-friction outer surface and stretch resistance or flexibility to the delivery system. Alternatively, a metal wire or ribbon can be added to the system as the stretch-resistant member, whereby the proximal end of such wire is welded to tube 272 and the distal end of the wire is welded to marker band 280. In such embodiments, the tube and/or marker band may be slotted to receive respective ends of the wire and facilitate welding and allow placement of the wire inside coil 278 to minimize outer delivery system profile, or alternatively the wire can be placed outside the coil 278. An additional smaller coil or tubular member may be placed inside coil 278 for passage of pull wire 291 therethrough to prevent entanglement or increased friction due to the stretch-resistant wire (i.e. the smaller coil would serve as sheath for pull-wire adjacent to stretch-resistant wire within the inside lumen of delivery system).

Release tube sub-assembly 290 of delivery system 270 locks the vascular implant as shown in FIG. 43 to delivery system 270 via the mating eyelets, i.e., the eyelet of the lock tube 287 (and marker band 288) of the delivery system 270 and the eyelet in the tube 252 (and band 259) at the proximal end of the vascular implant 250. With the radiopaque marker band 288 in tube 287 and the radiopaque marker band 259 in the cradle of the tube 252 of implant 250, both having openings, as well as the tubes 287 and 252, the eyelet can be considered to also include these marker bands 288 and 259 and/or the openings in the tubes 287 and 252 through which the elongated member, e.g., wire, extends.

The sub-assembly 290 of FIG. 41 is composed of a wire 291, which runs the length of the delivery system into the proximal end of the implant (not shown) to form a lock when both eyelets are mated and aligned (concentric) as in the elongated member 260 of FIG. 38. Thus, the wire 291 threads through mated (aligned) eyelets to lock the delivery member 270 and implant 250. The wire 291 is preferably made of a 0.002" diameter Nitinol wire but may be made of any larger or smaller diameter and made of other flexible material. At the distal end of wire 291, fixedly positioned thereover, is stopper in the form of coil 292 which is made of a radiopaque material. The stopper coil 292 prevents distal movement of wire 291 into the proximal end of the implant as the stopper coil 292 has an outer diameter greater than the inner diameter of the eyelet of band 288. The stopper coil 292 is bonded near distal end of wire 291 at the distal bond 292a. The stopper coil 292 can also be bonded to the wire 291 at the proximal end at proximal bond 292b. The stopper coil 292 can be closed pitch as shown. Alternatively, it can be open pitch to allow compression of the stopper coil 292 over the wire 291 to progressively limit distal movement of the wire 291 into the implant. That is, if open pitched, as the stopper coil 292 is forced against the eyelet of the delivery member, it is compressed. Note that other radial protrusions or features such as wire bends, welds, melted solids, polymers, etc. may be used instead of a stopper coil. These radial protrusions or features can be radiopaque or non-radiopaque.

The wire 291 is shown with buckling 291a along its length due to compression of the wire 291. The purpose of the compressive buckling is to provide extra wire length to prevent premature detachment during tracking in the vasculature, i.e., unwanted proximal movement of the wire 291 which could unlock (decouple) the implant.

Connected to the proximal end of wire 291 is internal pull tube 294 which is attached to wire 291 by using melted PET shrink tubing 298 or other adhesive material. The pull tube 294 can be made of any material but stainless steel is preferred. The tube 294 can also have a bend or bump 294a to provide an additional friction element (frictional engagement member) to engage the internal wall of hypotube 272 to prevent unintended movement of wire 291 and possible premature detachment of the implant due to excessive wire 291 retraction. Attached over the internal pull tube 294 is external pull tube 295. Like the internal tube 294, the external pull tube 295 is preferably made of stainless steel, however other materials may be used. The pull tube 295 is attached to internal tube 294 using a PET shrink tubing, melt joint, weld, adhesive or other mechanical joint. External pull tube 295 is the same outer diameter as shown, or alternatively a smaller diameter, than hypotube 272 and they are joined using PET shrink tube 296 which has cut 297. The shrink tube 296 can be dark or a bright color (highly visible) to indicagte to the user where to grab the tube. The cut 297 forms a weakened section to allow a break-away joint to allow easy retraction of the external pull tube 295 for implant detachment. Separation of shrink tubing 296 at cut 297 also indicates to the clinician that the pull tube 295 has been retracted and the implant detached.

To detach the implant 250 from the delivery system 270, the operator pulls proximally on pull tube 295 with enough force to break shrink tube 296 at cut 297, allowing proximal movement of release tube assembly 290 and wire 291. As wire 291 retracts, it pulls out of the delivery system eyelet and the implant eyelet (which is proximal of the delivery system eyelet when nested as in the FIG. 39 embodiment), thereby no longer constraining them concentrically, and allows them to disengage. This disengagement is in the same manner as the disengagement of FIGS. 37A-40, with the camming surfaces facilitating detachment as described above.

FIG. 24 illustrates another embodiment of an intra-aneurysmal micrograft delivery system generally referred to by reference number 222. Delivery system 222 is designed to deliver a flow diverter 224 in combination with a micrograft 100 on a single delivery wire 226 using locking system 190 by way of example for micrograft attachment. One or more micrografts may be loaded on the delivery wire (using previously described methods) in tandem with a stent or flow diverter for more efficient delivery. Also, instead of a flow diverter a stent can be loaded within sheath 208. Note the flow diverter (or stent) is positioned proximal of the micrograft for delivery after delivery of the micrograft. Although lock ball arrangement of FIG. 24 is shown, other locking systems described herein can also be utilized.

In use, the system 222 is introduced and tracked through a microcatheter which has been positioned with its distal tip in an aneurysm. The micrograft 100 would be deployed into the aneurysm first, then the microcatheter tip would be pulled back into the parent vessel and positioned for delivery of the flow diverter (or stent). The flow diverter would then be delivered. Once flow diverter 224 is delivered, the microcatheter would be removed. For this design, locking system 190 and the delivery wire 226, can have coils distal of the flow diverter, and the coils and/or the flow diverter may be radiopaque to help identify wire position during interventional procedures.

Figure 12A:
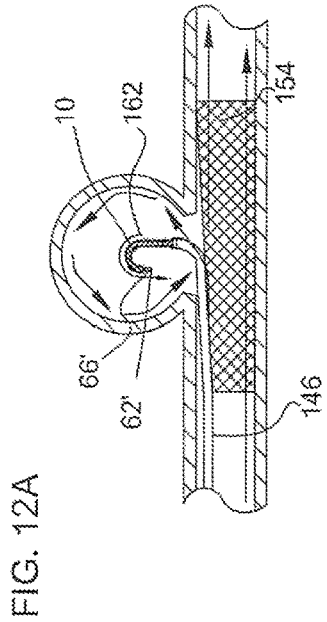
FIGS. 12A-12C illustrates directed delivery by the delivery wire of an intra-aneurysmal micrograft into an aneurysm in accordance with an embodiment of the present invention.
Figure 12C:
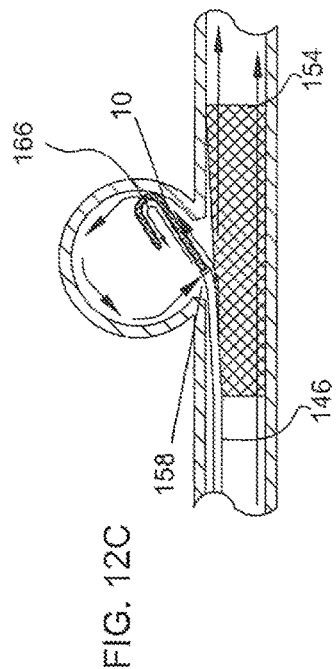
Figure 12B:
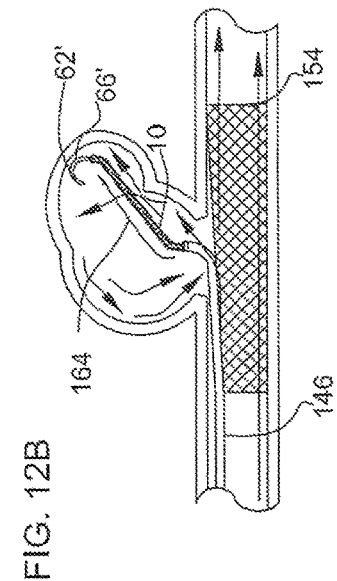

FIGS. 12A through 12C show directed delivery of micrograft 10 of FIG. 1 inside an intracranial aneurysm. Other micrografts described herein can be delivered in a similar manner. Unlike micrograft delivery described in FIGS. 10 and 11A-11F above, in the embodiment of FIGS. 12A and 12B, the shaped delivery wire 62' remains in the aneurysm so that the micrograft deployment can be directed to a targeted location (neck) within the aneurysm sac. FIG. 12A illustrates a distal tip 66' of delivery wire 62' that has been shape set in a "J" and deployed so that the "J" points at the stent or flow diverter 154 covering the neck of the aneurysm. As the pusher catheter 58 is advanced distally, the micrograft 10 will deploy and follow along the delivery wire 62' in a direction denoted by arrow 162 towards the stent or flow diverter 154.

FIG. 12B illustrates a delivery wire 62' that has been shape set with a "J" and advanced into the dome of the aneurysm. As the micrograft 10 is advanced it will follow the curvature of the wire 62' in a direction denoted by arrow 164.

FIG. 12C illustrates that the microcatheter 146 can be used to direct micrograft deployment within the aneurysm. The delivery wire has been pulled back into microcatheter 146 which is seated in the neck of the aneurysm 158. As the micrograft 10 is advanced it will follow the direction denoted by arrow 166. The tip of the microcatheter 146 can be curved to direct the micrograft 10. When the micrograft 10 encounters barriers, such as the aneurysm wall, it will easily change direction as depicted.

FIG. 13 illustrates the deployment of flow directed micrografts 168 using intra-aneurysmal micrograft delivery system 54 with delivery wire 62' having a "J" form at its tip and extending from microcatheter 146. Micrografts 168 can have the same structure as other micrografts described herein. Flow directed micrograft 168 can be any length, but shorter lengths such as about 2 mm to about 5 mm are utilized in this embodiment so as to move with blood flow. Since the flow directed micrografts 168 tend to be shorter than micrografts configured to fill the aneurysm, many more flow directed micrografts can be loaded onto the delivery wire and consecutively deployed, as illustrated in FIG. 13. Micrograft 168 has been shape set into a "C" shape, however, other shapes are also contemplated as discussed above.

As each micrograft 168 is advanced distally off the delivery wire 62', it will be caught up in blood flow exiting the neck of the aneurysm. Due to the stent or flow diverter 154 blocking the neck 158, micrograft 168 will be restricted from exiting into parent vessel 170. When a sufficient amount of micrografts 168 are introduced into the aneurysm, the micrografts will pile up and clog or create a localized graft at the stent/flow diverter and neck interface. Over time, thrombus will form above the clog to aid in closing off the aneurysm. The smaller, shorter micrografts are intended to provide a more complete obstruction or fill voids at the aneurysm neck.

FIG. 14 illustrates microcatheter 146 positioned inside the parent vessel 170. This embodiment differs from the previous embodiments in that instead of extending in the space between the stent 154 and parent vessel 170, the microcatheter 146 extends through the struts or pores of stent or flow diverter 154. In all other respects, the system is the same as that of the aforedescribed systems. Note micrograft 10 is shown exiting the microcatheter 146 into the aneurysm. Longer length or shorter length micrografts can be delivered.

As discussed earlier, the delivery wire 62 can be a guidewire. Therefore, if desired, the micrograft delivery system with guidewire can be loaded into the microcatheter prior to catheter placement. The entire assembly, microcatheter and micrograft delivery system, can then be tracked to the aneurysm site using the delivery system's guidewire as the primary tracking wire. Alternately, the guidewire and microcatheter can be tracked to the aneurysm site and rapid exchange catheter, e.g., pusher catheter 80 of FIG. 6, can be advanced subsequently.

FIG. 15 illustrates the distal end of intra-aneurysmal micrograft delivery system 86 of FIG. 7 deploying micrograft 90. Micrograft 90 has been released from arms 94, 98 and has assumed a pre-biased (pre-set) shape. As noted above, the micrografts can be pre-set to a variety of configurations and the shapes illustrated in the drawings are provided by way of example. If desired, the micrograft 90 can be retrieved by capturing a portion of the structure between arms 94, 98, and advancing the microcatheter 146 over the arms to compress the arms. Alternately, the delivery arms 94, 98 can be used to compress or move the micrograft around the aneurysm to aid in packing.

Figure 18A:
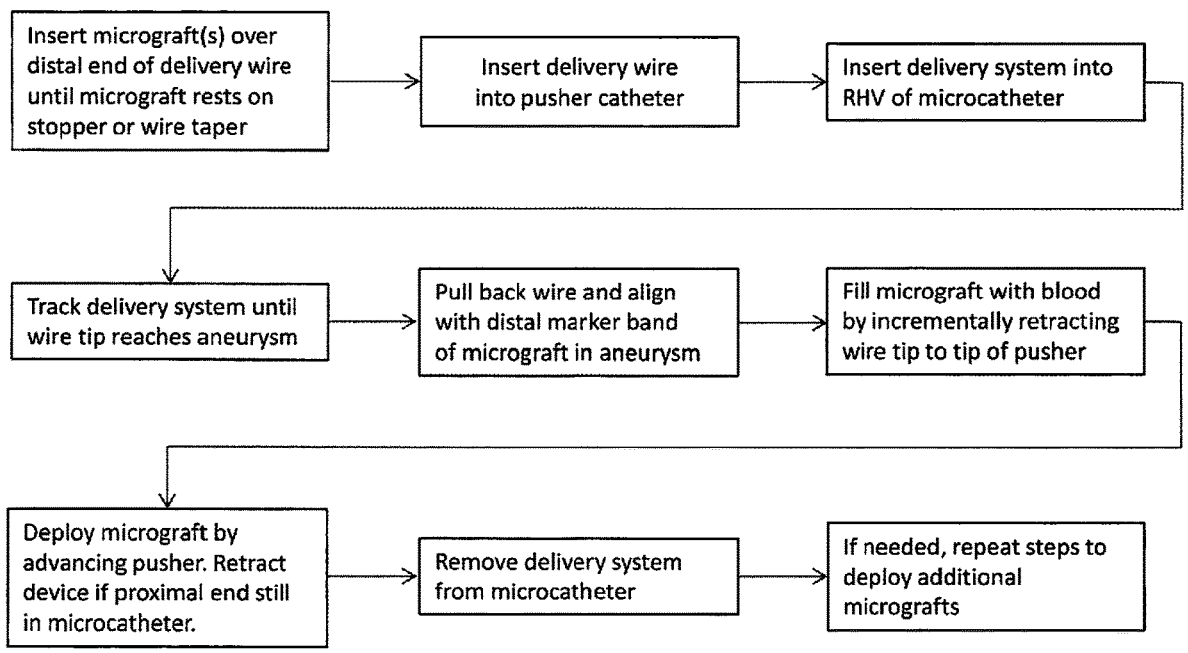
FIGS. 18A and 18B are flowcharts summarizing alternate methods of placing and deploying a micrograft of the present invention.

FIG. 18A provides a flow chart for one method of placing a micrograft of the present invention. This method utilizes the delivery system of FIGS. 5A and 5C. The steps include:
1) Insert micrograft(s) over distal end of delivery wire 62 until micrograft rests on stopper or wire taper 70.
2) Insert delivery wire 62 into pusher catheter 58.
3) Insert delivery system into RHV 78 of microcatheter.
4) Track delivery system until wire tip 66 reaches aneurysm.
5) Pull back wire 66 and align with distal marker band of micrograft in aneurysm.
6) Fill micrograft with blood by retracting wire tip 66 into the micrograft.
7) Deploy micrograft by advancing pusher 58. Retract device if proximal end still in microcatheter.
8) Remove delivery system from microcatheter.
9) If needed, repeat steps to deploy additional micrografts.

Figure 18B:
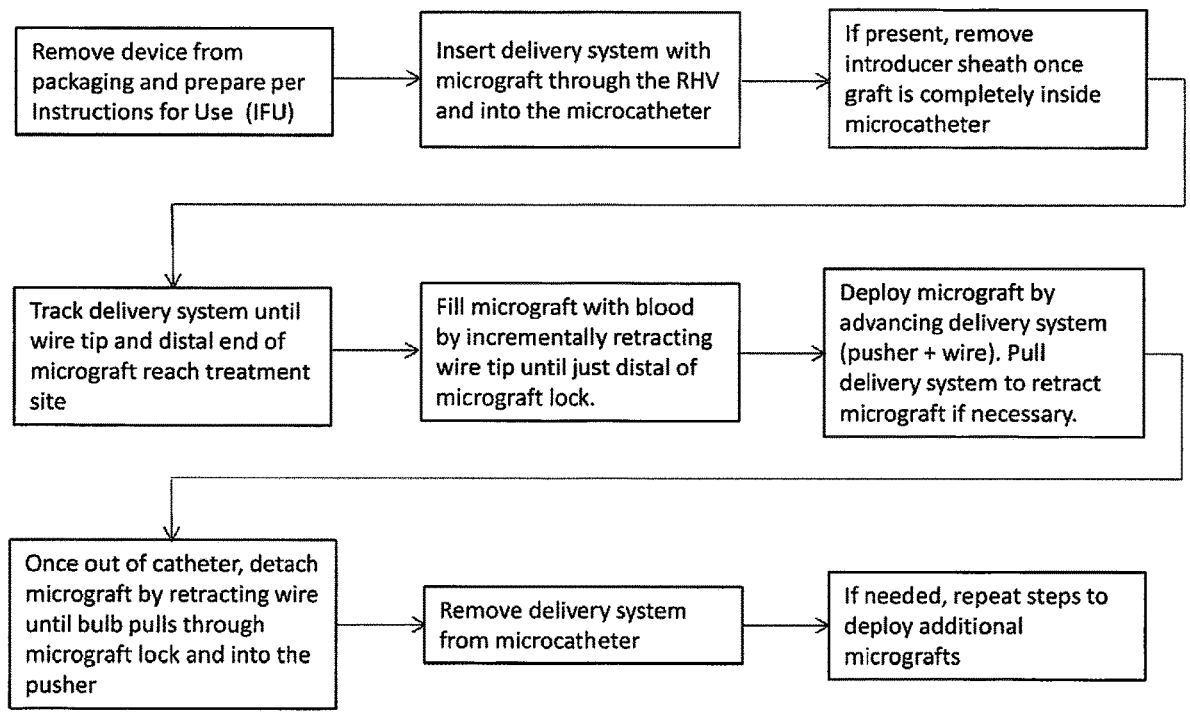

FIG. 18B provides a flow chart for another method of placing a micrograft of the present invention. This method utilizes the same delivery system of FIGS. 5E-5H. The steps include:
1) Remove device from packaging and prepare per Instructions for Use (IFU).
2) Insert delivery system with micrograft into microcatheter RHV.
3) If present, remove introducer sheath once micrograft is inside microcatheter.
4) Track delivery system until wire tip 184 and distal end of micrograft reach the treatment site.
5) Fill micrograft with blood by incrementally retracting wire tip 184 just distal of the micrograft lock (tab 29a).
6) Deploy micrograft by advancing delivery system (pusher 186 and wire 182). Pull delivery system to retract micrograft if necessary.
7) Once out of microcatheter, detach micrograft by retracting wire 182 (or advancing pusher) until wire bulb 184 pulls through micrograft lock (tab 29a) and into the pusher 186.
8) Remove delivery system from microcatheter.
9) If needed, repeat steps to deploy additional micrografts.

Note the delivery systems and occluding devices (micrografts) disclosed herein have been described for use for treating intracranial aneurysms. It should be appreciated that the delivery systems and occluding devices (micrografts) can also be utilized for treating aneurysms in other regions of the body or for treating other vasculature or for treating non-vascular diseases.

Note the delivery systems disclosed herein can be utilized to deliver the various micrografts disclosed herein and specific micrografts discussed in conjunction with specific delivery systems are provided by way of example.

The above delivery systems and concepts are preferred ways to deliver the intra-aneurysmal micrograft. The micrograft however may alternatively be constructed to mate with other microcoil delivery systems that provide a timed and controlled release, e.g., electrolytic detachment as described in U.S. Pat. No. 5,354,295 and its parent, U.S. Pat. No. 5,122,136, both to Guglielmi et al., interlocking ball and key way as described in U.S. Pat. No. 5,261,916 to Engelson, and pusher with mating ball configuration as described in U.S. Pat. No. 5,304,195 to Twyford et al.

In some applications, other vaso-occlusive devices such as platinum microcoils may be used in combination with the micrografts of the present invention to occlude the aneurysm.

The delivery systems disclosed herein are for uses for delivering devices for treating intracranial aneurysms, however it is also contemplated that the delivery systems can be used to deliver devices through and in other body lumens in a patient.

FIGS. 29-36 illustrate one embodiment of packaging for the vascular implants disclosed herein. The packaging can be used for any of the vascular implants disclosed herein, and is shown for illustrative purposes in FIGS. 29-36 with the vascular implant 250 of FIG. 37 having a secondary helical shape like the vascular implant of FIG. 4K. The packaging can also be used for implants other than those disclosed herein, e.g., shape memory implants.

The packaging is designated generally by reference numeral 300 and is contained in a shipping pouch or package (not shown). The packaging 300 includes a long packaging hoop 302 and a short packaging hoop 304. The hoops 302, 304 are in the form of tubes composed of a material such as HDPE or polypropylene that can be wrapped as shown without significant kinking that could inhibit movement of the components within the tubes 302, 304. The short packaging tube 304 is shown in FIGS. 29 and 30 as darkened for ease of illustration but the short tube 304 can be of the same color as the long tube 302. A series of clips 306 spaced apart along the tubes retains the tubes (hoops) 302, 304 in the coiled (spiraled) configuration as shown, preferably evenly spaced. Each of the tubes 302, 304 has a lumen extending therethrough. By way of example, the short tube 304 can have a length ranging from about 10 cm to about 100 cm, and more specifically about 70 cm; the long tube 302 can have a length ranging from about 100 cm to about 280 cm, and more specifically about 240 cm. Other lengths are also contemplated. The long tube 302 is preferably longer than the short tube 304, however, in some embodiments they can have equal lengths or tube 302 can be shorter than tube 304. The ends of the tubes 302, 304 are spaced apart as shown to provide a gap 308. More specifically, short tube 302 has a first distal end 303 adjacent the implant 250 and a second opposite proximal end 307. Long tube 302 has a proximal end 305 and an opposite distal end 309. The distal end 309 of the long tube 302 is spaced from the proximal end 307 of the short tube 304 to form the gap 308. This exposes the delivery member and delivery sheath (together referred to as the delivery system) as described below. The gap can be between about 2 cm and about 40 cm, and more specifically about 15 cm, although other dimensions are contemplated. The gap 308 can be considered/measured as the length of an arc extending between the proximal end 307 of short tube 304 and the distal end 309 of the long tube 302, equated with the length of the delivery system that is exposed between the tubes 302, 304. Note the term distal and proximal in reference to the tubes 302 and 304 as used herein is used to identify the portion/ends in relation to the path of the implant from the container through the tubes 302, 304—the distal end/portion is adjacent where the path for the implant begins (closer to the initial position of the implant in the container) and the proximal end/portion is further from the start of the path of the implant. Stated another away, the distal end is at the location of insertion of the implant from the container into the tube 304.

The packaging 300 further includes a container 320 having an elongated finger or support 322 over which the implant is mounted, e.g., seated or wrapped around in a secondary, (e.g., helical) shape. The support or post 322 extends within the internal receiving space 323 of the container 320. A cap 324 can be provided which can be removably attached to the container 320 and can be attached by a snap fit, a screw thread or other methods. The cap 324 can be removed for mounting the implant 250 on the support prior to shipping. The container 320 can be positioned substantially perpendicular to the end 303 of short tube 304 such that the finger 322 is substantially perpendicular to the end 303 and opening 311 in the distal end of the short tube 304, i.e., substantially transverse, to a longitudinal axis passing through the opening 311. As shown in FIG. 30 the implant 250 is of a three dimensional helical configuration (e.g., its secondary shape) and is seated on the finger 322 such that a longitudinal axis of the implant is along an axis of the finger support 322. The implant 250 can be slid over the free end 327 or the opposing end (with the cap removed) of the finger 322 prior to shipping. A recess or receiving space in the packaging or tray (not shown) can also be provided in some embodiments to help maintain the implant in position on the finger 322.

In the embodiment of FIGS. 29-36, the finger 322 is substantially perpendicular to the sheath opening such that the implant is held in the substantially perpendicular position with respect to the opening 311. ("Substantially" encompassing for example an angle between 80° and 100°). It should be understood that the implant can alternatively be held in a parallel position, or at other angles, with the support, e.g., finger, positioned in a parallel or other angled position.

The container 320 is shown with an internal space 323 larger than the transverse dimension D of the implant 250. It can be appreciated, that other dimensions for the internal space 323 are also contemplated as long as they accommodate the implant for the delivery method as disclosed herein and limit movement, e.g., bouncing, of the implant 250 within the container 320. It is also contemplated that the packaging container 320 in some embodiments can be sized to contain the implant in its secondary shape, i.e., relaxed or unconstrained condition/configuration and may not need a supporting member 322. In some embodiments, the container can be perforated or non-airtight to allow gas permeation and flow through the container during product sterilization, e.g., during ethylene oxide gas sterilization.

The short tube 304 as shown forms a wrap of a little more than 360 degrees. The longer tube 302 wraps around multiple times to form a series of circular wraps either adjacent or partially overlapping, thereby arranged in a coil or spiral. The short tube 304 can be adjacent or overlapping the long tube 302. Note the lengths/wraps of the hoops 302, 304 illustrated are one example that can be utilized, it being understood that tubes 302 and 304 of lengths (and wraps) different than that illustrated and described are also contemplated. The short and long tubes could also be modified so that tube 304 is longer than tube 302.

Contained within the tubes 302, 304 are a delivery member 330 and a sheath 332 which are part of the delivery system of the implant. More specifically, the delivery member 330 is coupled to the implant and extends through the sheath 332. The delivery sheath 332 and delivery member 330 with attached (coupled) implant are removed from the tubes 302, 304 for insertion of the implant into a patient's body. Various embodiments of the delivery member 330 can be utilized and it can be indirectly coupled or directly coupled to the implant. In the embodiment of FIGS. 29-30, the delivery member 330 is in the form of a tube which is disclosed in FIGS. 37-40 discussed above. Alternatively, the delivery member can be in any of the configurations described above, including in the form of a delivery wire. Moreover, other types of delivery members could be provided to pull the implant from the packaging container 320 and to advance the implant into the body structure, e.g. the intracranial aneurysm.

The sheath 332 extends within the short tube 304 from a region adjacent the container 320, i.e., a region adjacent opening 311 at distal end 303 of short tube 304 and exits at the opposite (proximal) end 307 of tube 304 through proximal opening 313. A portion 333 of the sheath is exposed in the gap 308 between the short and long tubes 304, 302, i.e., between proximal end 307 of short tube 304 and distal end 309 of long tube 302. The exposed portion 333 can be between about 1 cm and about 39 cm, although other dimensions are contemplated. The delivery member 330 extends through the lumen of the delivery sheath 332 and thus through the short tube 304 along with the sheath 332, thereby exiting proximal opening 313 of tube 304 along with the sheath 332. The delivery member 330 extends out of proximal opening 335 at the proximal end 334 of sheath 332 such that portion 338 is exposed between the end 334 of sheath 332 and the distal end 309 of long tube 302. The exposed portion 338 can be between about 1 cm and about 39 cm, although other dimensions are contemplated. The delivery member 330 extends through distal opening 312 at end 309 and through the lumen of the long tube 302. The delivery member 330 can terminate within the long tube 302 or alternatively can be of sufficient length to extend out of opening 314 at proximal end 305 of long tube 302.

As can be appreciated, the vascular implant 250 is stored within the container 320 in its placement state (condition). That is, it is maintained in an unconstrained position (condition), corresponding to its secondary helical shape, during packaging and shipping. This advantageously reduces the chances of mechanical creep (loss of shape recovery) of the implant 250, e.g., to take a set in a reduced diameter position or non-secondary shape which might occur if it were packaged within the delivery sheath itself since the delivery sheath has an internal diameter less than the internal diameter (dimension) of the container 310 and less than an outer diameter or transverse dimension D of the unconstrained implant 250. In other words, the implant is maintained in the container 320, e.g., on the finger 322, in the same state, i.e., its secondary shape, that it is designed to be placed in the body, e.g. aneurysm, or at least at a shape closer to its placement shape than if it were in the smaller diameter delivery sheath, thus better ensuring it will return to this state after passage though the delivery sheath 332 and through the microcatheter into the body. If the implant 250 was shipped within the delivery sheath 332, it would be held in a constrained position with a reduced transverse dimension (reduced profile) in order to fit within the sheath since the sheath has a small diameter. Instead, the implant is retained outside the delivery sheath in a non-constrained or less constrained condition having a transverse cross-section greater than the transverse cross section or diameter of the sheath, until the point in time the implant is ready for insertion from the sheath into the catheter for insertion into the body. Packaging the implant in the 3D secondary configuration also allows the clinician to visually confirm the implant size and shape prior to insertion into the body. If it is packaged in a constrained condition within the sheath or packaging, the clinician would first need to remove the implant from the packaging to view its secondary shape, and then reload in into the packaging or sheath.

In other words, in the first condition within the container 320, the implant has a first transverse dimension. In the second condition when pulled within the delivery sheath, the implant has a second transverse dimension less than the first transverse dimension. The first transverse dimension of the implant (when unconstrained) is greater than the transverse dimension, e.g., the diameter, of the delivery sheath. Note the transverse dimension can be considered as an overall height, perpendicular to a longitudinal axis of the implant, and represented by reference letter D in FIG. 30. Thus, if a first imaginary line is drawn on a first side of the longitudinal axis tangent to the largest peak on the first side of the longitudinal axis of the implant and a second imaginary line is drawn tangent to the largest peak on the second opposite side of the longitudinal axis, a straight line distance connecting the two imaginary lines and drawn perpendicular to the longitudinal axis of the implant represents the transverse dimension. Note the transverse dimension is different than the primary diameter dimension of the implant. That is, it is the size of the overall shape of the implant that changes, i.e., it is moved from an unconstrained (or less constrained) condition in a non-linear shape (closer to or in its secondary shape) within the container to a constrained linear or more linear shape within the sheath (closer to or at its primary shape).

It should be understood that when released from the delivery sheath 332 the implant will move to fill the body space—if the body space is smaller than the transverse dimension of the implant in its secondary shape then the implant will move to the dimension of the body space which is still larger than the transverse dimension of the delivery sheath.

The method of loading the implant 250 from the container 320 into the sheath 332 for insertion into the microcatheter for delivery into the body lumen, e.g., vessel or aneurysm, of the patient will now be described. The method can be understood with reference to FIGS. 31-36.

In the first step (FIG. 31), the delivery member 330 is grasped at the exposed region (portion) 338 and at the sheath 332 by the clinician. As noted above, the exposed portion is between distal end 309 of long tube 302 and proximal end 334 of sheath 332 which extends beyond proximal end 307 of short tube 304. The clinician pulls the delivery member 330 relative to the sheath in a direction (see arrow) away from the short tube 304 (FIG. 32) e.g., in a proximal direction relative to the delivery sheath 332. The delivery member 330 is attached to the implant in the illustrated embodiment by engagement of the cutout portions as explained above in connection with FIGS. 37-40 and 41. By pulling the delivery member 330, the implant 250 is unwound from the finger 322 and pulled into the sheath 332 through its distal opening and into the lumen into a more elongated, e.g., more linear, position of reduced transverse dimension (constrained position). After the implant 250 is pulled from the container 320 and pulled fully inside the lumen of the sheath 332, the clinician next (preferably with a single hand) grasps the exposed portion 333 of sheath 332 (FIG. 33) preferably at its end 334, and pulls it along with grasped delivery member 330 in a direction away from the short tube 304 (in the same direction the delivery wire 320 was pulled in the previous step of FIG. 32, i.e., proximally as defined herein). After the sheath 332 and delivery member 330 have been pulled in the direction of the arrow of FIG. 34 and out of the opening 313 in the short tube 304, the distal end of the sheath 332 is now free (see FIG. 35 showing the free (distal) end 336 of sheath 332 exposed from the short tube 304). Next, the delivery member 330 is grasped by the clinician (also shown in FIG. 35) and the delivery member 330 is pulled in a direction away from the long tube 302. It is pulled in this direction of the arrow until the proximal end of the delivery member 330 is exposed from the end 309 of the long tube 302, thereby exposing a free end 339 of delivery member 330 (see FIG. 36). As shown, the implant 250 is still contained within the delivery sheath 332. Now with the sheath 332 and delivery member 330 removed from the packaging hoops (tubes) 302, 304, the sheath 332 with internally contained delivery member 330 and coupled implant 250 can be inserted into or placed in abutment with a microcatheter for delivery of the implant through the microcatheter and into the body lumen, i.e., intracranial aneurysm, in the methods described above. If placed in abutment, the delivery sheath distal end 336 would abut the proximal end of the catheter, and then the delivery member and coupled implant advanced through a lumen in the catheter, with the delivery sheath remaining outside the catheter.

Note the packaging configuration 320 and cap 324 described above is just one way the implant can be packaged. Other packaging methods such as formed trays can also be employed with a recessed region to allow for the implant to be shipped in an expanded (secondary) state.

Note FIGS. 29 and 30 show one method of attachment of the delivery member to the implant which is the method of FIGS. 37-40 and 43. It should be understood, that other attachments can be utilized to pull the delivery member from the container and into the delivery sheath. That is, although the delivery member 320 and implant 250 are shown engaged by the arrangement of FIGS. 37-40 and 43 described above, they can be operatively connected by other methods such as the alternatives described herein, so that the delivery member can pull the implant 250 into the delivery sheath.

While the above description contains many specifics, those specifics should not be construed as limitations on the scope of the disclosure, but merely as exemplifications of preferred embodiments thereof. Those skilled in the art will envision many other possible variations that are within the scope and spirit of the disclosure as defined by the claims appended hereto.

What is claimed is:
1. A method for removing a vascular implant from a packaging, the packaging having a container to receive the implant, a first packaging tube and a second packaging tube, the method comprising the steps of:

a) pulling an elongated delivery member in a first direction to pull the vascular implant from the container into a delivery sheath positioned within the first packaging tube;
b) subsequently pulling the delivery sheath in the first direction until a first end of the delivery sheath is free of the first packaging tube; and
c) subsequently freeing an end of the delivery member from the second packaging tube, wherein the delivery member extends into the container to connect to the implant.

2. The method of claim 1, wherein the step of pulling the delivery member to pull the implant into the delivery sheath moves the implant to a more constrained condition having a smaller transverse dimension and prior to pulling the implant into the delivery sheath the implant has a transverse dimension larger than a transverse dimension of the delivery sheath.

3. The method of claim 1, wherein the step of pulling the delivery sheath in the first direction includes also pulling the delivery member in the first direction.

4. The method of claim 1, wherein one or both of the first and second packaging tubes are contained in a coiled configuration during shipping.

5. The method of claim 4, further comprising a series of clips retaining both the first and second packaging tubes in the coiled configuration.

6. The method of claim 1, wherein a portion of the delivery member and delivery sheath are exposed in a gap between the first and second packaging tubes.

7. The method of claim 6, wherein the gap has length less than a length of the first packaging tube and second packaging tube.

8. The method of claim 7, wherein the delivery member is exposed proximally of the delivery sheath in the gap.

9. The method of claim 6, wherein the delivery sheath terminates at one end in the gap between the first and second packaging tubes.

10. The method of claim 1, wherein the container has an internal space larger than a transverse dimension of the implant.

11. The method of claim 1, wherein the first and second packaging tubes have an arcuate configuration.

12. The method of claim 11, wherein the delivery wire extends into the first and second packaging tubes and the delivery sheath terminates distally of the second packaging tube.

13. The method of claim 1, further comprising further pulling the elongated delivery member in the first direction to free the delivery member from the first packaging tube.

14. The method of claim 1, wherein step (b) is performed after the implant is pulled fully into a lumen of the delivery sheath.

15. The method of claim 1, wherein the delivery wire extends into the first and second packaging tubes and the delivery sheath terminates distally of the second packaging tube.

16. A method for removing a vascular implant from a packaging, the packaging having a container to receive the implant, a first packaging tube and a second packaging tube, the method comprising the steps of:
a) pulling an elongated delivery member in a first direction to pull the vascular implant from the container into a delivery sheath positioned within the first packaging tube;
b) subsequently pulling the delivery sheath in the first direction until a first end of the delivery sheath is free of the first packaging tube; and
c) subsequently freeing an end of the delivery member from a second packaging tube,
wherein the step of freeing the delivery member comprises pulling the delivery member in a second direction opposite the first direction until the end of the delivery member is free of the second packaging tube.

17. The method of claim 16, wherein the delivery sheath extends into the container prior to step (b).

18. The method of claim 16, wherein the delivery member is exposed proximally of the delivery sheath in a gap between the first and second packaging tubes.

19. A method for removing a vascular implant from a packaging, the packaging having a container to receive the implant, a first packaging tube and a second packaging tube, the method comprising the steps of:
a) pulling an elongated delivery member in a first direction to pull the vascular implant from the container into a delivery sheath positioned within the first packaging tube;
b) subsequently pulling the delivery sheath in the first direction until a first end of the delivery sheath is free of the first packaging tube; and
c) subsequently freeing an end of the delivery member from a second packaging tube,
wherein the implant is positioned in the container in a three-dimensional helical configuration.

20. The method of claim 19, wherein the delivery member extends into the container to connect to the implant.

* * * * *